US011338103B2

(12) United States Patent
Blanch et al.

(10) Patent No.: US 11,338,103 B2
(45) Date of Patent: May 24, 2022

(54) HEADGEAR FOR A PATIENT INTERFACE

(71) Applicant: RESMED PTY LTD, Bella Vista (AU)

(72) Inventors: Emily Elizabeth Blanch, Sydney (AU); Michiel Kooij, Sydney (AU); Stewart Joseph Wagner, Hawkesbury (AU); Hadley White, Sydney (AU); Paul Derrick Watson, Sydney (AU); Ryan Michael Kirkpatrick, Sydney (AU)

( * ) Notice: Subject to any disclaimer, the term of this patent is extended or adjusted under 35 U.S.C. 154(b) by 0 days.

(21) Appl. No.: 17/269,916

(22) PCT Filed: Aug. 20, 2019

(86) PCT No.: PCT/AU2019/050874
§ 371 (c)(1),
(2) Date: Feb. 19, 2021

(87) PCT Pub. No.: WO2020/037360
PCT Pub. Date: Feb. 27, 2020

(65) Prior Publication Data
US 2021/0308406 A1   Oct. 7, 2021

Related U.S. Application Data

(60) Provisional application No. 62/764,995, filed on Aug. 20, 2018.

(51) Int. Cl.
*A61M 16/06*     (2006.01)
*A61M 16/08*     (2006.01)
*A61M 16/16*     (2006.01)

(52) U.S. Cl.
CPC .... *A61M 16/0683* (2013.01); *A61M 16/0616* (2014.02); *A61M 16/0666* (2013.01);
(Continued)

(58) Field of Classification Search
CPC .......... A61M 16/0057; A61M 16/0066; A61M 16/009; A61M 16/06; A61M 16/0611;
(Continued)

(56) References Cited

U.S. PATENT DOCUMENTS 2,376,871 A   5/1945  Fink
3,122,171 A   2/1964  Britton et al.
(Continued)

FOREIGN PATENT DOCUMENTS

CN   101142000 A   3/2008
CN   101405046 A   4/2009
(Continued)

OTHER PUBLICATIONS

"*Respiratory Physiology*", by John B. West, Lippincott Williams & Wilkins, $9^{th}$ edition published 2012 (8 pages).
(Continued)

*Primary Examiner* — Annette Dixon
(74) *Attorney, Agent, or Firm* — Nixon & Vanderhye P.C.

(57) ABSTRACT

A positioning and stabilising structure comprising at least one gas delivery tube to receive the flow of air from a connection port on top of the patient's head and to deliver the flow of air to the entrance of the patient's airways via the seal-forming structure, the at least one gas delivery tube comprising a tube wall having an extendable concertina structure comprising a plurality of folds in the tube wall alternatingly forming a plurality of ridges and a plurality of grooves, the folds able to be at least partially unfolded to increase a separation of the ridges to elongate the extendable concertina structure; and one or more ridge connecting portions provided to the tube wall, each of the one or more ridge connecting portions connecting two or more adjacent ridges of the plurality of ridges and being configured to resist the separation of the ridges.

17 Claims, 49 Drawing Sheets

(52) U.S. Cl.
CPC .... *A61M 16/0816* (2013.01); *A61M 16/0875* (2013.01); *A61M 16/0622* (2014.02); *A61M 16/16* (2013.01); *A61M 2205/42* (2013.01)

(58) Field of Classification Search
CPC .......... A61M 16/0616; A61M 16/0633; A61M 16/0666; A61M 16/0683; A61M 16/08; A61M 16/0816; A61M 16/0825; A61M 16/0858; A61M 16/0875; A61M 16/1055; A61M 16/1065; A61M 16/107; A61M 16/1075; A61M 16/16; A61M 16/161; A61M 16/208; A61M 2016/0027; A61M 2016/0036; A61M 2202/0085; A61M 2202/0225; A61M 2205/0205; A61M 2205/0238; A61M 2205/3368; A61M 2205/42; A61M 2210/0618; A62B 18/02
See application file for complete search history.

(56) References Cited

U.S. PATENT DOCUMENTS

| | | | |
|---|---|---|---|
| 3,513,844 | A | 5/1970 | Smith |
| 4,535,767 | A | 8/1985 | Tiep et al. |
| 4,782,832 | A | 11/1988 | Trimble et al. |
| 4,878,491 | A | 11/1989 | McGilvray, III |
| 4,944,310 | A | 7/1990 | Sullivan |
| 5,018,519 | A | 5/1991 | Brown |
| 5,069,222 | A | 12/1991 | McDonald, Jr. |
| 5,233,978 | A | 8/1993 | Callaway |
| 5,269,296 | A | 12/1993 | Landis |
| 5,438,979 | A | 8/1995 | Johnson, Jr. et al. |
| 5,538,000 | A | 7/1996 | Rudolph |
| 5,687,715 | A | 11/1997 | Landis |
| 6,021,816 | A | 2/2000 | Jeltsch et al. |
| 6,044,844 | A | 4/2000 | Kwok et al. |
| 6,478,026 | B1 | 11/2002 | Wood |
| 6,532,959 | B1 | 3/2003 | Berthon-Jones |
| 6,581,594 | B1 | 6/2003 | Drew et al. |
| 6,595,215 | B2 | 7/2003 | Wood |
| 6,679,265 | B2 | 1/2004 | Strickland et al. |
| 7,080,645 | B2 | 7/2006 | Genger et al. |
| 7,178,525 | B2 | 2/2007 | Matula, Jr. et al. |
| 7,370,652 | B2 | 5/2008 | Matula, Jr. et al. |
| 7,735,490 | B2 | 6/2010 | Rinaldi |
| 7,856,982 | B2 | 12/2010 | Matula, Jr. et al. |
| 7,866,944 | B2 | 1/2011 | Kenyon et al. |
| 7,900,628 | B2 | 3/2011 | Matula, Jr. et al. |
| 8,297,285 | B2 | 10/2012 | Henry et al. |
| 8,636,479 | B2 | 1/2014 | Kenyon et al. |
| 8,638,014 | B2 | 1/2014 | Sears et al. |
| 8,648,259 | B2 | 2/2014 | Gniewek et al. |
| 8,667,962 | B2 | 3/2014 | Kenyon et al. |
| 8,733,349 | B2 | 5/2014 | Bath et al. |
| 8,770,230 | B2 | 7/2014 | Steinhanses et al. |
| 8,826,909 | B2 * | 9/2014 | Nashed ................ A61M 16/06 128/206.28 |
| 8,985,115 | B2 | 3/2015 | Baecke et al. |
| 9,162,034 | B2 | 10/2015 | Veliss et al. |
| 9,365,004 | B2 | 6/2016 | Forrester |
| 9,731,090 | B2 | 8/2017 | Ovzinsky et al. |
| 9,764,107 | B2 | 9/2017 | Grashow et al. |
| 10,744,291 | B2 | 8/2020 | Kwok et al. |
| 2004/0025885 | A1 | 2/2004 | Payne, Jr. |
| 2005/0092329 | A1 | 5/2005 | Sta-Maria |
| 2005/0205096 | A1 | 9/2005 | Matula et al. |
| 2006/0213521 | A1 | 9/2006 | Radney |
| 2006/0231102 | A1 | 10/2006 | Bordewick et al. |
| 2007/0246043 | A1 | 10/2007 | Kwok et al. |
| 2008/0053451 | A1 | 3/2008 | Bordewick et al. |
| 2008/0060649 | A1 | 3/2008 | Veliss et al. |
| 2009/0044808 | A1 | 2/2009 | Guney et al. |
| 2009/0050156 | A1 * | 2/2009 | Ng .................... A61M 16/0066 128/205.24 |
| 2009/0078259 | A1 | 3/2009 | Kooij |
| 2010/0000534 | A1 | 1/2010 | Kooij et al. |
| 2010/0018534 | A1 | 1/2010 | Veliss et al. |
| 2010/0313891 | A1 | 12/2010 | Veliss et al. |
| 2011/0030692 | A1 * | 2/2011 | Jones ................ A61M 16/0616 128/206.21 |
| 2011/0240031 | A1 | 10/2011 | Jaffre |
| 2011/0247619 | A1 | 10/2011 | Formica et al. |
| 2012/0067349 | A1 | 3/2012 | Barlow et al. |
| 2012/0266890 | A1 | 10/2012 | Baecke et al. |
| 2012/0325219 | A1 | 12/2012 | Smith |
| 2013/0319408 | A1 | 12/2013 | Zwolinsky |
| 2014/0102456 | A1 | 4/2014 | Ovizinksy |
| 2014/0137870 | A1 | 5/2014 | Barlow |
| 2015/0083136 | A1 | 3/2015 | Grashow et al. |
| 2015/0128949 | A1 | 5/2015 | Jablonski |
| 2015/0182719 | A1 | 7/2015 | Grashow et al. |
| 2015/0352306 | A1 | 12/2015 | Scheiner et al. |
| 2016/0030696 | A1 * | 2/2016 | Klenner ............ A61M 16/0622 128/207.18 |
| 2016/0082214 | A1 | 3/2016 | Barlow et al. |
| 2016/0296720 | A1 | 10/2016 | Henry et al. |
| 2017/0224944 | A1 | 8/2017 | Gunaratnam et al. |
| 2017/0291004 | A1 | 10/2017 | Ng et al. |
| 2017/0312468 | A1 | 11/2017 | Formica et al. |
| 2017/0326320 | A1 * | 11/2017 | Baigent ............ A61M 16/0616 |
| 2017/0333658 | A1 | 11/2017 | Haibach |
| 2018/0099113 | A1 | 4/2018 | Bell et al. |
| 2018/0140795 | A1 | 5/2018 | Wells et al. |

FOREIGN PATENT DOCUMENTS

| | | |
|---|---|---|
| CN | 101495170 A | 7/2009 |
| CN | 102791314 A | 11/2012 |
| CN | 104602745 A | 5/2015 |
| WO | WO 98/004310 A1 | 2/1998 |
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | 2005/076874 | 8/2005 |
| WO | 2005/086943 | 9/2005 |
| WO | 2005/099801 | 10/2005 |
| WO | WO 2006/074513 A1 | 7/2006 |
| WO | WO 2006/130903 A1 | 12/2006 |
| WO | 2007/028877 | 3/2007 |
| WO | 2008/011682 | 1/2008 |
| WO | 2008/011683 | 1/2008 |
| WO | 2008/070929 | 6/2008 |
| WO | WO 2009/052560 A1 | 4/2009 |
| WO | 2009/139647 | 11/2009 |
| WO | 2010/131189 | 11/2010 |
| WO | WO 2010/135785 A1 | 12/2010 |
| WO | 2011/110962 | 11/2011 |
| WO | 2012/061783 | 5/2012 |
| WO | 2012/107858 | 8/2012 |
| WO | WO 2012/171072 A1 | 12/2012 |
| WO | WO 2013/020167 A1 | 2/2013 |
| WO | 2013/156960 | 10/2013 |
| WO | 2014/013371 | 1/2014 |
| WO | 2015/125080 | 8/2015 |
| WO | 2016/193859 | 12/2016 |
| WO | 2017/124152 | 7/2017 |
| WO | 2017/124155 | 7/2017 |
| WO | 2017/185140 | 11/2017 |

OTHER PUBLICATIONS

International Search Report dated Nov. 12, 2019 issued in International Application No. PCT/AU2019/050874 (8 pages).
Written Opinion dated Nov. 12, 2019 issued in International Application No. PCT/AU2019/050874 (10 pages).
International Preliminary Report on Patentability dated Jul. 16, 2020 issued in International Application No. PCT/AU2019/050874 (52 pages).

* cited by examiner

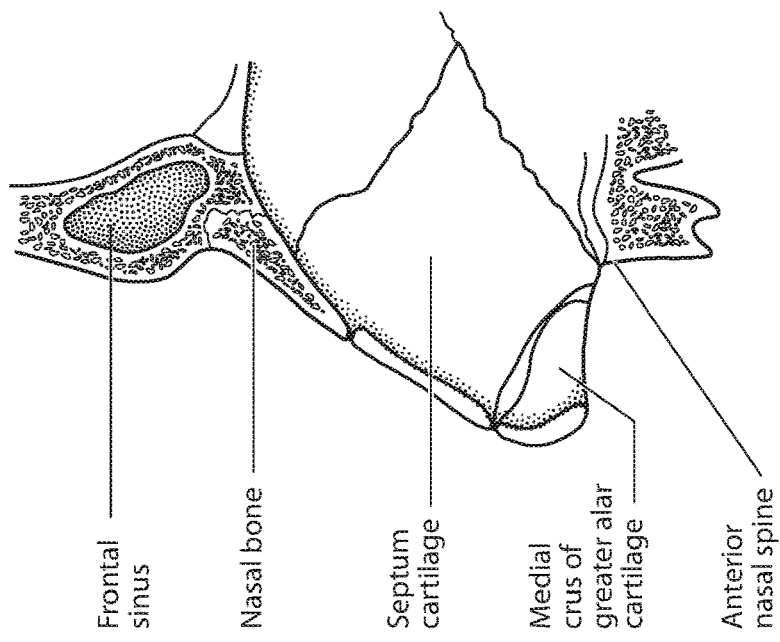
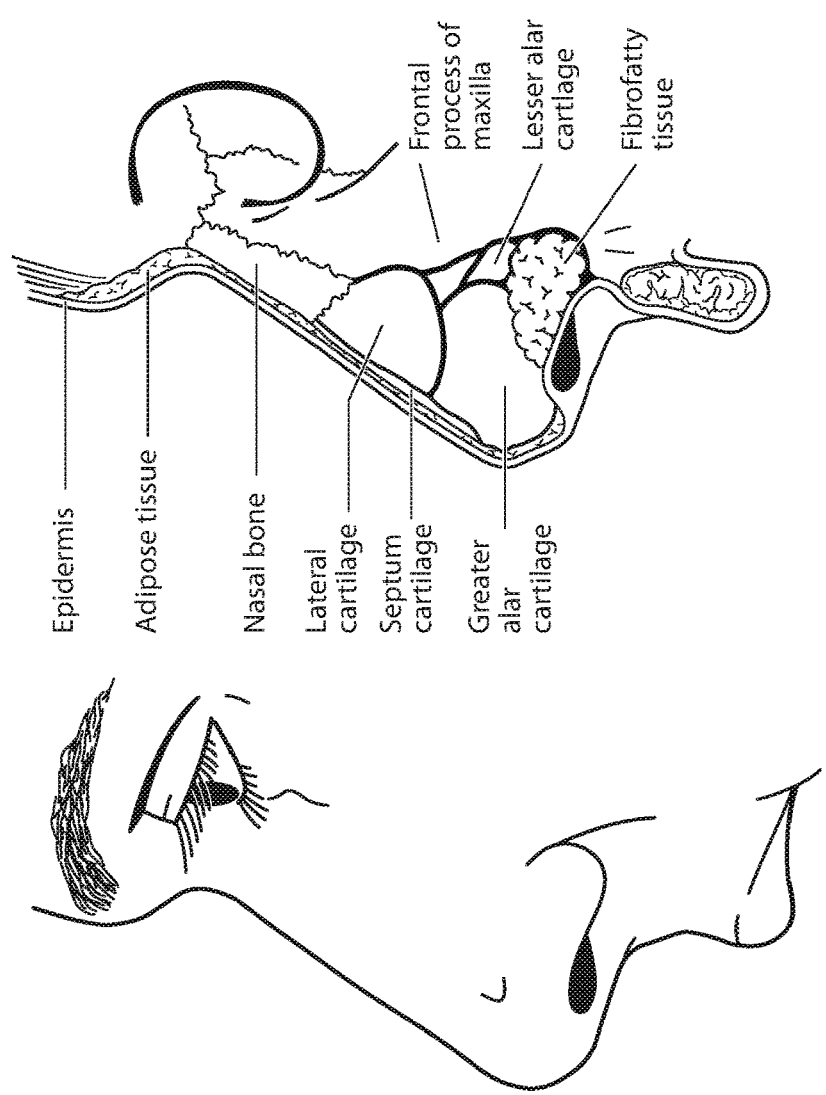
FIG. 2G  FIG. 2H  FIG. 2I

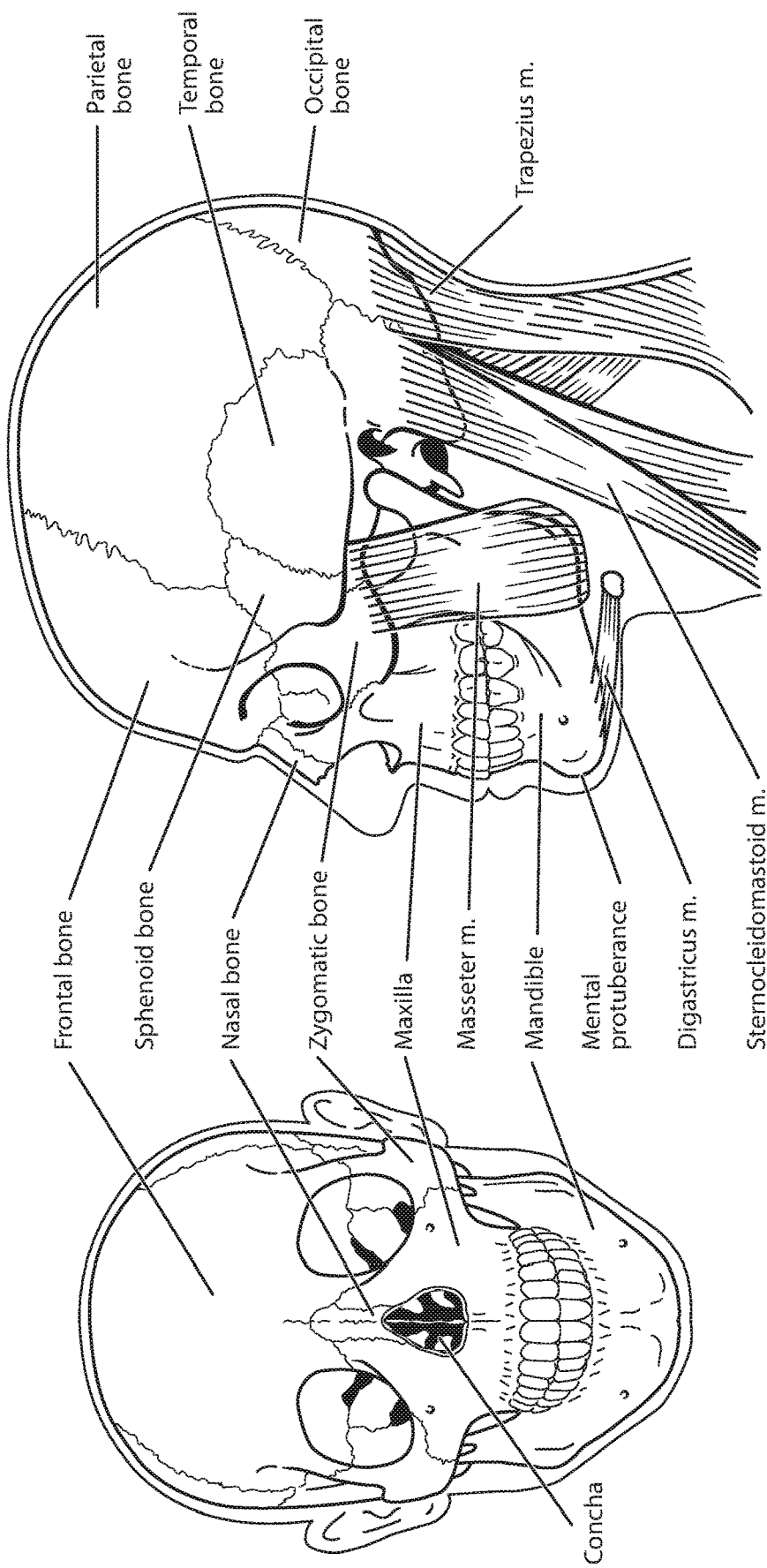

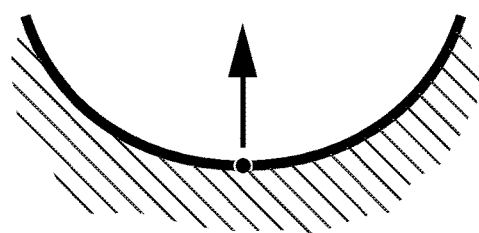
FIG. 3B — Relatively Large Positive Curvature
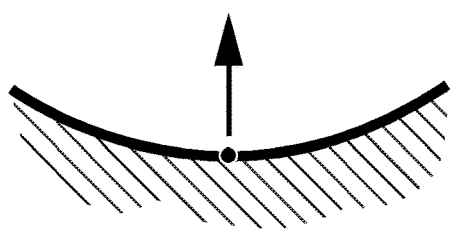
FIG. 3C — Relatively Small Positive Curvature
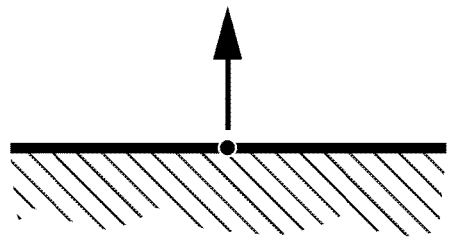
FIG. 3D — Zero Curvature
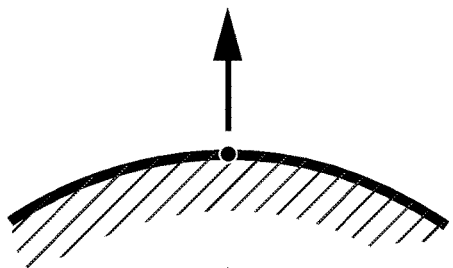
FIG. 3E — Relatively Small Negative Curvature
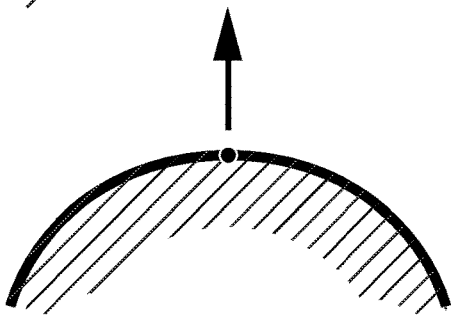
FIG. 3F — Relatively Large Negative Curvature
Copyright 2015 ResMed Limited

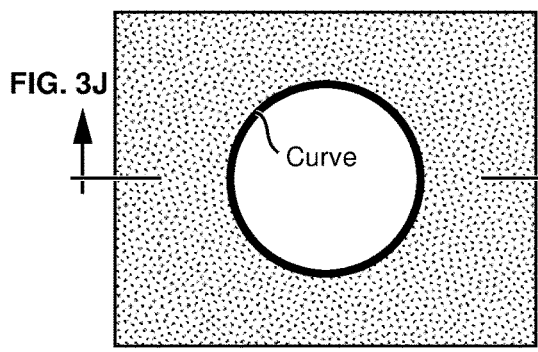
FIG. 3I
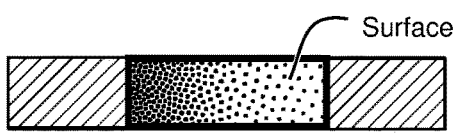
FIG. 3J
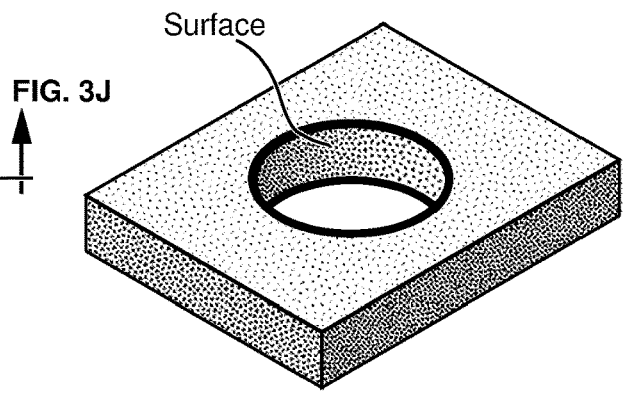
FIG. 3K
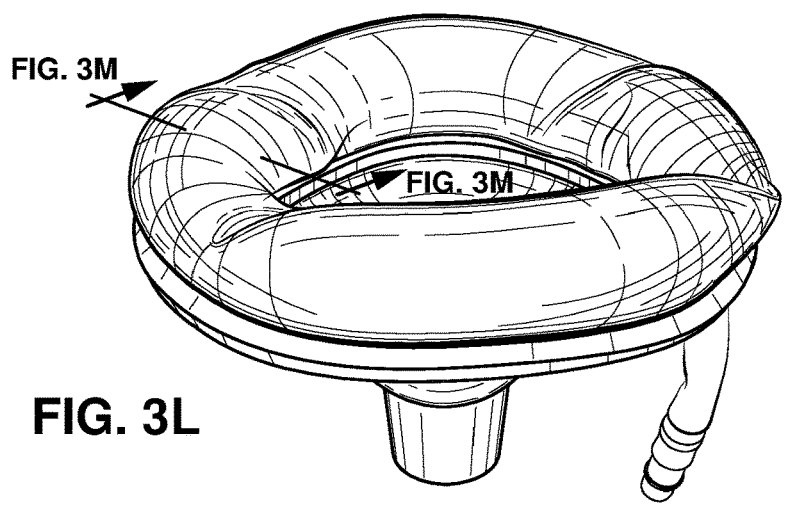
FIG. 3L
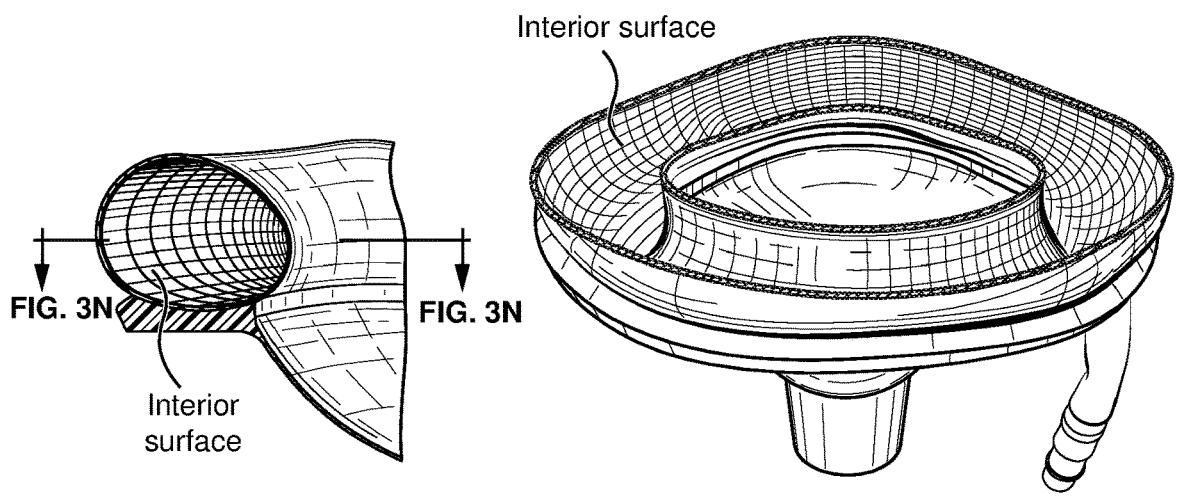
FIG. 3M     FIG. 3N

Left-hand rule

Right-hand rule

Left ear helix

Right-hand helix
Right-hand positive

Right ear helix

Copyright 2015 ResMed Limited

HEADGEAR FOR A PATIENT INTERFACE

1 CROSS-REFERENCE TO RELATED APPLICATIONS

This application is the U.S. national phase of International Application No. PCT/AU2019/050874 filed Aug. 20, 2019 which designated the U.S. and claims priority to U.S. Provisional Application No. 62/764,995, filed Aug. 20, 2018, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY 2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See *"Respiratory Physiology"*, by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fits and is comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004310; WO 2006/074513; WO 2010/135785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063328 and WO 2006/130903 (describing amongst other things aspects of the ResMed Limited MIRAGE LIBERTY™ full-face mask); International Patent Application WO 2009/052560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.1.3 Pressurised Air Conduit

In one type of treatment system, a flow of pressurised air is provided to a patient interface through a conduit in an air circuit that fluidly connects to the patient interface so that, when the patient interface is positioned on the patient's face during use, the conduit extends out of the patient interface forwards away from the patient's face. This may sometimes be referred to as an "elephant trunk" style of interface.

Some patients find such interfaces to be unsightly and are consequently deterred from wearing them, reducing patient compliance. Additionally, conduits connecting to an interface at the front of a patient's face may sometimes be vulnerable to becoming tangled up in bed clothes.

2.2.3.1.4 Pressurised Air Conduit Used for Positioning/Stabilising the Seal-Forming Structure An alternative type of treatment system which seeks to address these problems comprises a patient interface in which a tube that delivers pressurised air to the patient's airways also functions as part of the headgear to position and stabilise the seal-forming portion of the patient interface to the appropriate part of the patient's face. This type of patient interface may be referred to as incorporating 'headgear tubing' or 'conduit headgear'. Such patient interfaces allow the conduit in the air circuit providing the flow of pressurised air from a respiratory pressure therapy device to connect to the patient interface in a position other than in front of the patient's face. One example of such a treatment system is disclosed in US Patent Publication No. 2007/0246043, the contents of which are incorporated herein by reference, in which the conduit connects to a tube in the patient interface through a port positioned in use on top of the patient's head.

The Philips DreamWear™ mask includes such headgear tubing. The length of the DreamWear™ headgear tubes cannot be adjusted. Consequently, the DreamWear™ headgear is supplied in three different sizes to cater for different sized patient faces. Providing a greater number of different sizes may increase the complexity and cost to manufacture the headgear and may result in larger packaging. Additionally, a supply of discretely sized masks may limit the extent to which differently sized patient heads can be accommodated. There may be a greater chance of some patients being unable to achieve what they consider a "perfect" fit if forced to choose between discrete sizes that are not adjustable in length.

Patient interfaces incorporating headgear tubing may provide some advantages, for example avoiding a conduit connecting to the patient interface at the front of a patient's face, which may be unsightly and obtrusive. However, it is desirable for patient interfaces incorporating headgear tubing to be comfortable for a patient to wear over a prolonged duration when the patient is asleep while forming an effective seal with the patient's face.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

The designer of a device may be presented with an infinite number of choices to make Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MRDs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cm H$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21(3) | 13 (3) | 2014 |

(* one specimen only, measured using test method specified in ISO 3744 in CPAP mode at 10 cm H$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculography (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One aspect of the present technology comprises a patient interface for delivery of a supply of pressurised breathable gas to an entrance of a patient's airways.

Another aspect of the present technology is directed to a patient interface that may comprise: a plenum chamber; a seal-forming structure; and a positioning and stabilising structure. The patient interface may further comprise a vent structure. The patient may further be configured to leave the patient's mouth uncovered, or if the seal-forming structure is configured to seal around the patient's nose and mouth, the patient interface may be further configured to allow the patient to breath from ambient in the absence of a flow of pressurised air through the plenum chamber inlet port.

Another aspect of the present technology is directed to a patient interface that includes: a plenum chamber; a seal-forming structure; a vent structure; and a positioning and stabilising structure to provide a force to hold a seal-forming structure in a therapeutically effective position on a patient's head. The positioning and stabilising structure including at least one gas delivery tube to receive the flow of air from a connection port and to deliver the flow of air to the entrance of the patient's airways via the seal-forming structure, the gas delivery tube being constructed and arranged to contact, in use, at least a region of the patient's head superior to an otobasion superior of the patient's head.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

at least one gas delivery tube to receive the flow of air from a connection port on top of the patient's head and to deliver the flow of air to the entrance of the patient's airways via the seal-forming structure, the gas delivery tube being constructed and arranged to contact, in use, at least a region of the patient's head superior to an otobasion superior of the patient's head, the gas delivery tube comprising:

a tube wall defining a hollow interior through which air is able to flow to the seal-forming structure, the tube wall having an extendable portion configured to be extended to vary a length of the gas delivery tube;

wherein the extendable portion comprises an extension stiffness within the range of 0.2 to 0.35 N/mm.

In examples of any of the aspects of any of the preceding paragraphs: (a) the extension stiffness of the extendable portion is within the range of 0.25 to 0.3 N/mm; (b) the pair of gas delivery tubes comprise a combined unextended length, measured along a centreline of a side of the pair of tubes configured to be patient-facing in use, within the range of 500 to 535 mm; (c) the combined unextended length is within the range of 510 to 525 mm; (d) the combined unextended length is within the range of 512 to 522 mm; (e) the pair of gas delivery tubes comprise a combined unextended length, measured along a centreline of a side of the pair of tubes configured to be patient-facing in use, within the range of 460 to 500 mm; (f) the combined unextended length is within the range of 470 to 490 mm; (g) the combined unextended length is within the range of 475 to 485 mm; (h) the gas delivery tubes form a loop around the patient's head together with a cushion module, the loop having an unextended length, measured along a centreline of a side of the gas delivery tubes and cushion module configured to be patient-facing in use, within the range of 510 to 610 mm; (i) the unextended length of the loop is within the range of 528 to 548 mm; (j), the unextended length of the loop is within the range of 535 to 541 mm; (k) the unextended length of the loop is within the range of 534 to 554 mm (l) the unextended length of the loop is within the range of 539 to 549 mm; (m) the unextended length of the loop is within the range of 541 to 561 mm; (n) the unextended length of the loop is within the range of 546 to 556 mm; (o) the unextended length of the loop is within the range of 564 to 584 mm; (p) the unextended length of the loop is within the range of 571 to 581 mm; (q) the unextended length of the loop is within the range of 577 to 597 mm; and/or (r) the unextended length of the loop is within the range of 582 to 592 mm.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

at least one gas delivery tube to receive the flow of air from a connection port on top of the patient's head and to deliver the flow of air to the entrance of the patient's airways via the seal-forming structure, the at least one gas delivery tube being constructed and arranged to contact, in use, at least a region of the patient's head superior to an otobasion superior of the patient's head, the at least one gas delivery tube comprising:

a superior tube portion configured, in use, to overlie a superior region of the patient's head, the superior tube portion comprising:

a first end configured, in use, to overlie a superior portion of the patient's head at or proximate the sagittal plane of the patient's head;

a second end configured, in use, to overlie a side portion of the patient's head;

a stiffened portion between the first end and the second end configured to provide a higher resistance to relative movement between the first end and the second end in an anterior and/or posterior direction than in a superior and/or inferior direction in use;

an inferior tube portion connected between the second end of the superior tube portion and the seal-forming structure.

In examples of any of the aspects of any of the preceding paragraphs: (a) each superior tube portion comprises two stiffened portions; (b) the stiffened portions are provided to one or both of a side of the superior tube portion configured to be anterior in use and a side of the superior tube portion configured to be posterior in use; (c) the superior tube portion comprises an extendable portion; (d) the extendable portion comprises an extendable concertina structure formed in a tube wall of the gas delivery tube; (e) the extendable concertina structure comprises plurality of folds in the tube wall alternatingly forming a plurality of ridges and a plurality of grooves; (f) the stiffened portion comprises a plurality of connecting portions formed in the tube wall, each of the plurality of connecting portions connecting a pair of adjacent ridges; and/or (g) the stiffened portions are integrally formed with the superior tube portion.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

at least one gas delivery tube to receive the flow of air from a connection port on top of the patient's head and to deliver the flow of air to the entrance of the patient's airways via the seal-forming structure, the at least one gas delivery tube being constructed and arranged to contact, in use, at least a region of the patient's head superior to an otobasion superior of the patient's head, the at least one gas delivery tube comprising a tube wall having an extendable concertina structure comprising:

a plurality of folds in the tube wall alternatingly forming a plurality of ridges and a plurality of grooves, the folds able to be at least partially unfolded to increase a separation of the ridges to elongate the extendable concertina structure; and one or more ridge connecting portions provided to the tube wall, each of the one or more ridge connecting portions connecting two or more adjacent ridges of the plurality of ridges and being configured to resist the separation of the ridges.

In examples of any of the aspects of any of the preceding paragraphs: (a) each pair of adjacent ridges is connected by at least one ridge connecting portion of the one or more ridge connecting portions; (b) one or more pairs of adjacent ridges are connected by two ridge connecting portions; (c) each pair of adjacent ridges is connected by two ridge connecting portions; (d) one or more of the ridge connecting portions is located on a side of the gas delivery tube configured to be anterior-facing in use; (e) one or more of the ridge connecting portions is located on a side of the gas delivery tube configured to be posterior-facing in use; (f) each of the ridge connecting portions is spaced centrally between a side of the gas delivery tube configured to be inferior-facing in use and a side of the gas delivery tube configured to be superior-facing in use; (g) each pair of adjacent ridges is connected by one of the ridge connecting portion located on the side of the gas delivery tube configured to be anterior-facing in use; (h) each pair of adjacent ridges is connected by one of the ridge connecting portion located on the side of the gas delivery tube configured to be posterior-facing; (i) the gas delivery tube comprises a non-extendable portion having an outer surface and each of the plurality of grooves is formed as a depression with respect to the outer surface of the non-extendable portion; (j) the gas delivery tube comprises a non-extendable portion having an outer surface and each of the plurality of ridges is raised with respect to the outer surface of the non-extendable portion; (k) each of the plurality of grooves is located between a respective pair of ridge connecting portions, each ridge connecting portion of the pair of ridge connecting portions being located at a respective end of the respective groove; (l) each of the plurality of grooves comprises a groove depth and each of the plurality of ridge connecting portions comprises a ridge connecting portion height, the groove depth of each respective groove being equal to the ridge connecting portion height of each of the respective pair of ridge connecting portions located at the ends of the respective groove; (m) each ridge connection portion is an integrally formed portion of the tube wall; (n) the plurality of ridges, the plurality of grooves and the plurality of ridge connecting portions are integrally formed; (o) each of the plurality of ridges comprises a curved ridge portion central to the respective ridge; (p) each of the plurality of grooves comprises a curved groove portion central to the respective groove; (q) each of the plurality of ridges comprises a pair of straight ridge portions provided at opposite ends of the respective ridge; (r) each of the plurality of ridge connecting portions connects the respective adjacent pair of ridges at the straight ridge portions of the ridge; (s) the gas delivery tube at the extendable concertina structure comprises a cross-section having a width and a height, the width being aligned in use substantially with the anterior-posterior directions, the width being larger than the height; (t) the width is at least twice as large as the height; and/or (u) the positioning and stabilising structure comprises two gas delivery tubes fluidly connected between the connection port and the seal-forming structure, each gas delivery tube extending, in use, across one of the patient's cheek regions, the two gas delivery tubes being on different sides of the patient's head.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

at least one gas delivery tube to receive the flow of air from a connection port on top of the patient's head and to deliver the flow of air to the entrance of the patient's airways via the seal-forming structure, the at least one gas delivery tube being constructed and arranged to contact, in use, at least a region of the patient's head superior to an otobasion superior of the patient's head, the at least one gas delivery tube comprising a tube wall having a hollow interior and having an extendable concertina structure provided along a length of the gas delivery tube, the extendable concertina structure comprising:

a plurality of folds in the tube wall forming a first alternating series of ridges and grooves along a non-patient-contacting side of the gas delivery tube and a second alternating series of ridges and grooves along a patient-contacting side of the gas delivery tube;

wherein the first alternating series of ridges and grooves has a lesser extension stiffness than the second alternating series of ridges and grooves.

In examples: (a) the plurality of folds form, interior to the gas delivery tube, interior ridges and interior grooves forming the first alternating series of ridges and grooves and the second alternating series of ridges and grooves; (b) each one of the interior grooves of the first alternating series is provided opposite a respective one of the interior grooves of the second alternating series across the interior of the gas delivery tube to form a plurality of opposing groove pairs, each opposing groove pair comprising: a first interior groove, being one interior groove of the first alternating series; and a second interior groove, being one interior groove of the second alternating series; wherein the first interior groove comprises a greater groove depth than the second interior groove; (c) the tube wall comprises a greater material thickness at a base of the second interior groove of each opposing groove pair than at a base of the first interior groove of the respective opposing groove pair; (d) the material thickness of the tube wall at the base of each interior groove of the second alternating series reduces along the length of the gas delivery tube from a first end proximate the connection port to a second end; (e) the material thickness of the tube wall at the base of each interior groove of the first alternating series is substantially constant along the length of the gas delivery tube; (f) the groove depths of the interior grooves of the first and second alternating series of interior ridges and interior grooves reduce along the length of the gas delivery tube from a first end adjacent the connection port to a second end; and/or (g) the first interior groove of each opposed groove pair is joined to the second interior groove of the respective opposed groove pair at sides of the gas delivery tube between the non-patient-contacting side and the patient-contacting side.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

a pair of gas delivery tubes to receive the flow of air from a connection port on top of the patient's head and to deliver the flow of air to the entrance of the patient's airways via the seal-forming structure, each of the pair of gas delivery tubes being constructed and arranged to contact, in use, at least a region of the patient's head superior to an otobasion superior of the patient's head, and each gas delivery tube comprising:

a tube wall defining a hollow interior along the length of the gas delivery tube;

a tab connected to the tube wall and configured, in use, to be located superior to the otobasion superior of the patient's head; and a slit formed in the tab, the slit spaced posteriorly in use from the tube wall, the slit comprising a superior end and an inferior end, wherein the superior end of the slit is spaced further from the tube wall than the inferior end of the slit; and a strap constructed and arranged to contact, in use, a region of the patient's head inferior to or overlaying an occipital bone of the patient's head, the strap being configured to connect to and between the slits.

In examples of any of the aspects of any of the preceding paragraphs: (a) each tab is integrally formed with a respective tube wall; (b) each tab has a superior edge and an inferior edge, the superior edge being longer than the inferior edge; (c) the inferior end of the slit is spaced from the tube wall by at least 5 mm; (d) the inferior end of the slit is spaced from the tube wall at least 7 mm; (e) the inferior end of the slit is spaced from the tube wall by 8 mm or more; (f) the superior end of the slit is spaced from the tube wall by at least 8 mm; (g) the superior end of the slit is spaced from the tube wall by at least 10 mm; (h) the superior end of the slit is spaced from the tube wall by 12 mm or more; (i) a midpoint along the slit is spaced from the tube wall by a spacing within the range of 5 mm to 30 mm; (j) the spacing is within the range of 7 mm to 20 mm; (k) the spacing is within the range of 8 mm to 15 mm; (l) the spacing is within the range of 9 to 11 mm; (m) each gas delivery tube comprises an extendable tube section located superior in use to the tab of the respective gas delivery tube and a non-extendable tube section located inferior in use to the tab of the respective gas delivery tube; (n) each tab is joined to the tube wall of the respective gas delivery tube at the non-extendable tube section; (o) each slit is arcuate between the superior end and the inferior end; (p) each slit is straight between the superior end and the inferior end; and/or (q) each slit is oriented perpendicular to the direction from the slit of a strap anchor region against which the strap is anchored around the patient's head.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

a pair of gas delivery tubes to receive the flow of air from a connection port on top of the patient's head and to deliver the flow of air to the entrance of the patient's airways via the seal-forming structure, each of the pair of gas delivery tubes being constructed and arranged to contact, in use, at least a region of the patient's head superior to an otobasion superior of the patient's head, and each gas delivery tube comprising:

a tube wall configured, in use, to overlie the patient's head along a path from a superior portion of the patient's head to the seal forming structure passing between an eye and an ear of the patient;

a tab connected to the tube wall and configured, in use, to be located superior to the otobasion superior of the patient's head; and a slit formed in the tab and spaced posteriorly in use from a slit-adjacent portion of the path of the tube wall;

wherein the slit has a posterosuperior-anteroinferior orientation in use and forms an oblique angle with a tangent of the path of the tube wall at the slit-adjacent portion; and a strap constructed and arranged to contact, in use, a region of the patient's head inferior to or overlaying an occipital bone of the patient's head, the strap being configured to connect to and between the slits.

In examples of any of the aspects of any of the preceding paragraphs: (a) each tab is integrally formed with a respective one of the tube walls; (b) each tab has a superior edge and an inferior edge in use, the superior edge being longer than the inferior edge; (c) each gas delivery tube comprises an extendable tube section superior to the tab of the respective gas delivery tube in use and a non-extendable tube section inferior to the tab of the respective gas delivery tube in use; (d) each tab is connected to the tube wall of the respective gas delivery tube at the non-extendable tube section; (e) each slit is arcuate between a superior end and an inferior end of the slit; (f) each slit is straight between a superior end and an inferior end of the slit; (g) an inferior end of the slit is spaced from the tube wall by at least 5 mm; (h) the inferior end of the slit is spaced from the tube wall at least 7 mm (i) the inferior end of the slit is spaced from the tube wall by 8 mm or more; (j) a superior end of the slit is spaced from the tube wall by at least 8 mm; (k) the superior end of the slit is spaced from the tube wall by at least 10 mm; (l) the superior end of the slit is spaced from the tube wall by 12 mm or more; (m) the oblique angle is in the range of 10 to 20 degrees; (n) the oblique angle is in the range of 12 to 18 degrees; and/or (o) each slit is oriented perpendicular to the direction from the slit of a strap anchor region against which the strap is anchored around the patient's head.

According to one aspect of the present technology there is provided a positioning and stabilising structure to provide a force to hold a seal-forming structure in a therapeutically effective position on a patient's head, the seal-forming structure constructed and arranged to form a seal with a region of the patient's face surrounding an entrance to the patient's airways for sealed delivery of a flow of air at a therapeutic pressure of at least 6 cmH$_2$O above ambient air pressure throughout the patient's respiratory cycle in use, the positioning and stabilising structure comprising:

a pair of gas delivery tubes to receive the flow of air from a connection port on top of the patient's head and to deliver the flow of air to the entrance of the patient's airways via the seal-forming structure, each of the pair of gas delivery tubes being constructed and arranged to contact, in use, at least a region of the patient's head superior to an otobasion superior of the patient's head, and each gas delivery tube comprising:

a tube wall configured to overlie the patient's head from a superior portion of the patient's head to the seal forming structure passing between an eye and an ear of the patient; and a tab connected to the tube wall and located superior to the otobasion superior of the patient's head in use;

an eyelet formed in the tab and located posteriorly to the tube wall in use;

a trough formed in the tab and located posteriorly to the eyelet; and a strap constructed and arranged to contact, in use, a region of the patient's head inferior to or overlaying an occipital bone of the patient's head, the strap being configured to connect to and between the eyelets of the pair of gas delivery tubes and to lie within the troughs formed in the tabs in use.

In examples of any of the aspects of any of the preceding paragraphs: (a) the trough is formed in the tab between the eyelet and a posterior side of the tab; (b) the tab comprises an outwardly facing surface and the trough comprises a substantially planar surface formed as a depression with respect to the outwardly facing surface; (c) the trough is formed by a portion of the tab having a reduced material thickness in comparison to other portions of the tab; (d) the trough comprises a length approximately equal to the width of the strap; and/or (e) the eyelet is in the form of a slit.

According to one aspect of the present technology, there is provided a patient interface comprising:

a plenum chamber pressurisable to a therapeutic pressure of at least 6 cmH$_2$O above ambient air pressure, said plenum chamber including a plenum chamber inlet port sized and structured to receive a flow of air at the therapeutic pressure for breathing by a patient, a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;

the positioning and stabilising structure according to any one of the above aspects; and a vent structure to allow a continuous flow of gases exhaled by the patient from an interior of the plenum chamber to ambient, said vent structure being sized and shaped to maintain the therapeutic pressure in the plenum chamber in use;

wherein the patient interface is configured to allow the patient to breath from ambient through their mouth in the absence of a flow of pressurised air through the plenum chamber inlet port, or the patient interface is configured to leave the patient's mouth uncovered.

Another aspect of certain forms of the present technology is a system for treating a respiratory disorder comprising a patient interface according to any one or more of the other aspects of the present technology, an air circuit and a source of air at positive pressure.

Another aspect of one form of the present technology is a patient interface that is moulded or otherwise constructed with a perimeter shape which is complementary to that of an intended wearer.

Another aspect of certain forms of the present technology is a patient interface comprising a seal-forming structure configured to leave the patient's mouth uncovered in use.

Another aspect of certain forms of the present technology is a patient interface comprising a seal-forming structure configured so that no part of the seal-forming structure enters the mouth in use.

Another aspect of certain forms of the present technology is a patient interface comprising a seal-forming structure configured so that the seal-forming structure does not extend internally of the patient's airways.

Another aspect of certain forms of the present technology is a patient interface comprising a seal-forming structure configured so that the seal-forming structure does not extend below a mental protuberance region in use.

Another aspect of certain forms of the present technology is a patient interface constructed and arranged to leave a patient's eyes uncovered in use.

Another aspect of certain forms of the present technology is a patient interface constructed and arranged to allow a patient to breathe ambient air in the event of a power failure.

Another aspect of certain forms of the present technology is a patient interface comprising a seal forming structure configured to form a seal on an underside of a patient's nose without contacting a nasal bridge region of the patient's nose.

Another aspect of certain forms of the present technology is a patient interface comprising a vent and a plenum chamber, wherein the patient interface is constructed and arranged so that gases from an interior of the plenum chamber may pass to ambient via the vent.

Another aspect of certain forms of the present technology is a patient interface constructed and arranged so that a patient may lie comfortably in a side or lateral sleeping position, in use of the patient interface.

Another aspect of certain forms of the present technology is a patient interface constructed and arranged so that a patient may lie comfortably in a supine sleeping position, in use of the patient interface.

Another aspect of certain forms of the present technology is a patient interface constructed and arranged so that a patient may lie comfortably in a prone sleeping position, in use of the patient interface.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a patient interface that may be washed in a home of a patient, e.g., in soapy water, without requiring specialised cleaning equipment.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 2A:
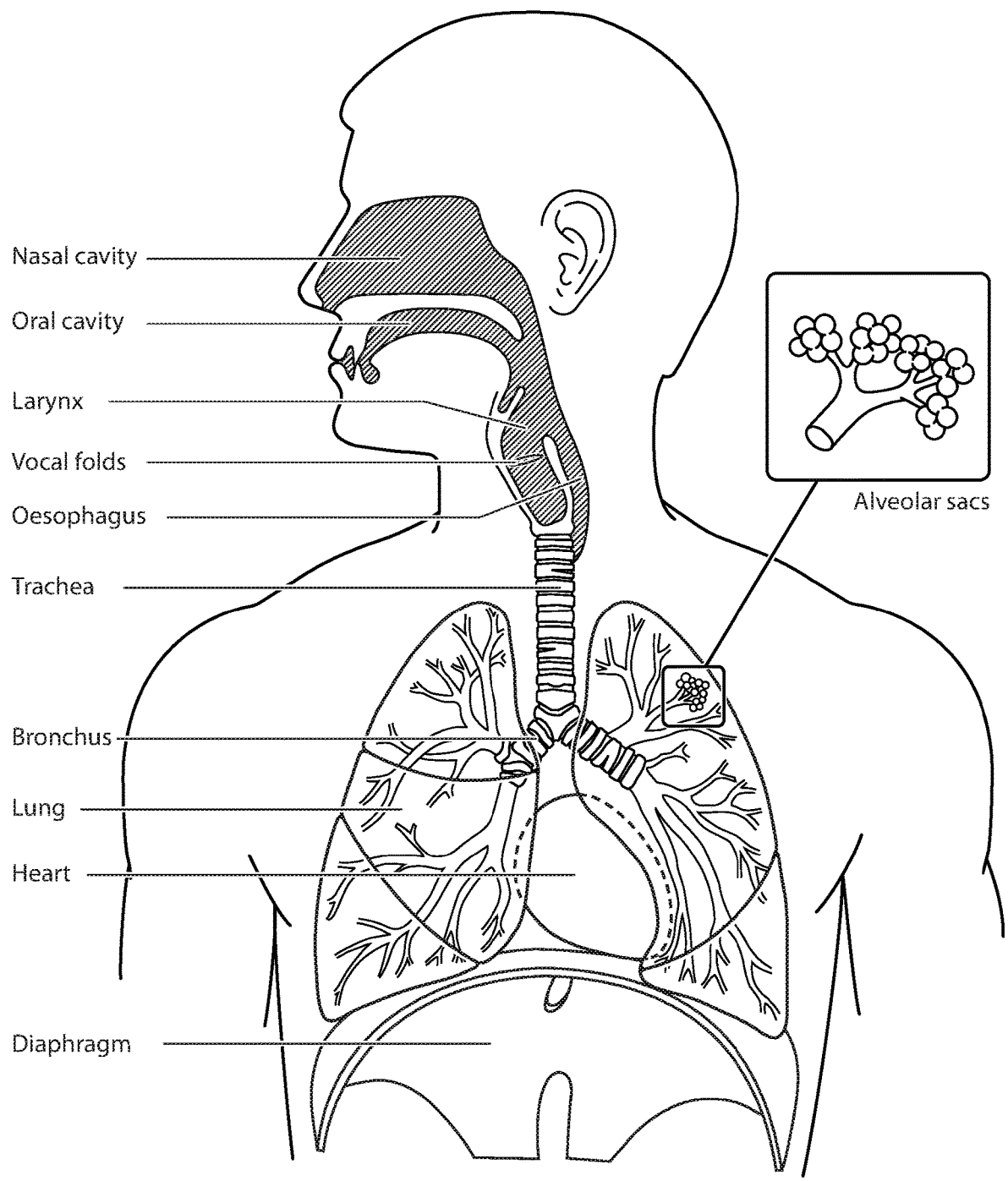
FIG. 2A shows an overview of a human respiratory system including the nasal and oral cavities, the larynx, vocal folds, oesophagus, trachea, bronchus, lung, alveolar sacs, heart and diaphragm.
Figure 2B:
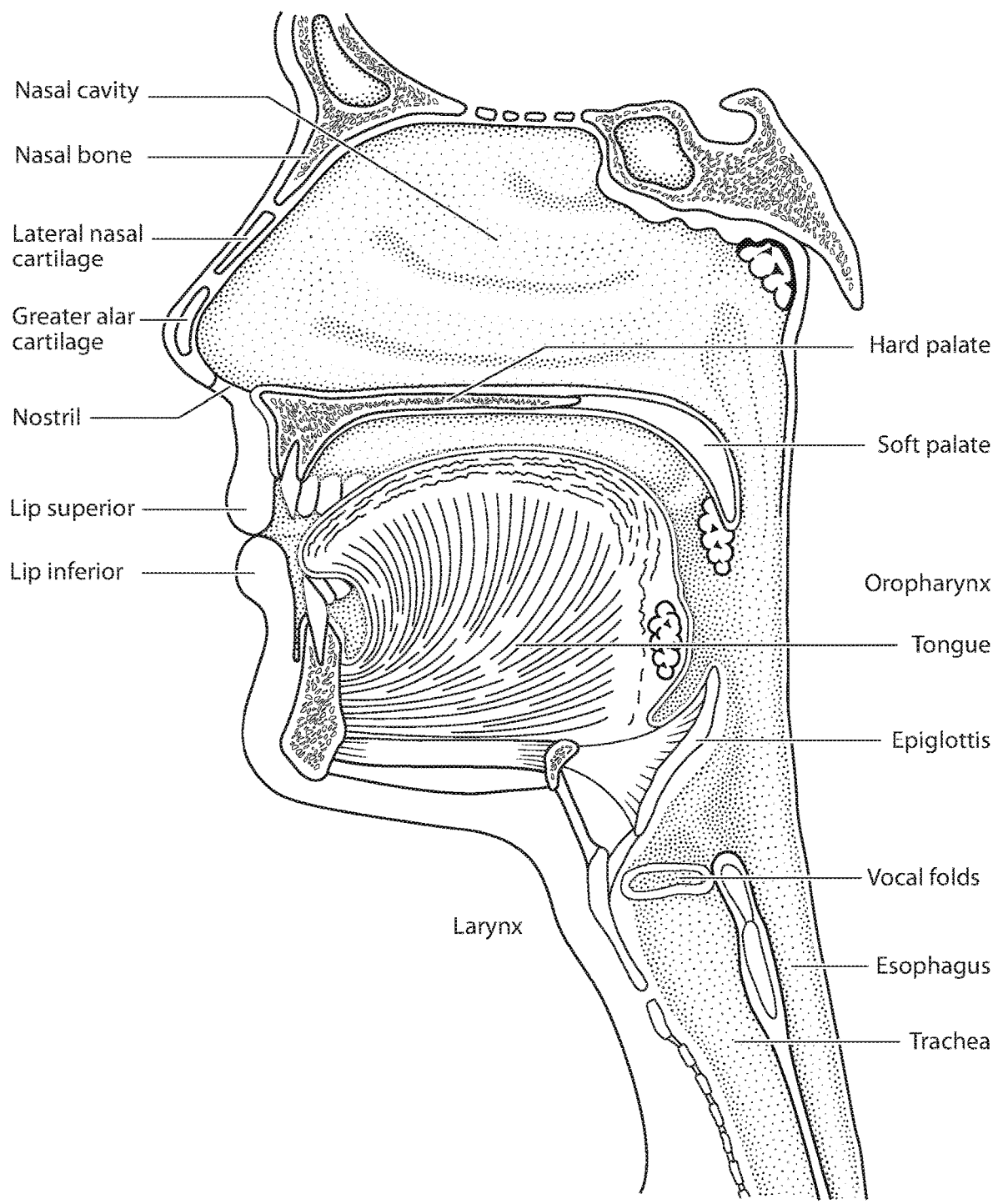
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
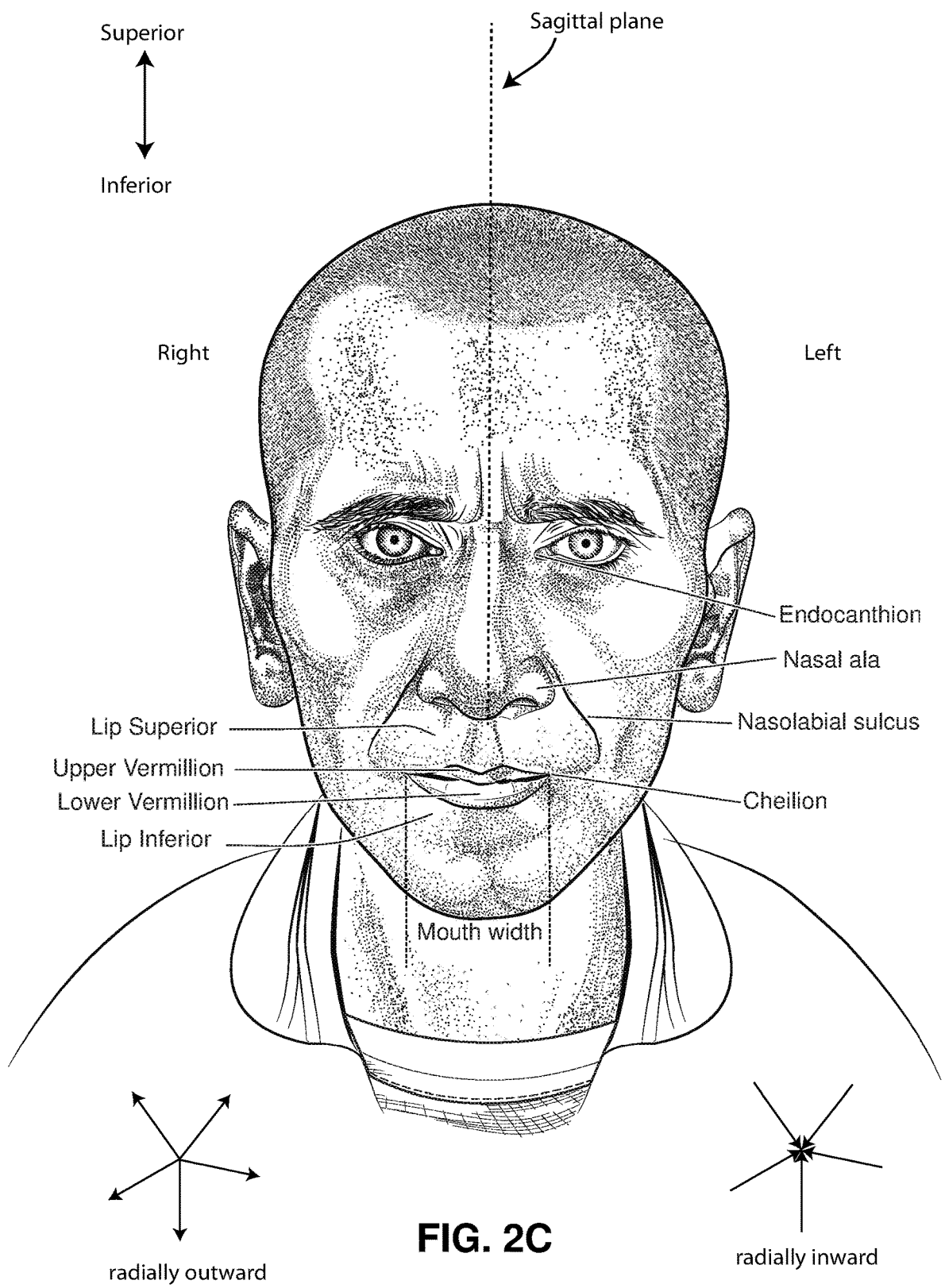
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
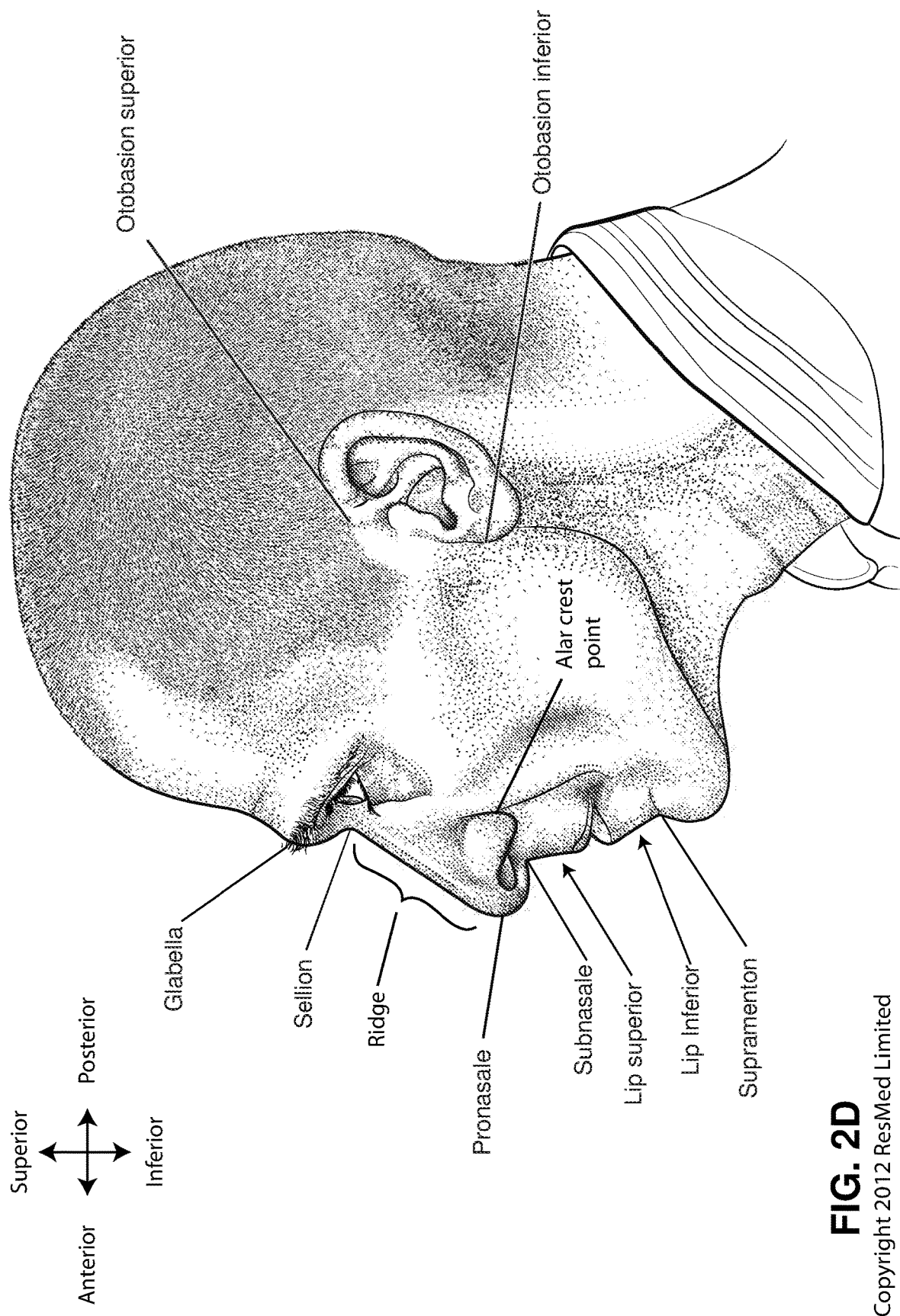
FIG. 2D is a side view of a head with several features of surface anatomy identified including glabella, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
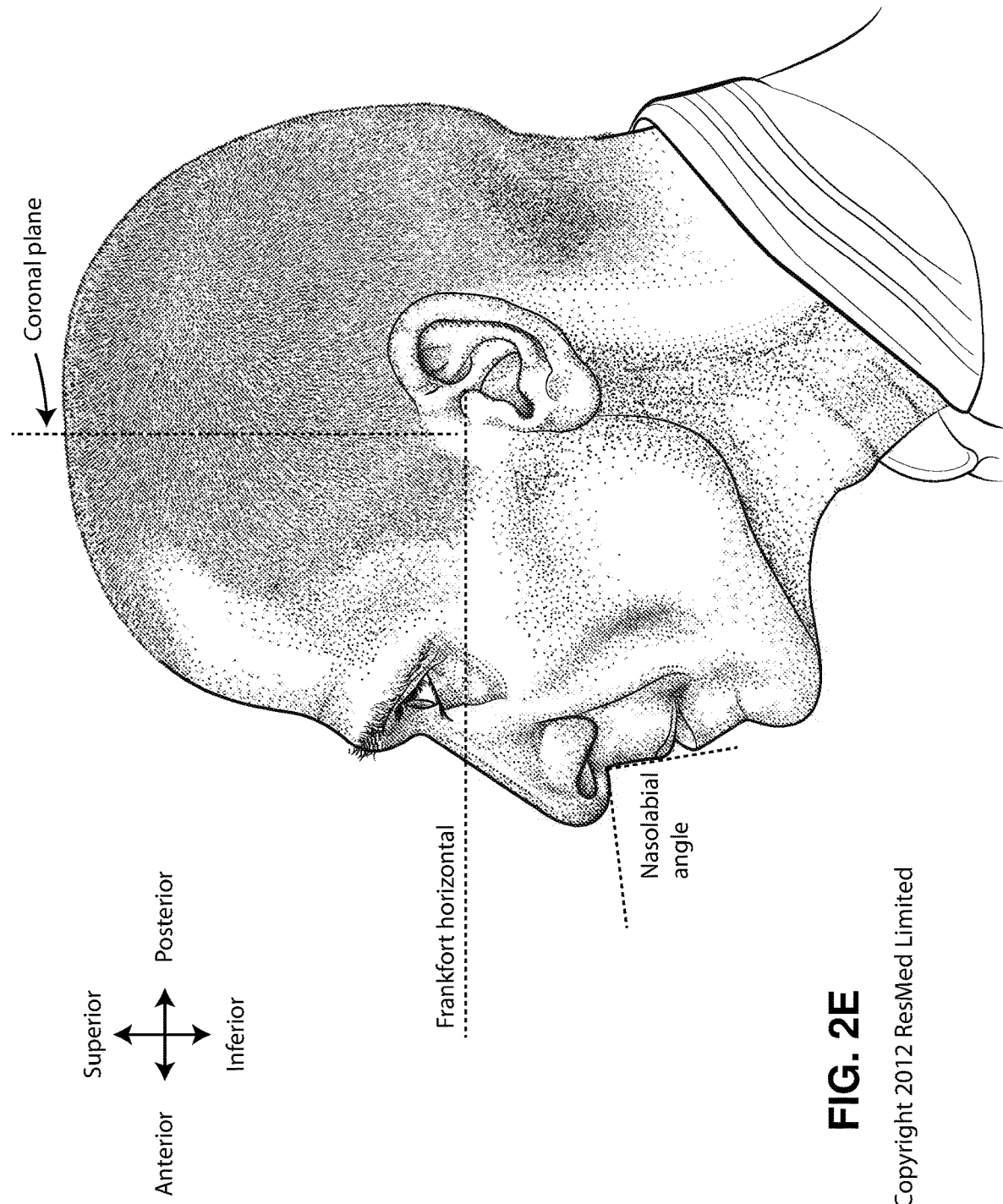

FIG. 2E is a further side view of a head. The approximate locations of the Frankfort horizontal and nasolabial angle are indicated. The coronal plane is also indicated.

Figure 2F:
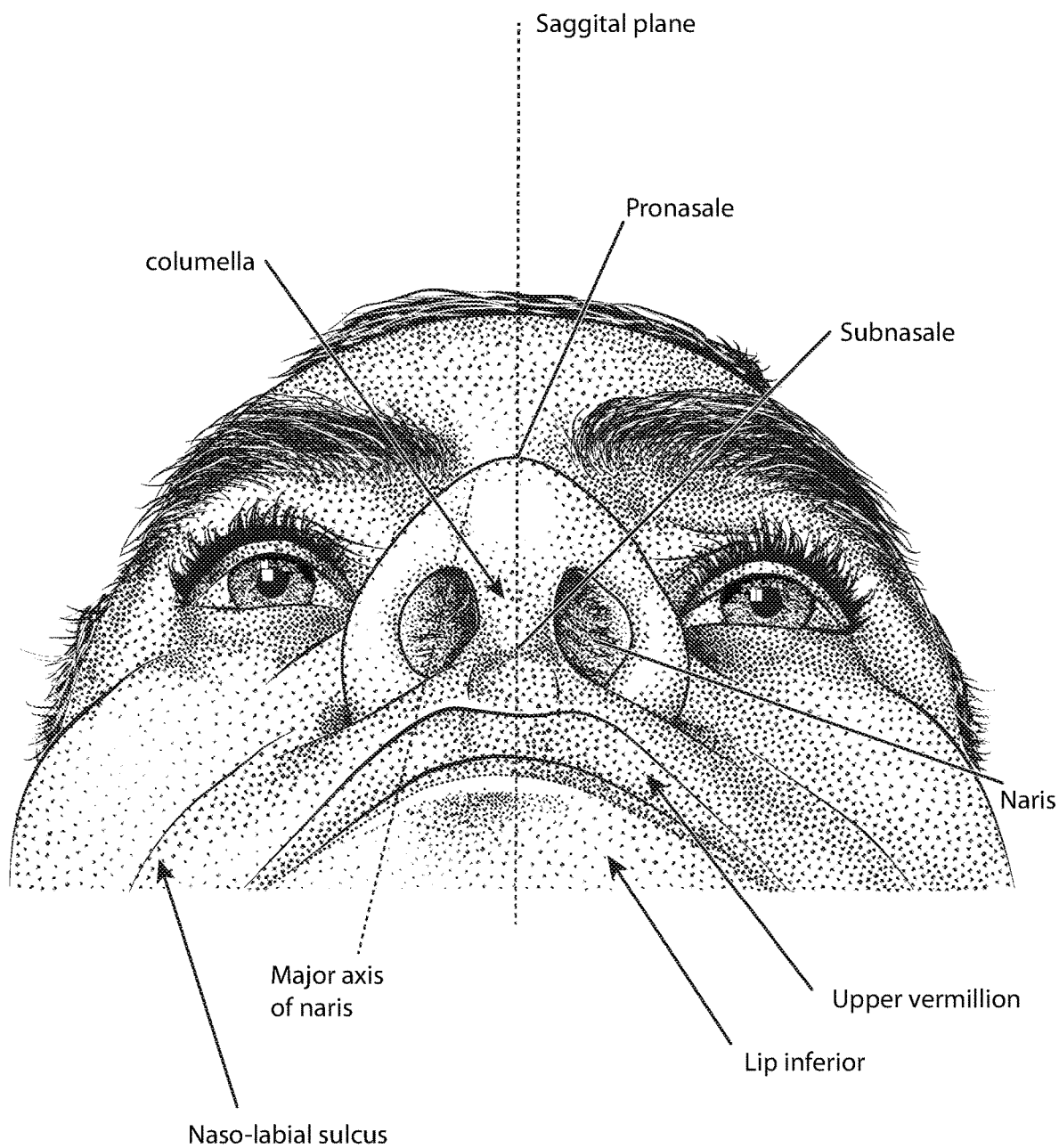

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
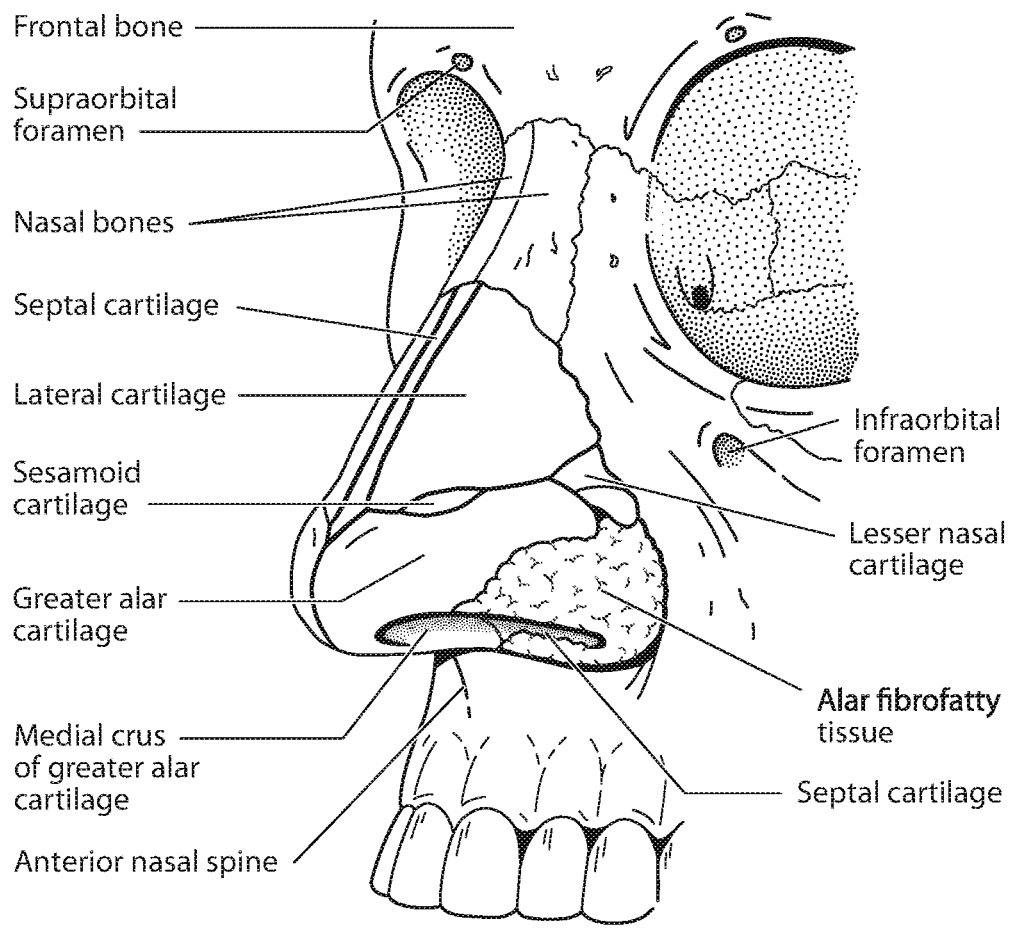

FIG. 2L shows an anterolateral view of a nose.

4.3 Patient Interface

Figure 3A:
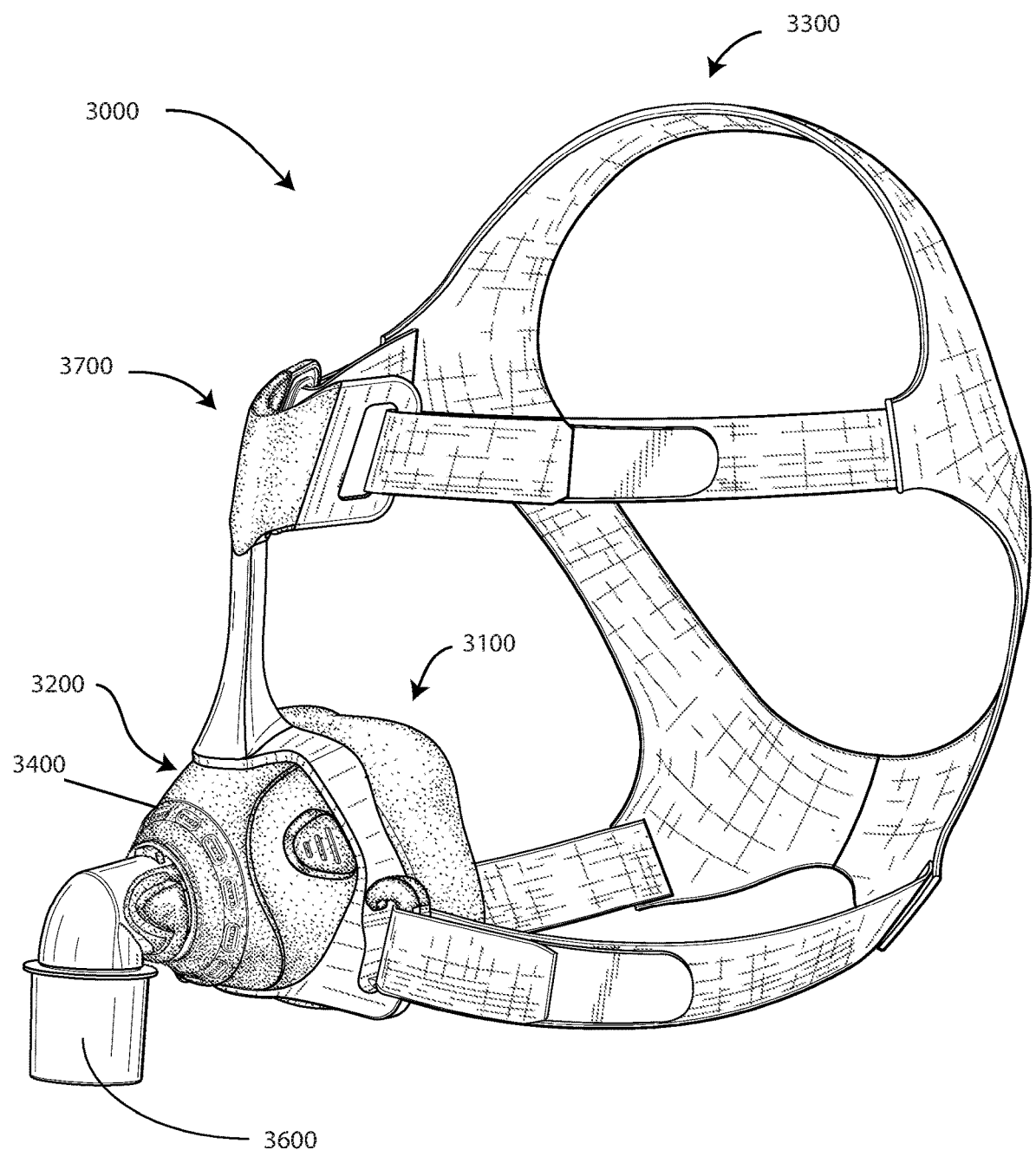

FIG. 3A shows a patient interface in the form of a nasal mask in accordance with one form of the present technology.

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

FIG. 3D shows a schematic of a cross-section through a structure at a point. An outward normal at the point is indicated. The curvature at the point has a value of zero.

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
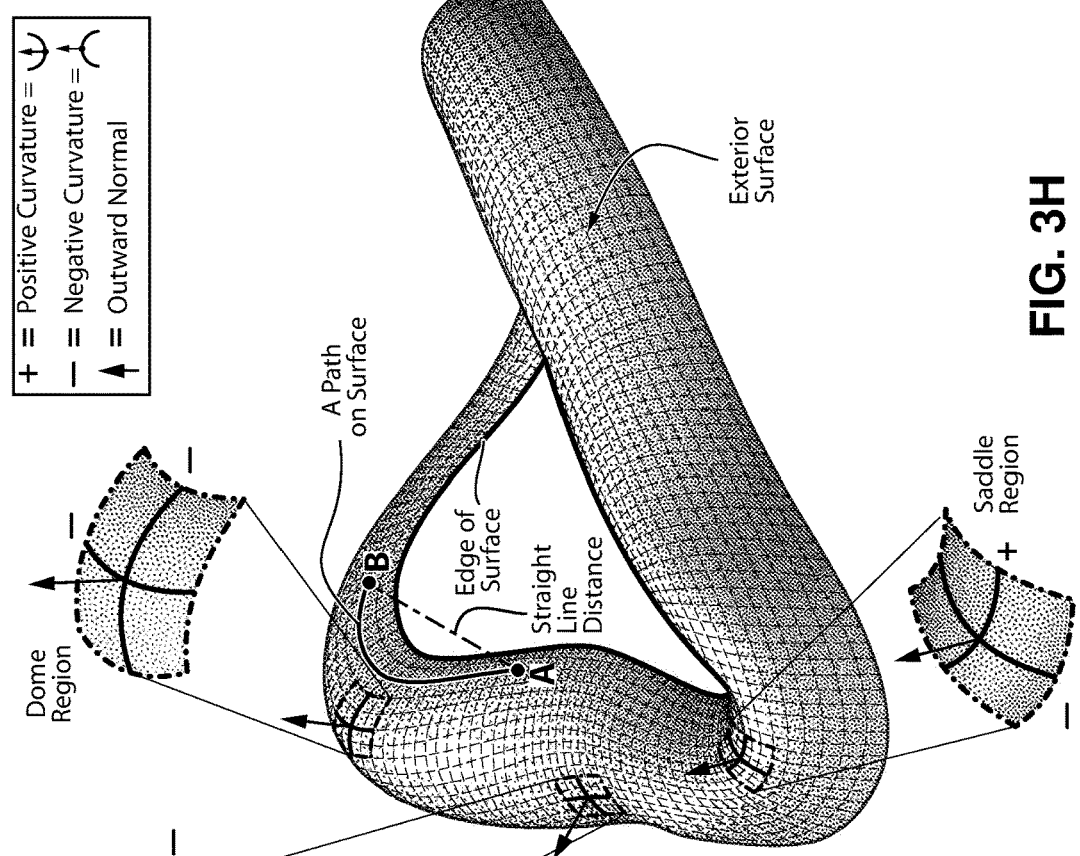
Figure 3G:
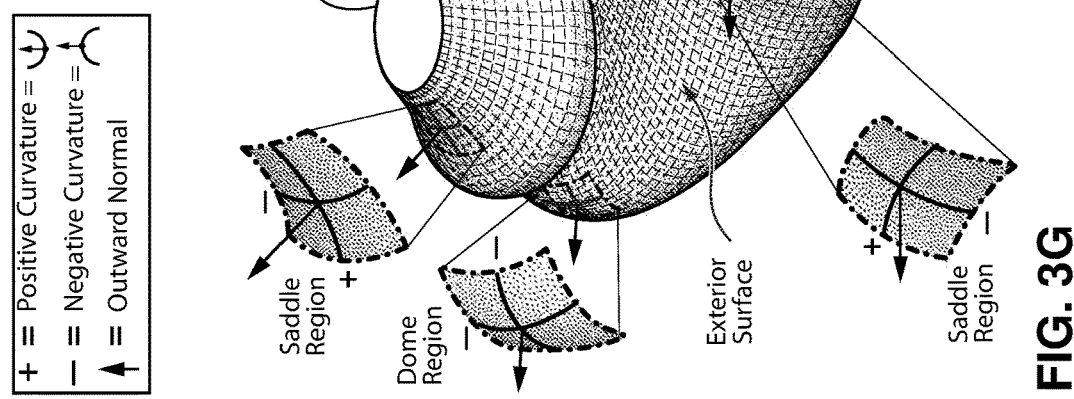

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

Figure 3O:
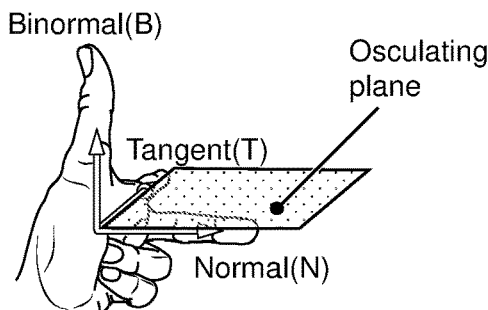

FIG. 3O illustrates a left-hand rule.

Figure 3P:
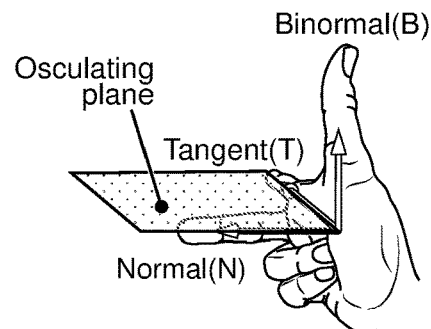

FIG. 3P illustrates a right-hand rule.

Figure 3Q:
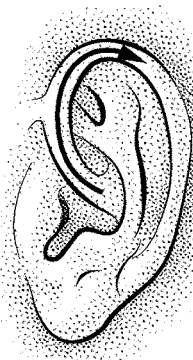

FIG. 3Q shows a left ear, including the left ear helix.

Figure 3S:
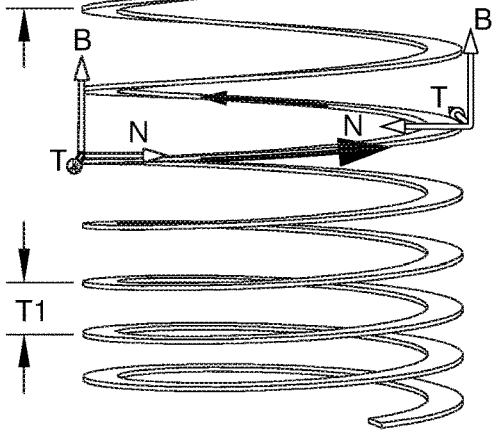
Figure 3R:
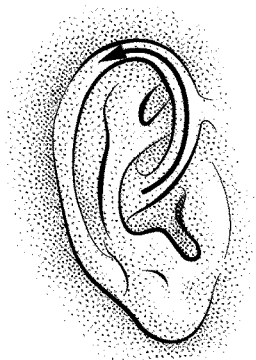

FIG. 3R shows a right ear, including the right ear helix.

FIG. 3S shows a right-hand helix.

Figure 3T:
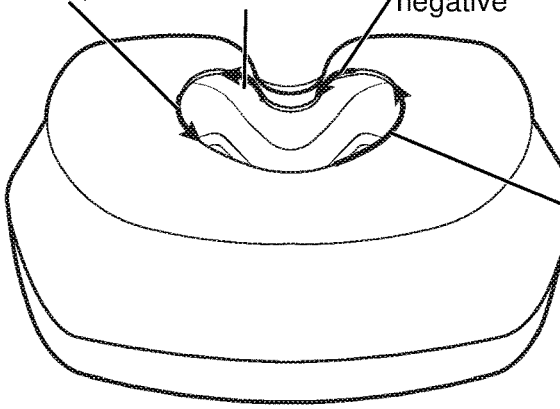

FIG. 3T shows a view of a mask, including the sign of the torsion of the space curve defined by the edge of the sealing membrane in different regions of the mask.

Figure 3U:
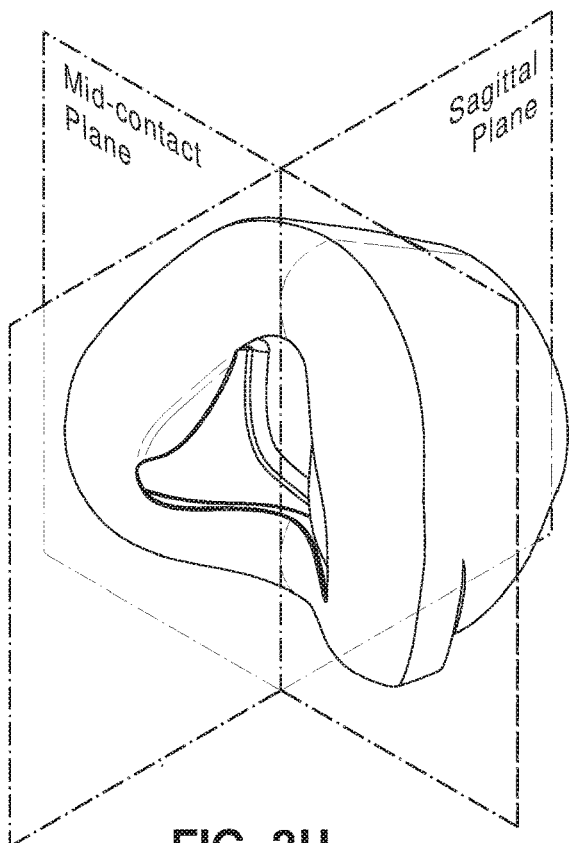

FIG. 3U shows a view of a plenum chamber 3200 showing a sagittal plane and a mid-contact plane.

Figure 3V:
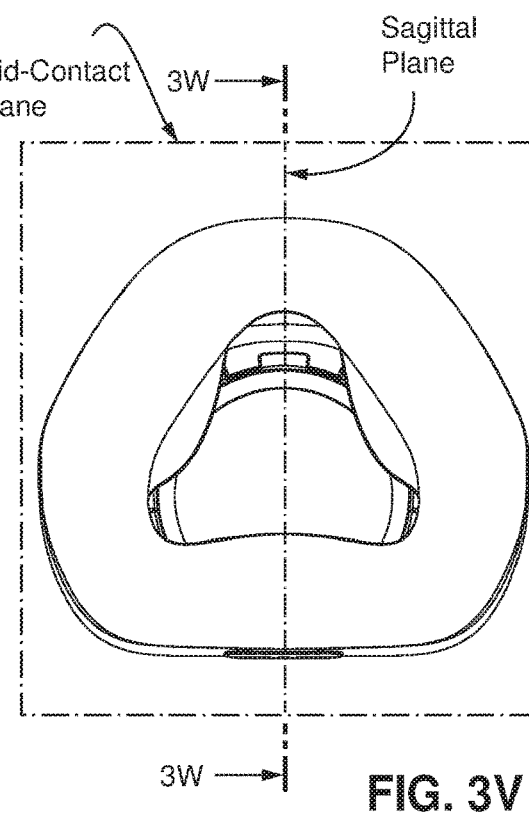

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
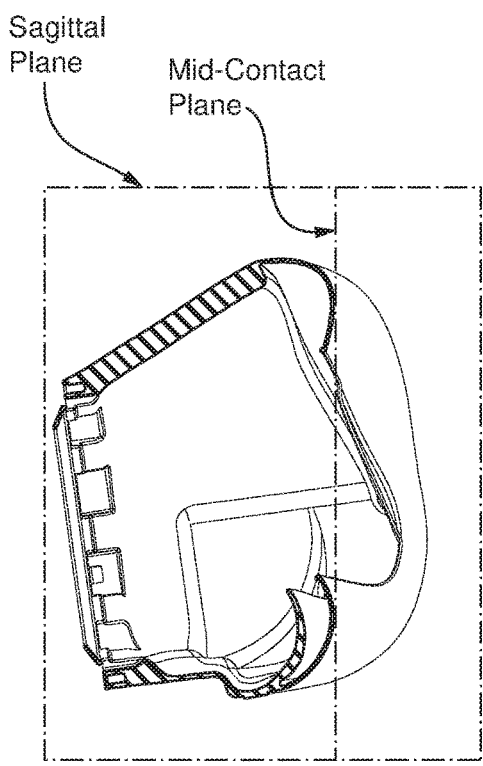

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord which lies on the sagittal plane and just touches the cushion of the plenum chamber at two points on the sagittal plane: a superior point and an inferior point. Depending on the geometry of the cushion in this region, the mid-contact plane may be a tangent at both the superior and inferior points.

Figure 3X:
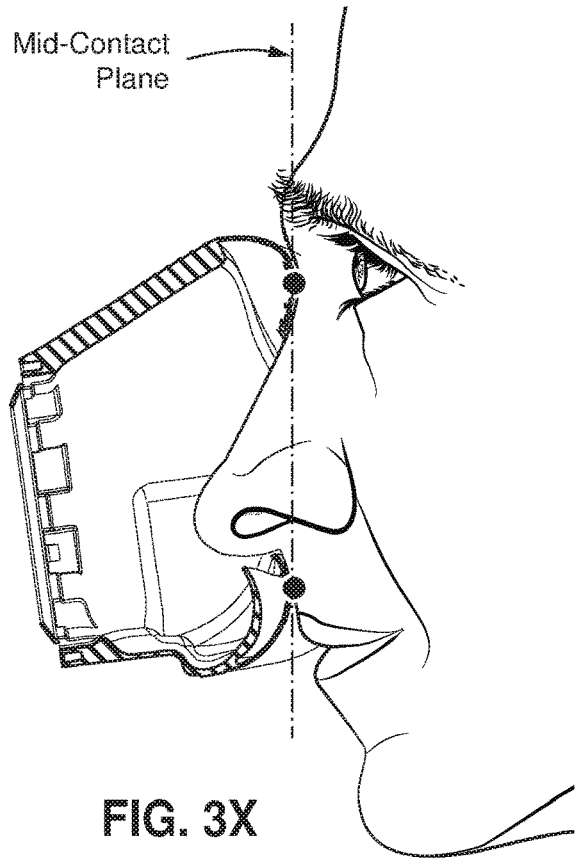

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point sits approximately on the sellion, while the inferior point sits on the lip superior.

4.4 RPT Device

Figure 4A:
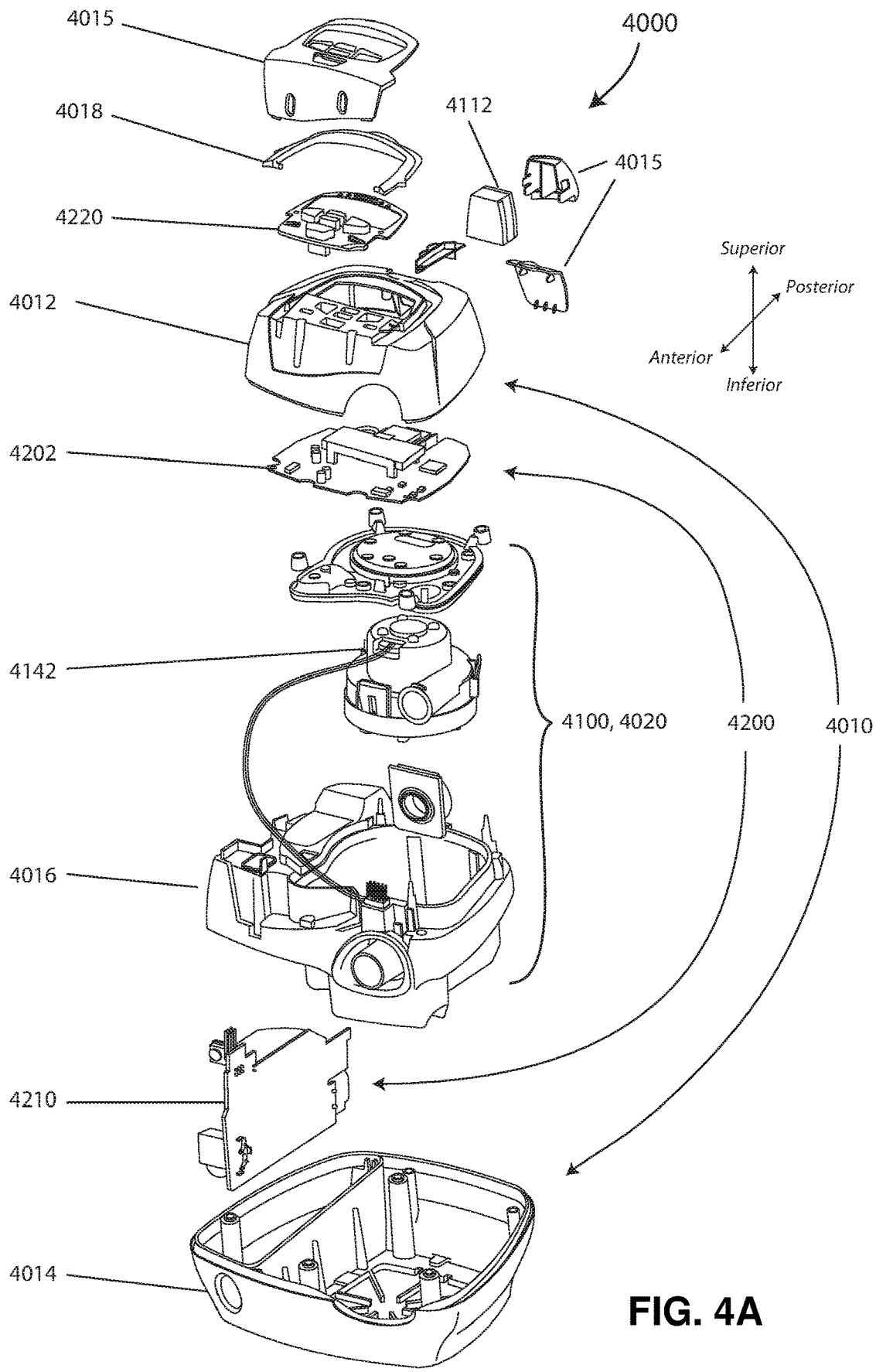

FIG. 4A shows an RPT device in accordance with one form of the present technology.

Figure 4B:
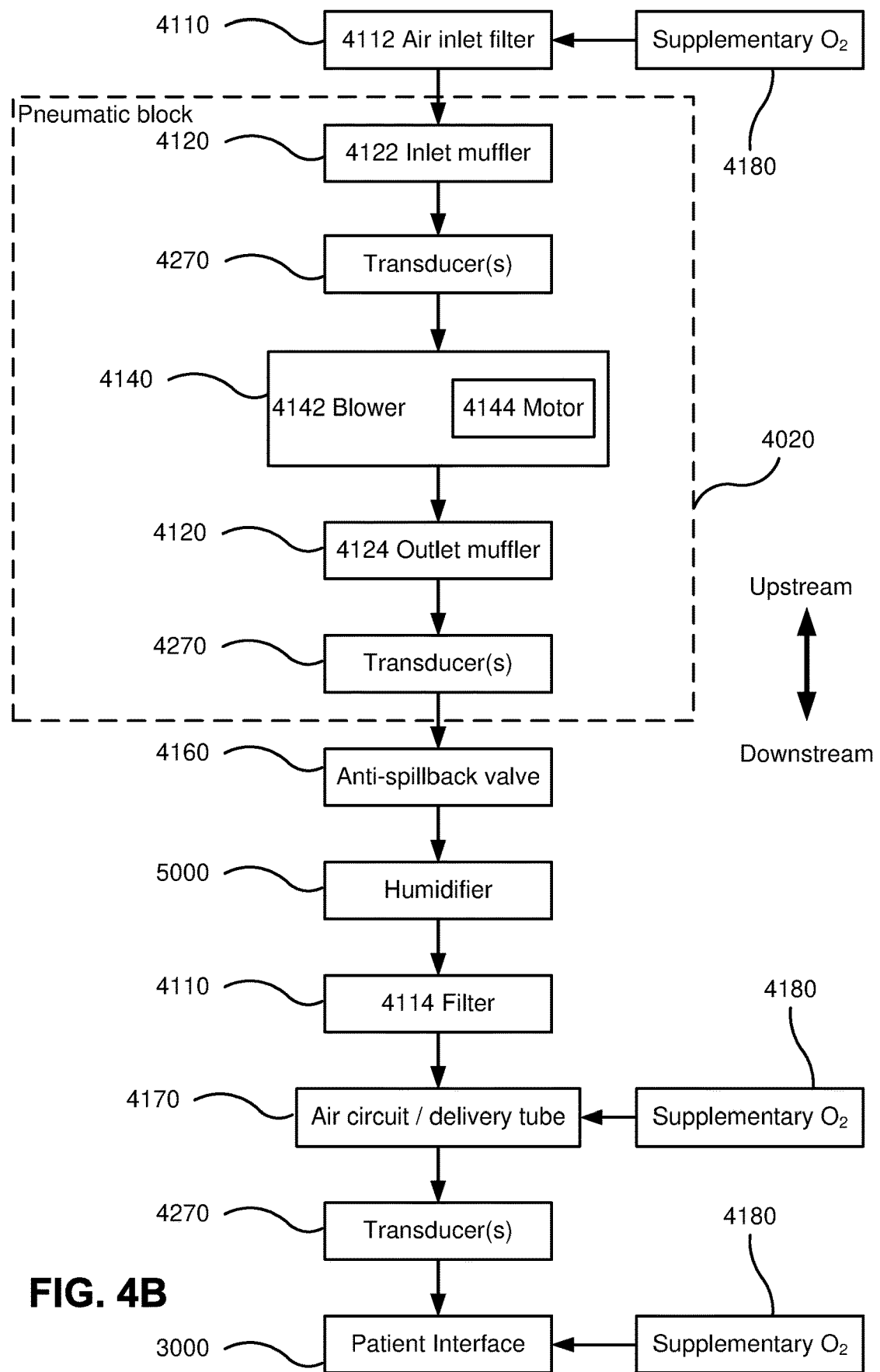

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

Figure 5A:
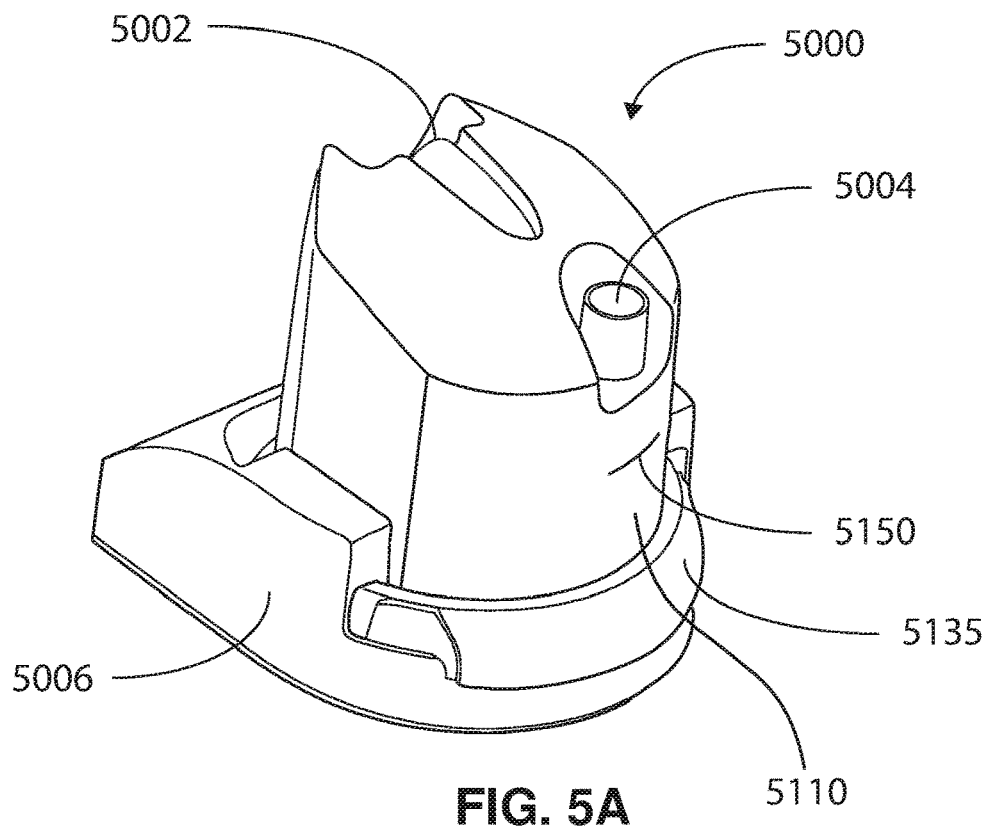

FIG. 5A shows an isometric view of a humidifier in accordance with one form of the present technology.

Figure 5B:
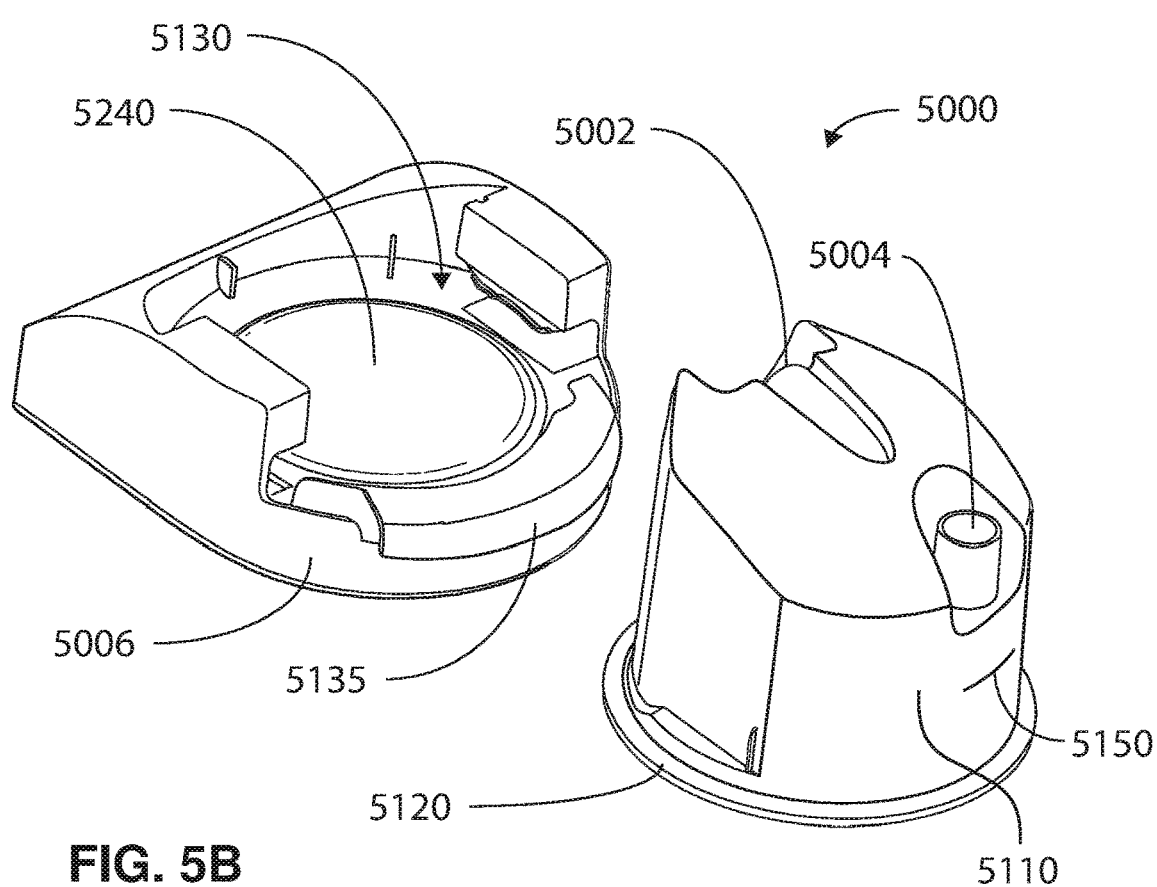

FIG. 5B shows an isometric view of a humidifier in accordance with one form of the present technology, showing a humidifier reservoir 5110 removed from the humidifier reservoir dock 5130.

4.6 Breathing Waveforms

Figure 6A:
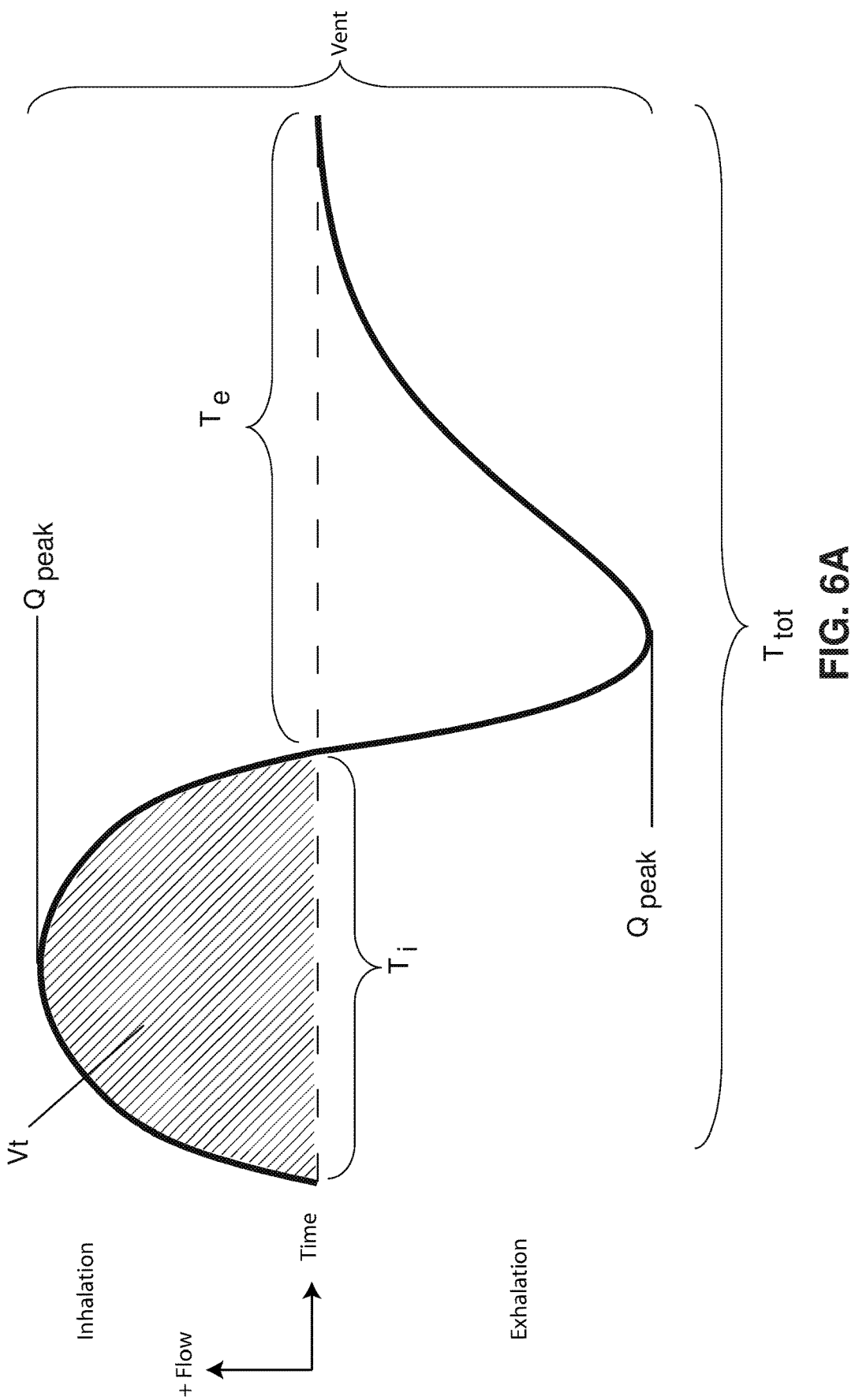

FIG. 6A shows a model typical breath waveform of a person while sleeping.

4.7 Screening, Diagnosis and Monitoring Systems

Figure 7A:
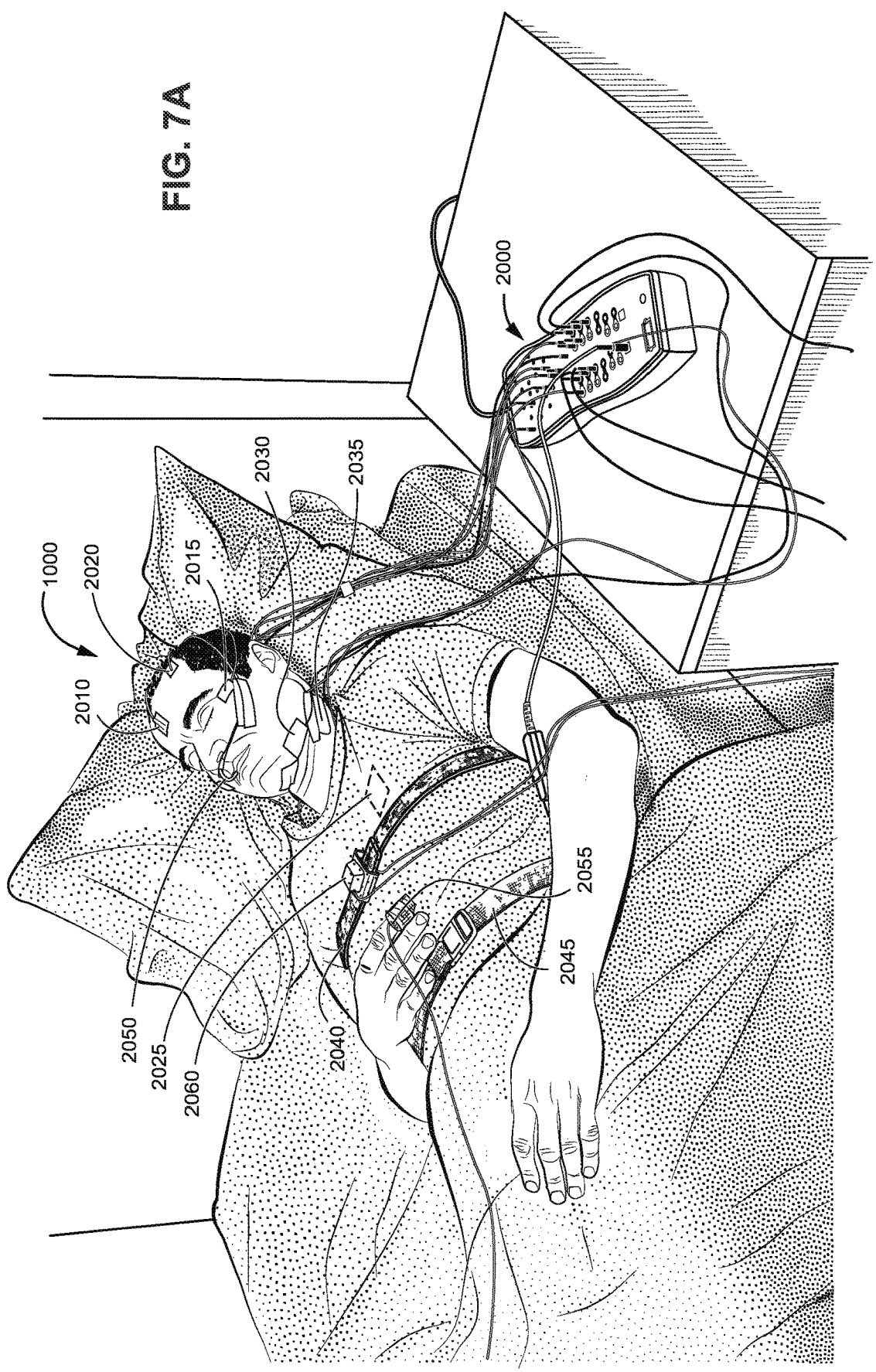

FIG. 7A shows a patient undergoing polysomnography (PSG). The patient is sleeping in a supine sleeping position.

Figure 7B:
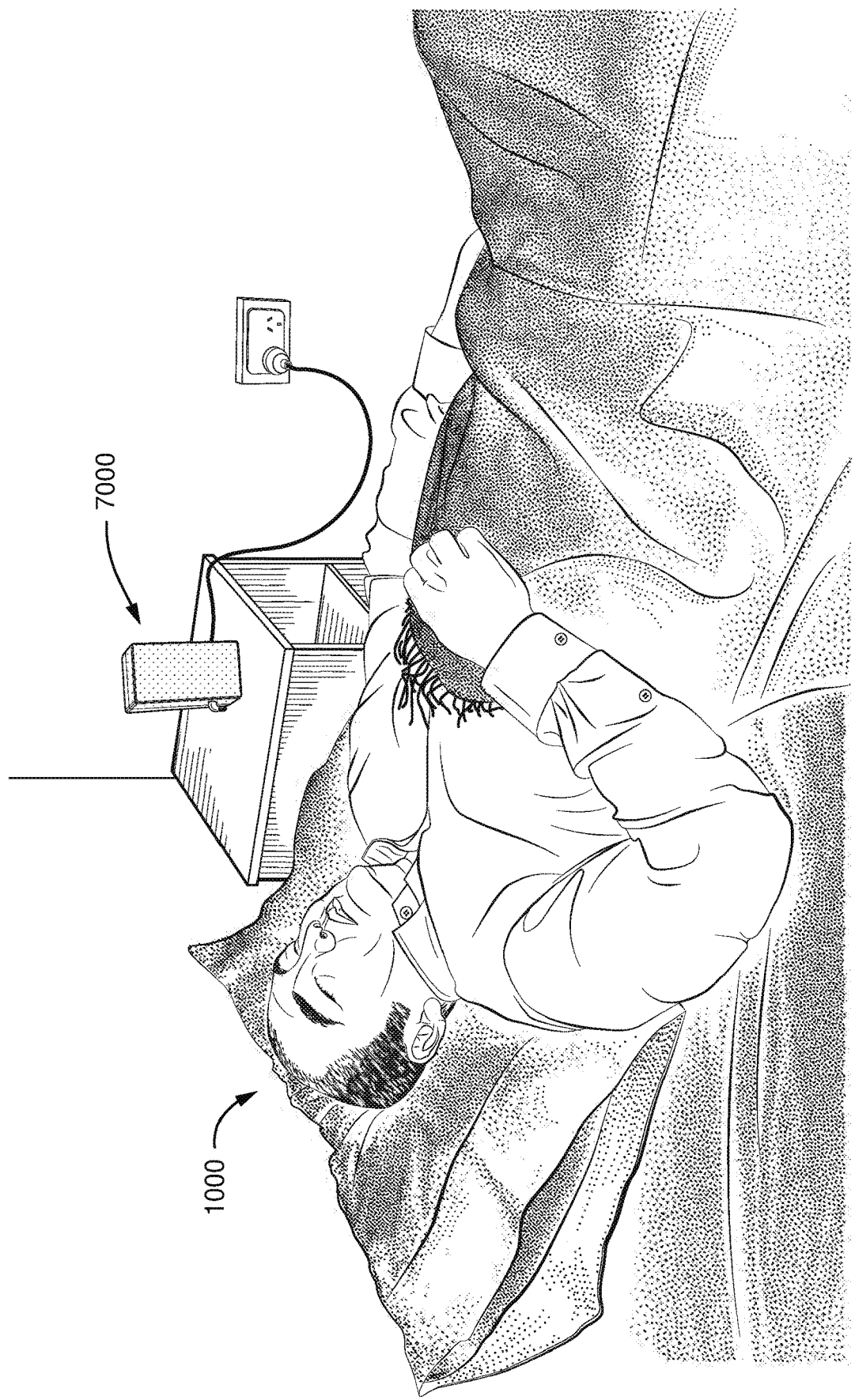

FIG. 7B shows a monitoring apparatus for monitoring the condition of a patient. The patient is sleeping in a supine sleeping position.

4.8 Particular Examples of the Present Technology

Figure 8A:
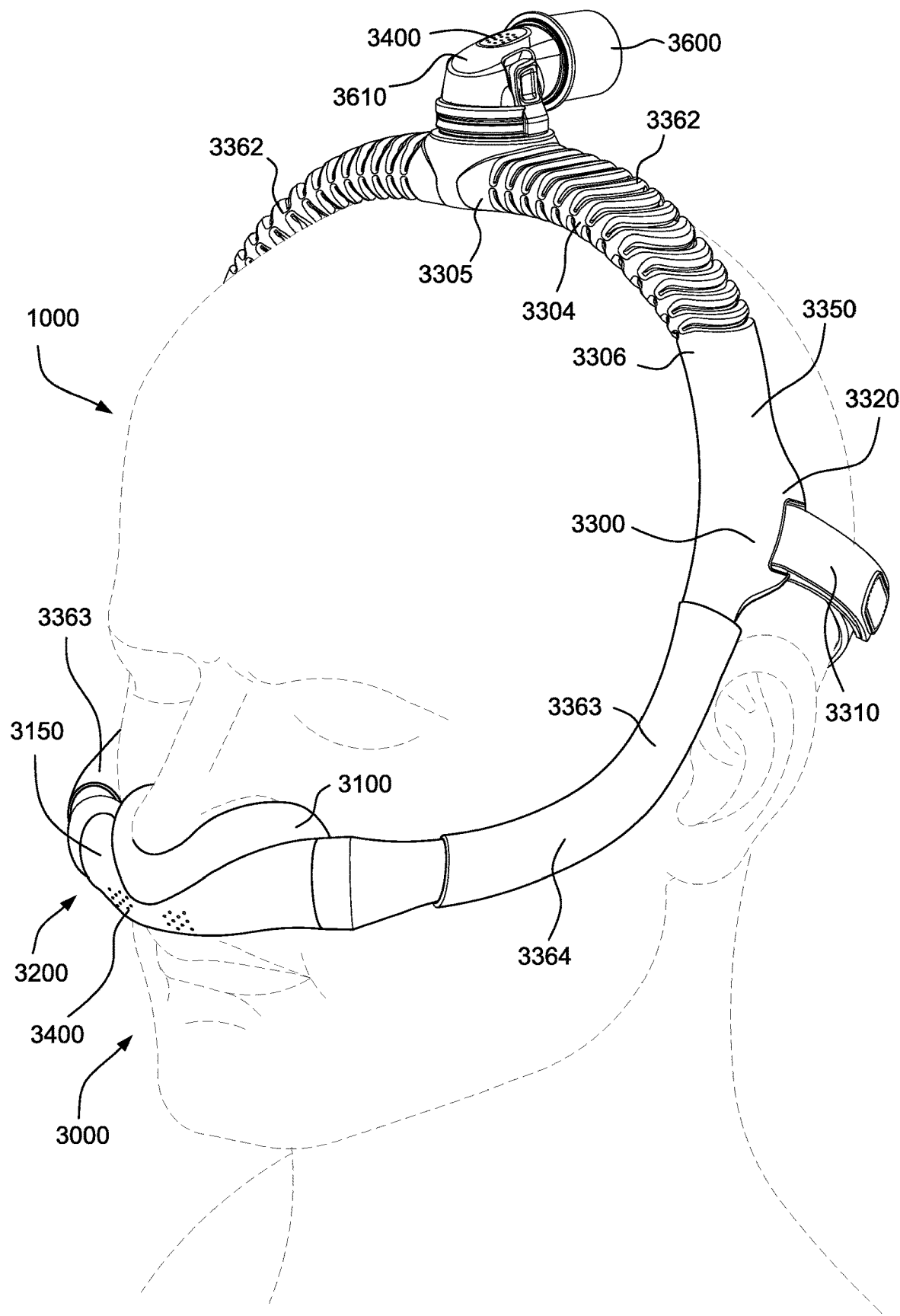

FIG. 8A is a perspective view illustration of a patient interface 3000 according to one example of the present technology while worn by a patient 1000.

Figure 8B:
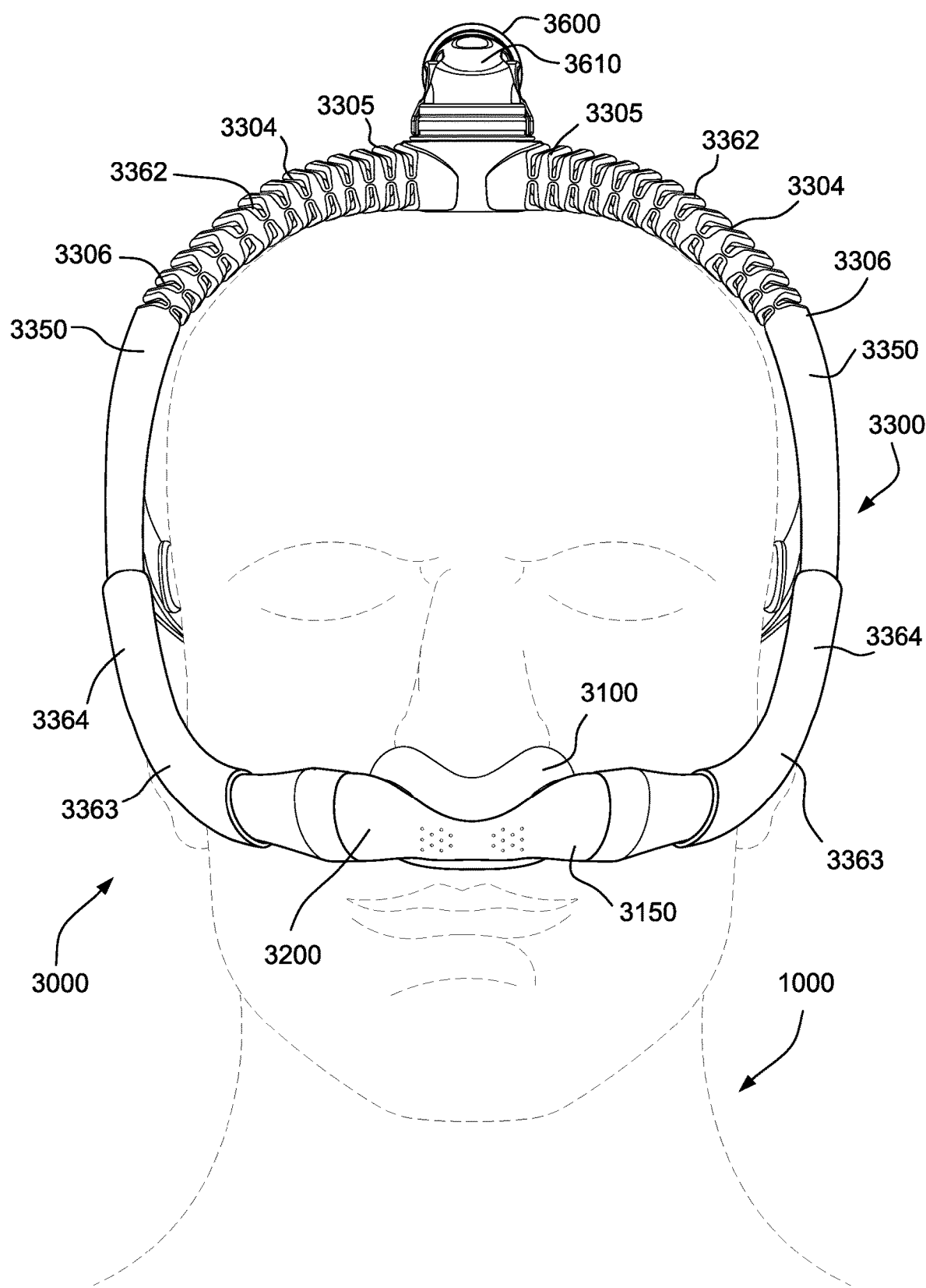

FIG. 8B is a front view illustration of the patient interface 3000 shown in FIG. 8A.

Figure 8C:
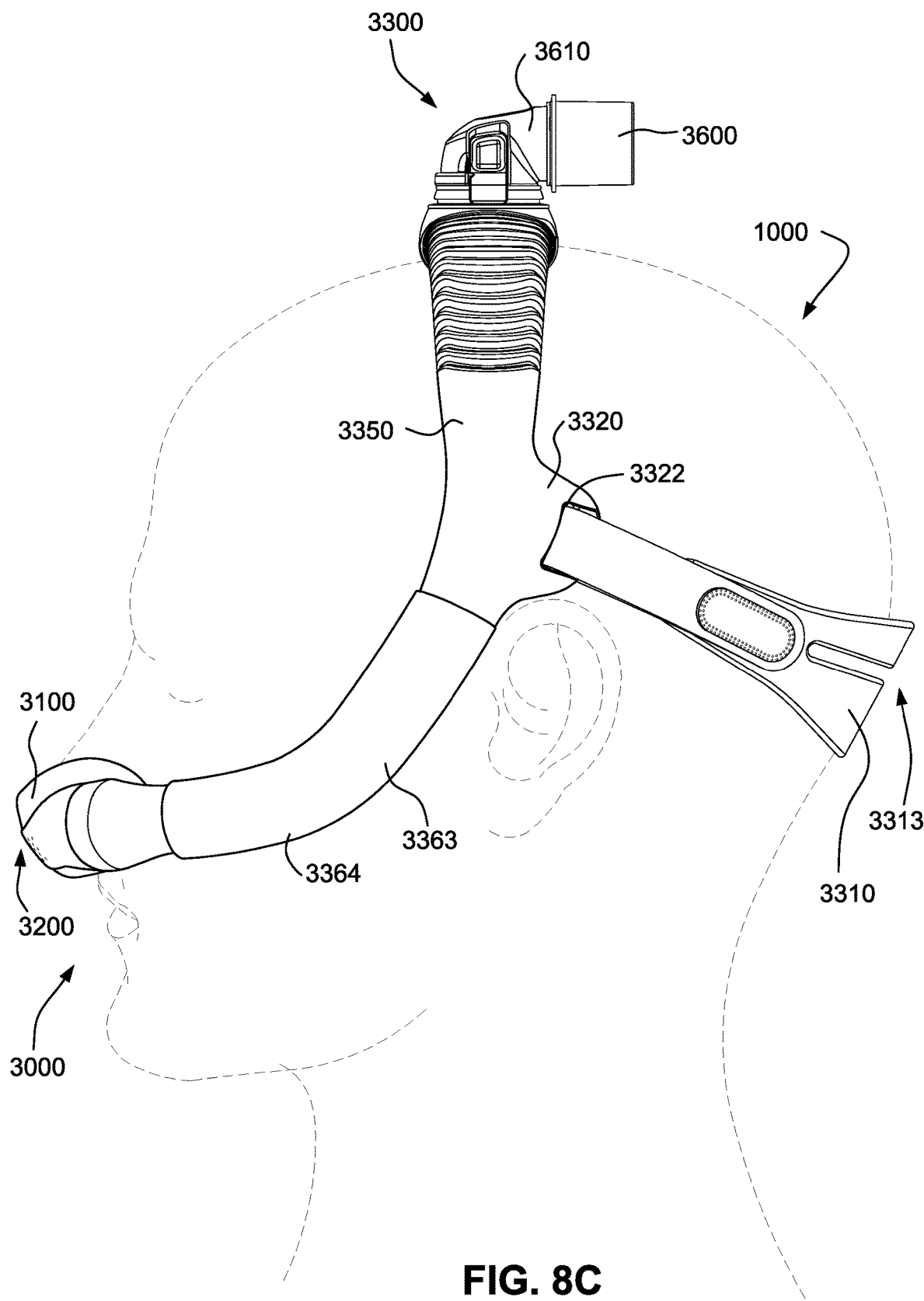

FIG. 8C is a side view illustration of the patient interface 3000 shown in FIG. 8A.

Figure 8D:
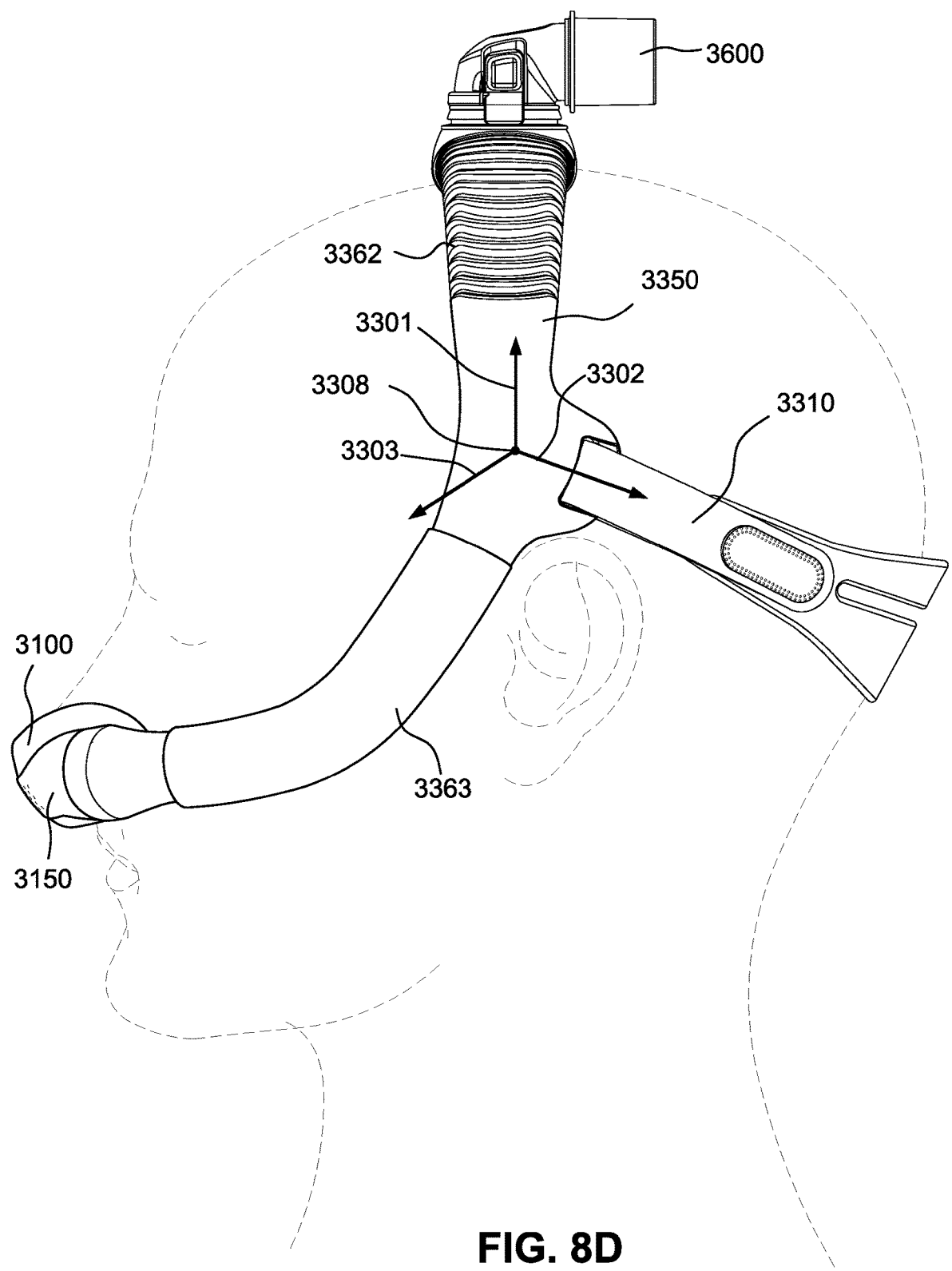

FIG. 8D is another side view illustration of the patient interface 3000 shown in FIG. 8A.

Figure 9A:
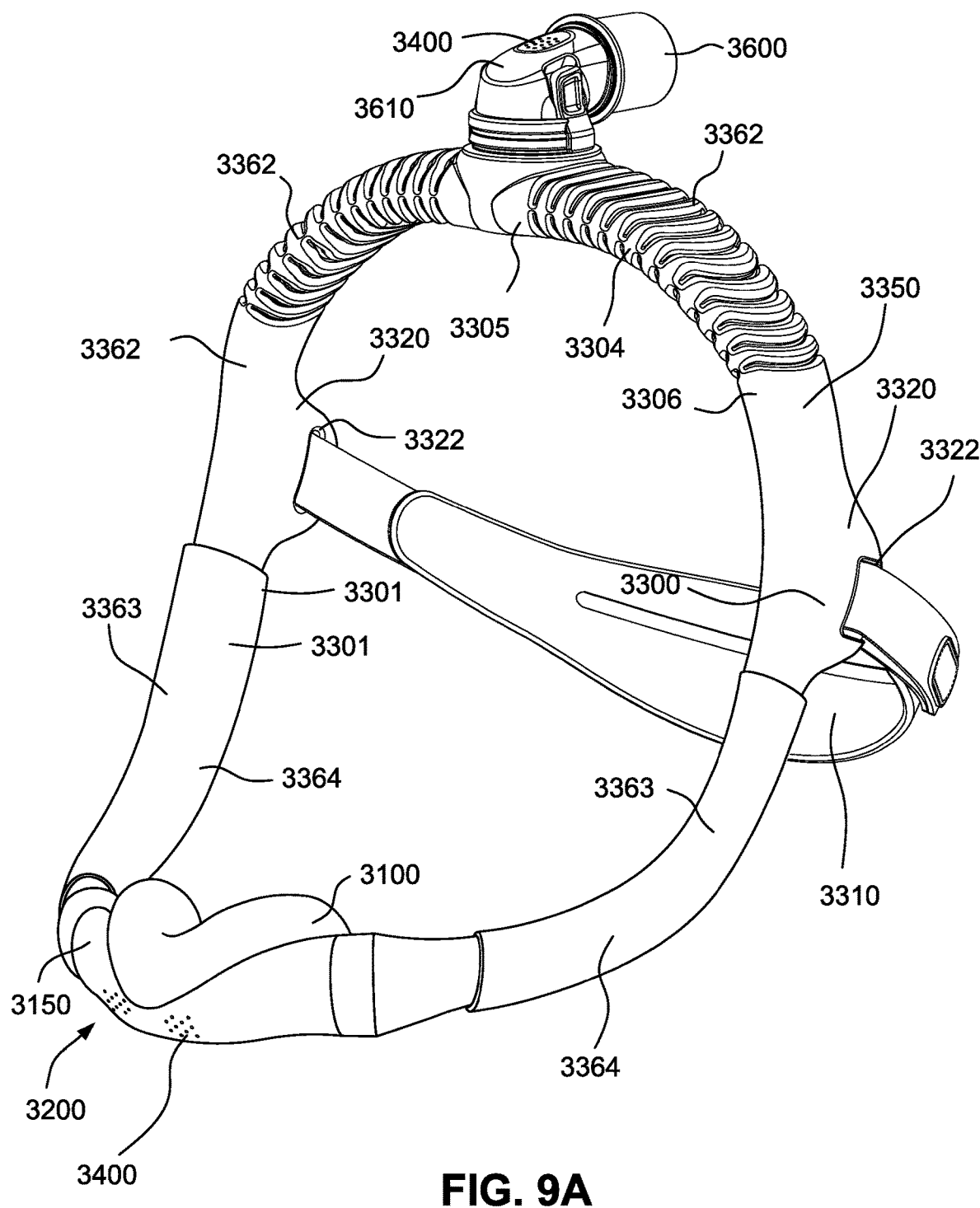

FIG. 9A is a perspective view illustration of the patient interface 3000 of FIG. 8A in isolation.

Figure 9B:
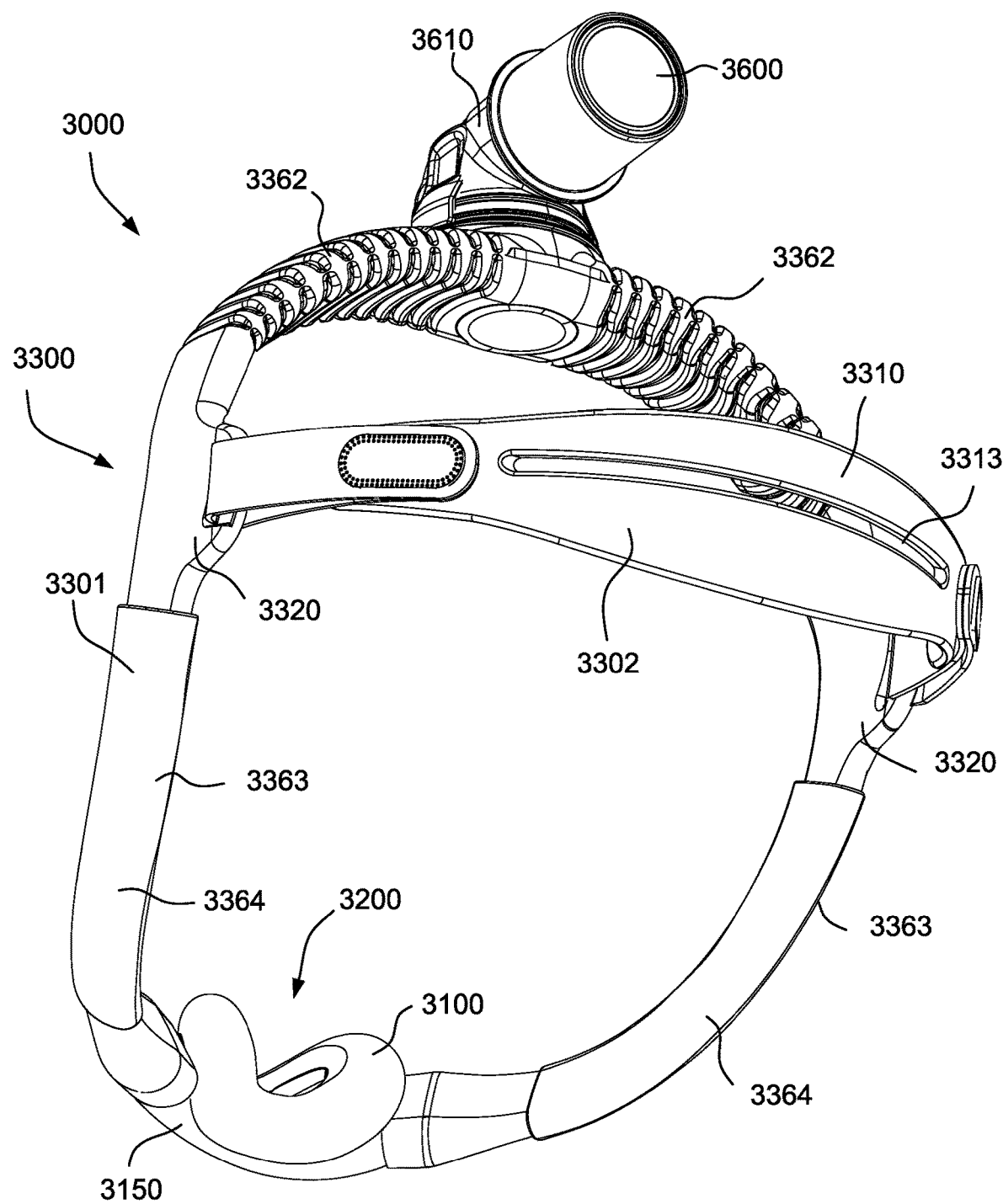

FIG. 9B is a rear perspective view illustration of the patient interface 3000 of FIG. 8A in isolation.

Figure 9C:
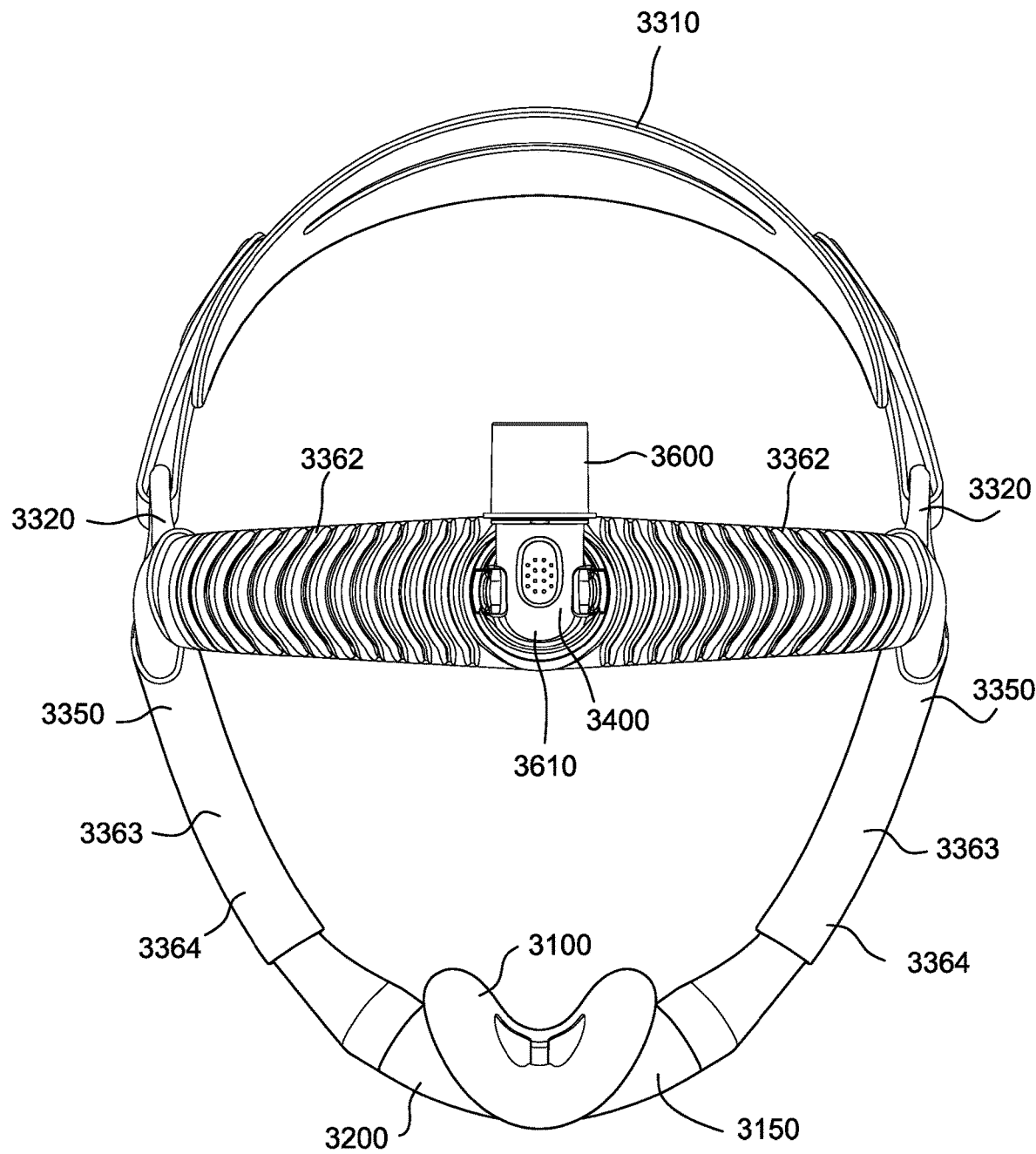

FIG. 9C is a top view illustration of the patient interface 3000 of FIG. 8A in isolation.

Figure 10A:
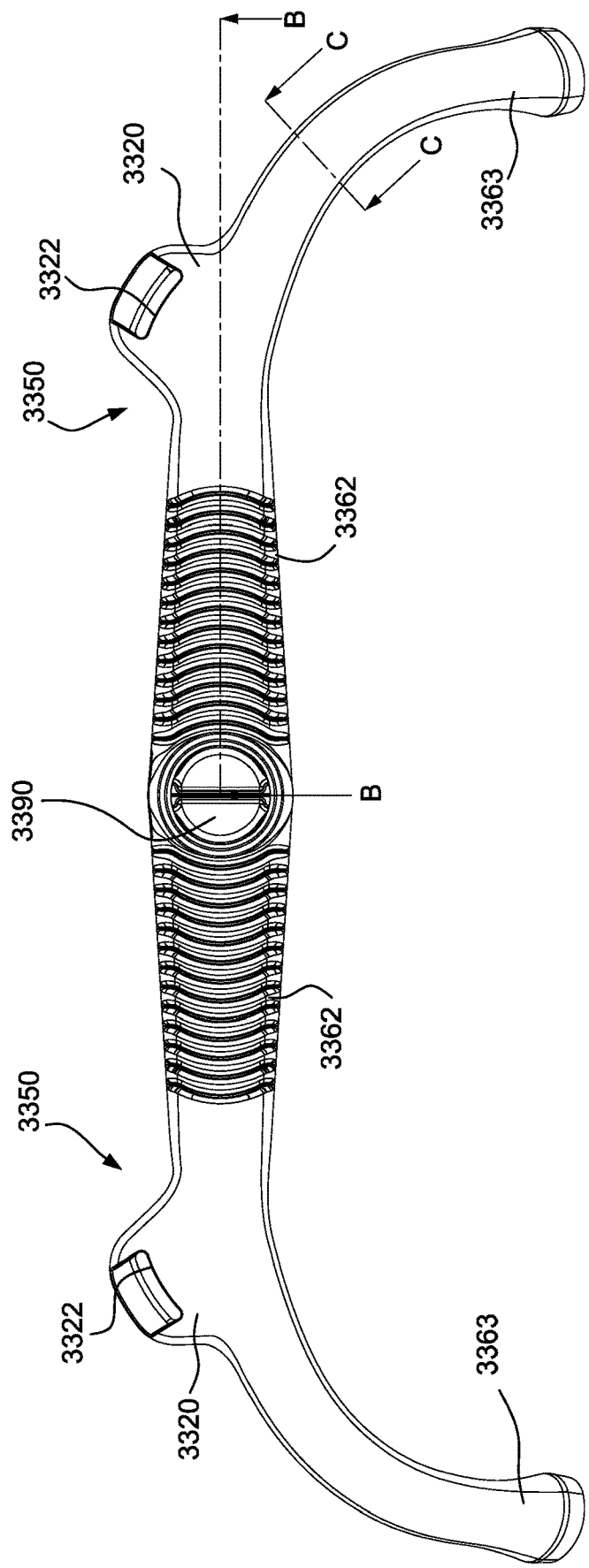

FIG. 10A shows a plan view of components of a positioning and stabilising structure 3300 according to one example of the present technology.

Figure 10B:
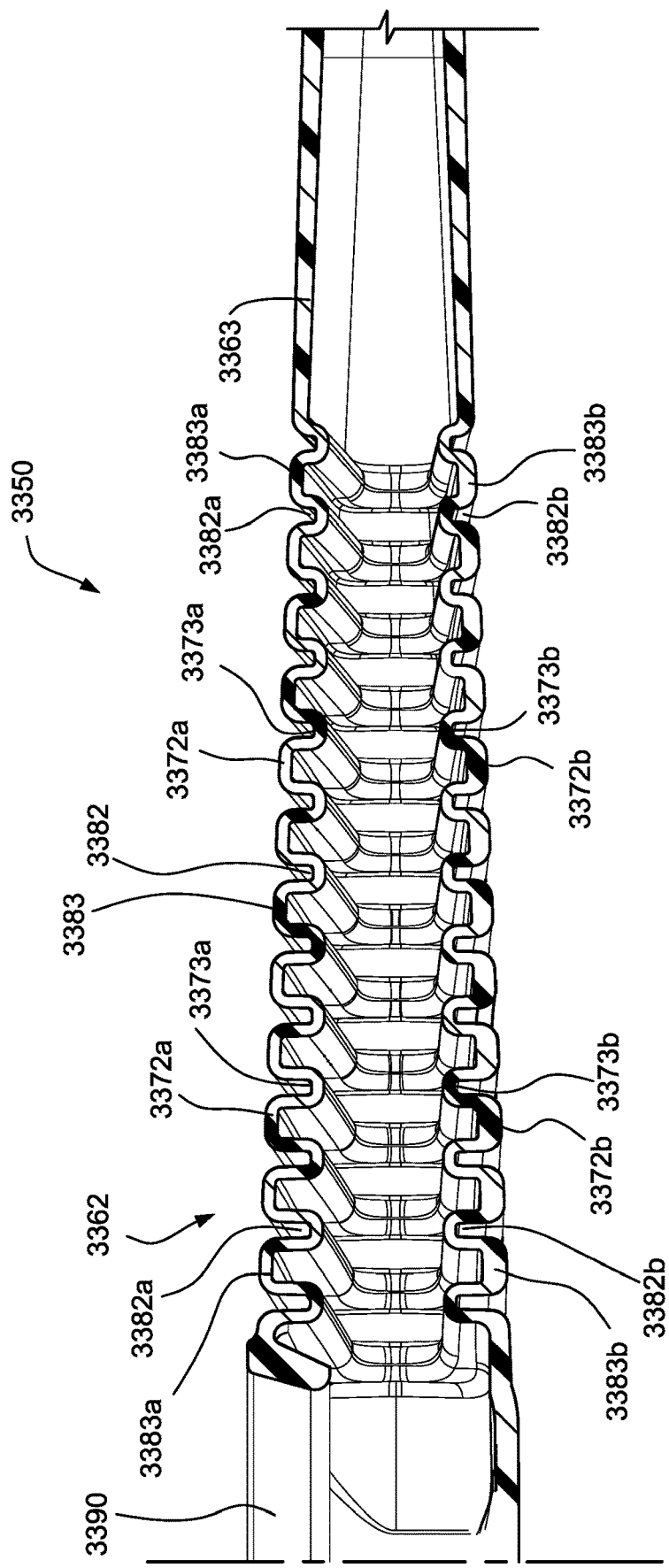

FIG. 10B shows a cross section view B-B of a portion of the positioning and stabilising structure 3300 of FIG. 10A.

Figure 10C:
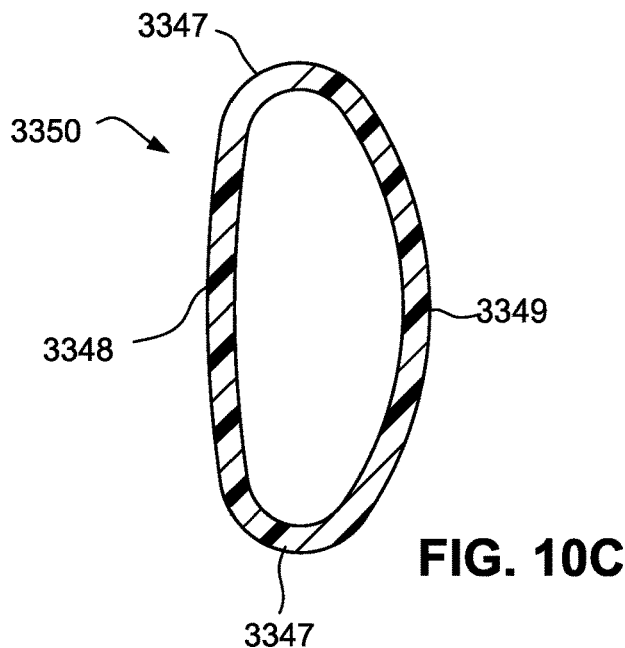

FIG. 10C shows a cross section view C-C of a non-extendable portion of the positioning and stabilising structure 3300 of FIG. 10A.

Figure 10D:
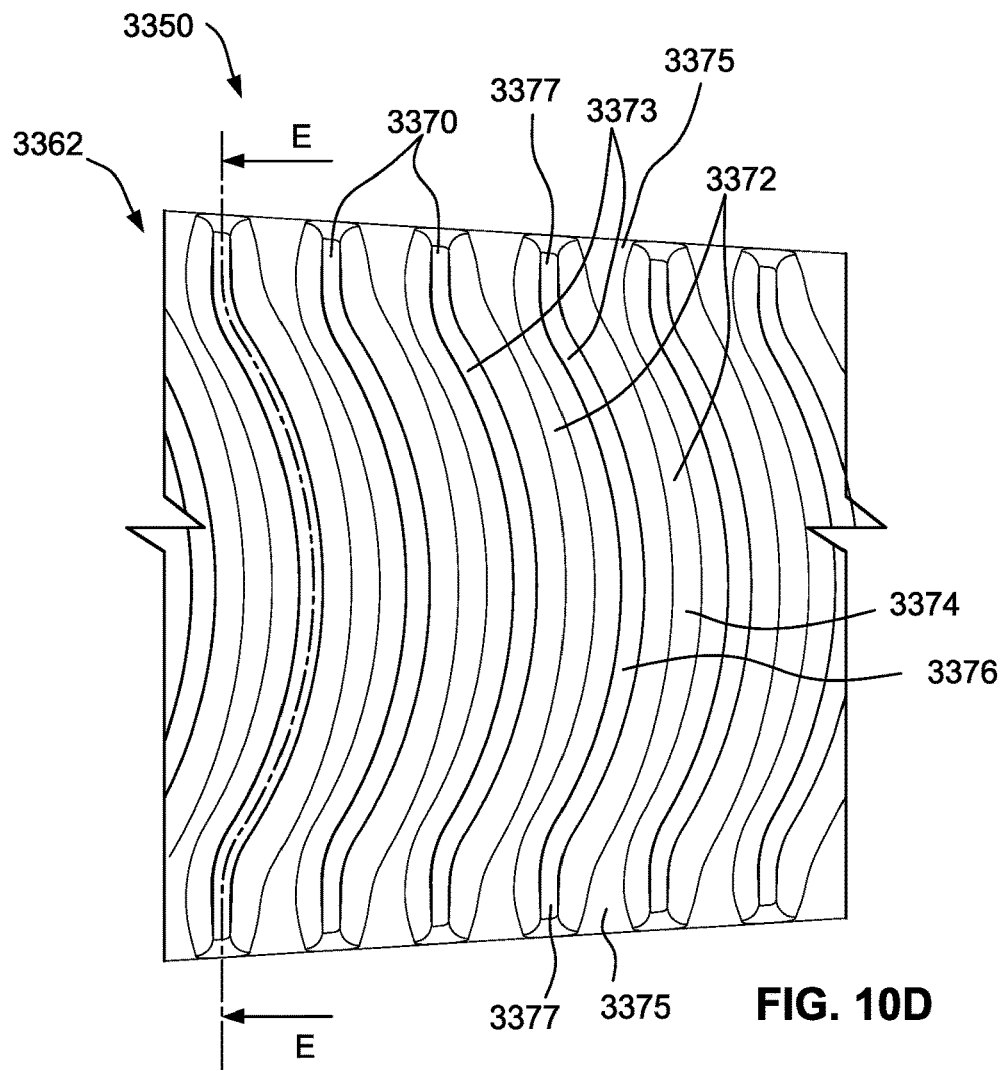

FIG. 10D shows a plan view of a portion of an extendable portion of the positioning and stabilising structure 3300 of FIG. 10A.

Figure 10E:
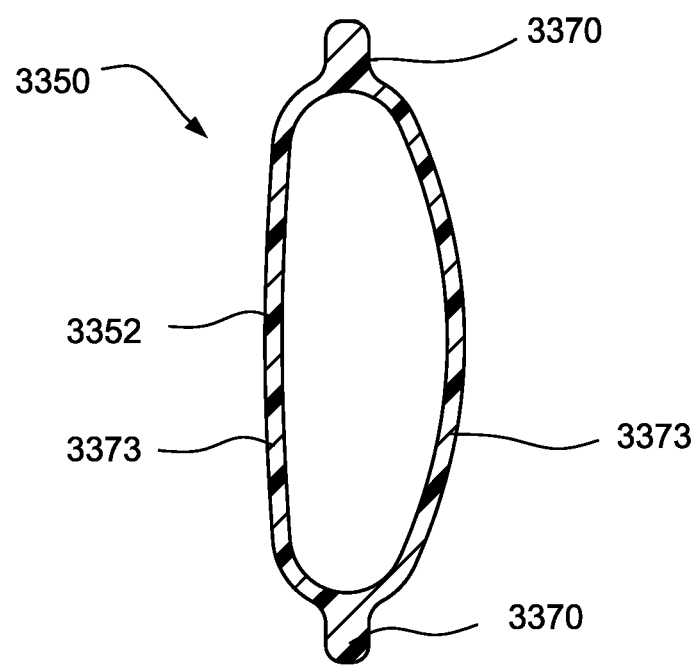

FIG. 10E shows a cross section view E-E of an extendable portion of the positioning and stabilising structure the 3300 of FIG. 10D.

Figure 10F:
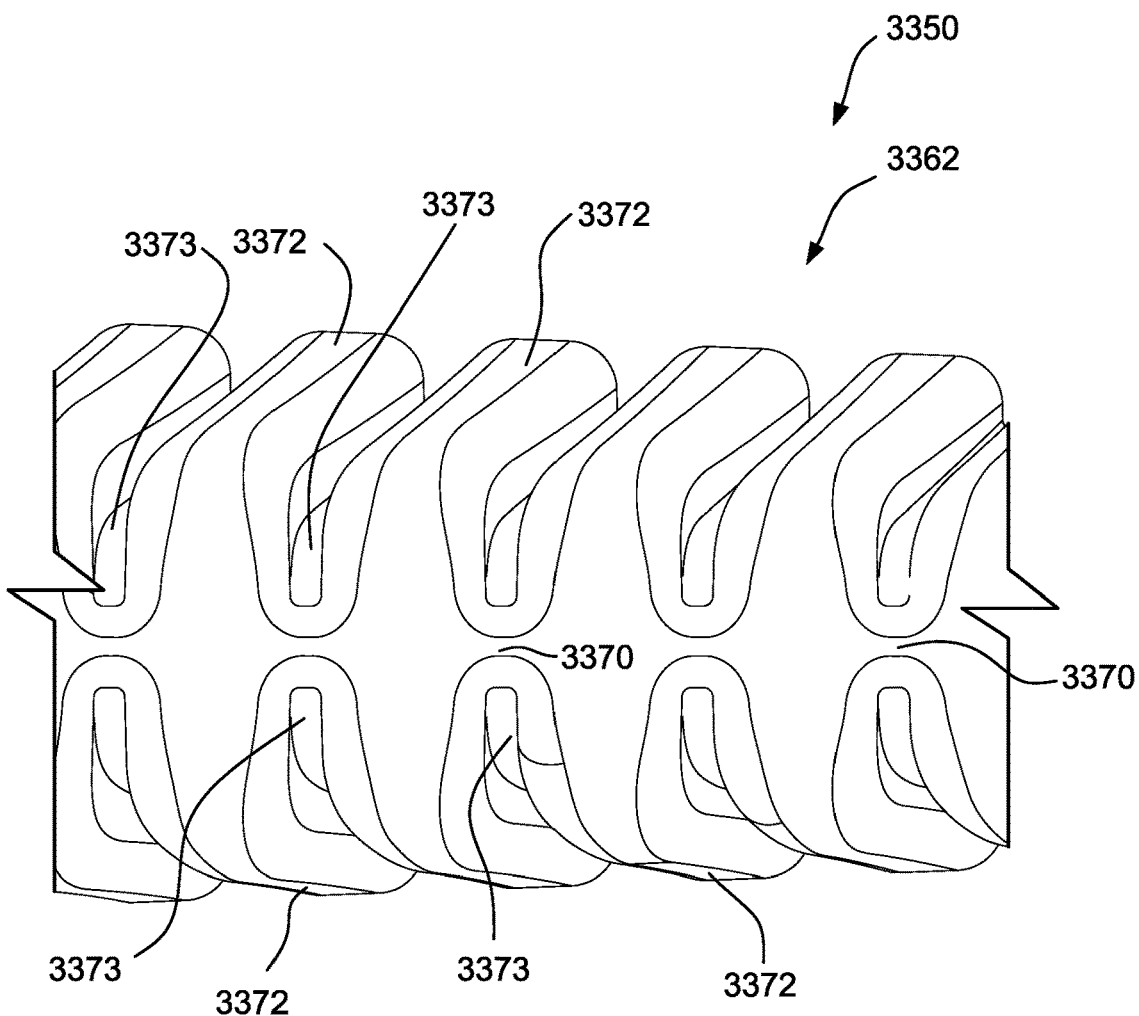

FIG. 10F shows a front view of a portion of an extendable portion of the positioning and stabling structure 3300 of FIG. 10A.

Figure 10G:
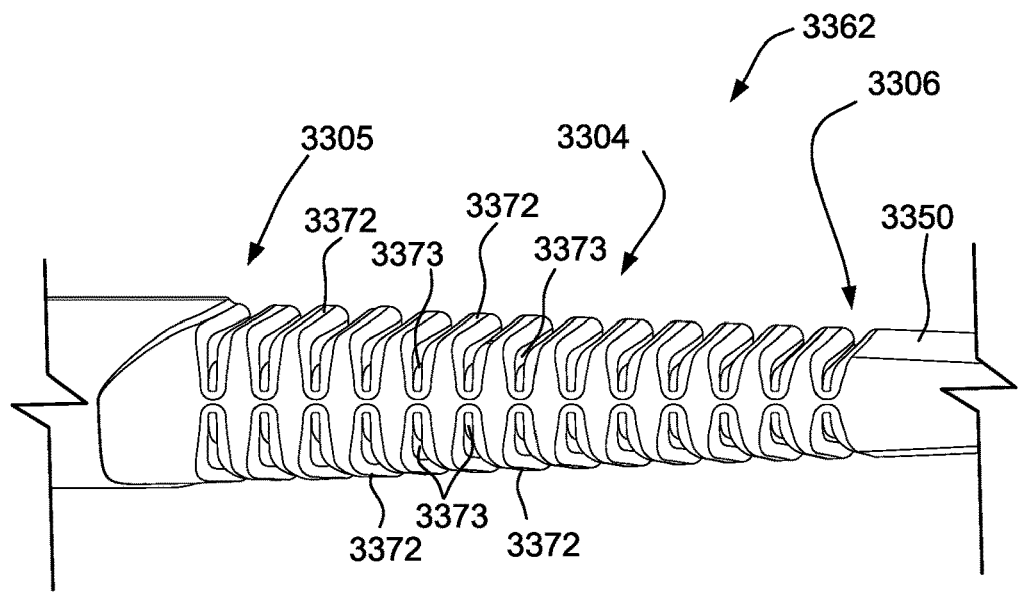

FIG. 10G shows a front view of an extendable portion of the positioning and stabilising structure 3300 of FIG. 10A in a straightened configuration.

Figure 10H:
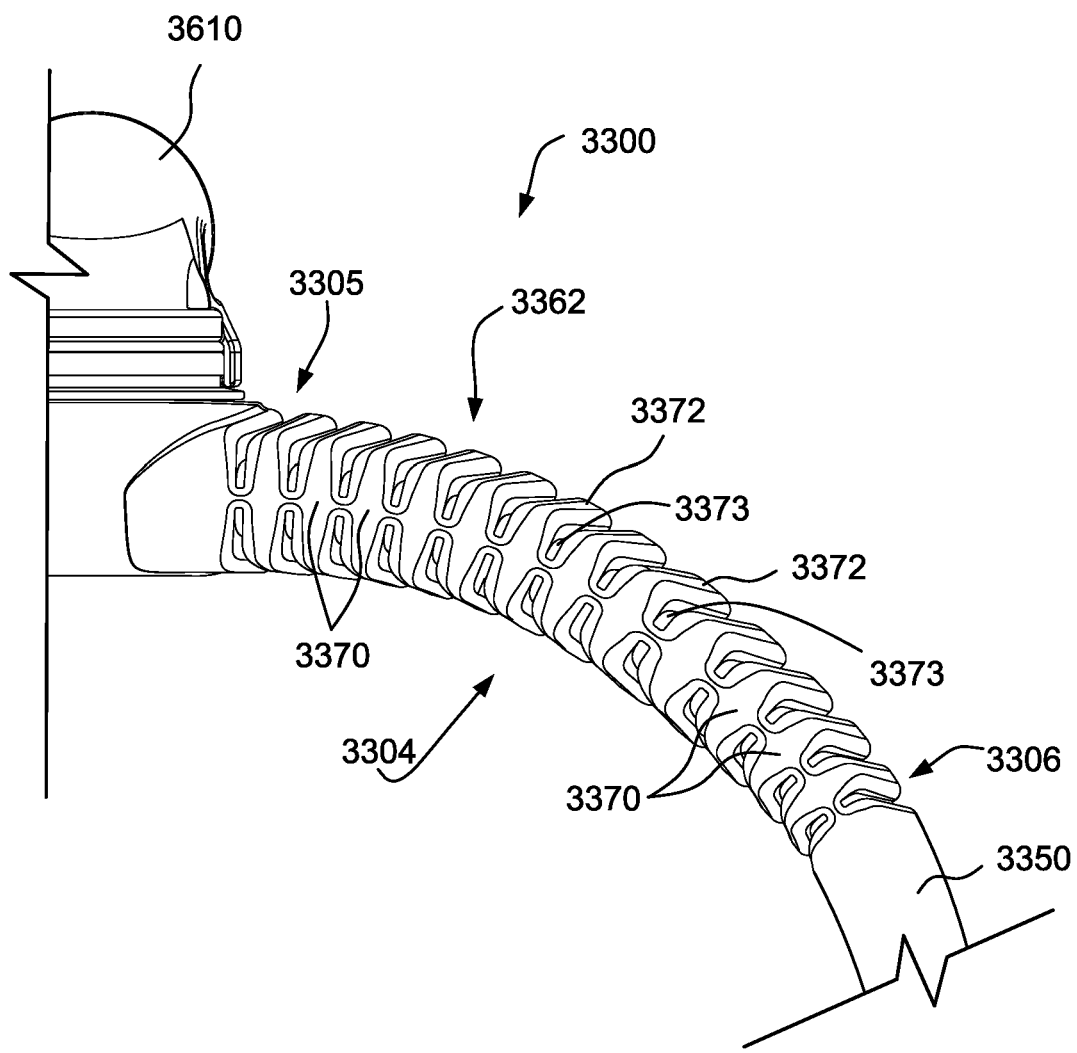

FIG. 10H shows a front view of the extendable portion shown in FIG. 10G in a curved configuration.

Figure 10I:
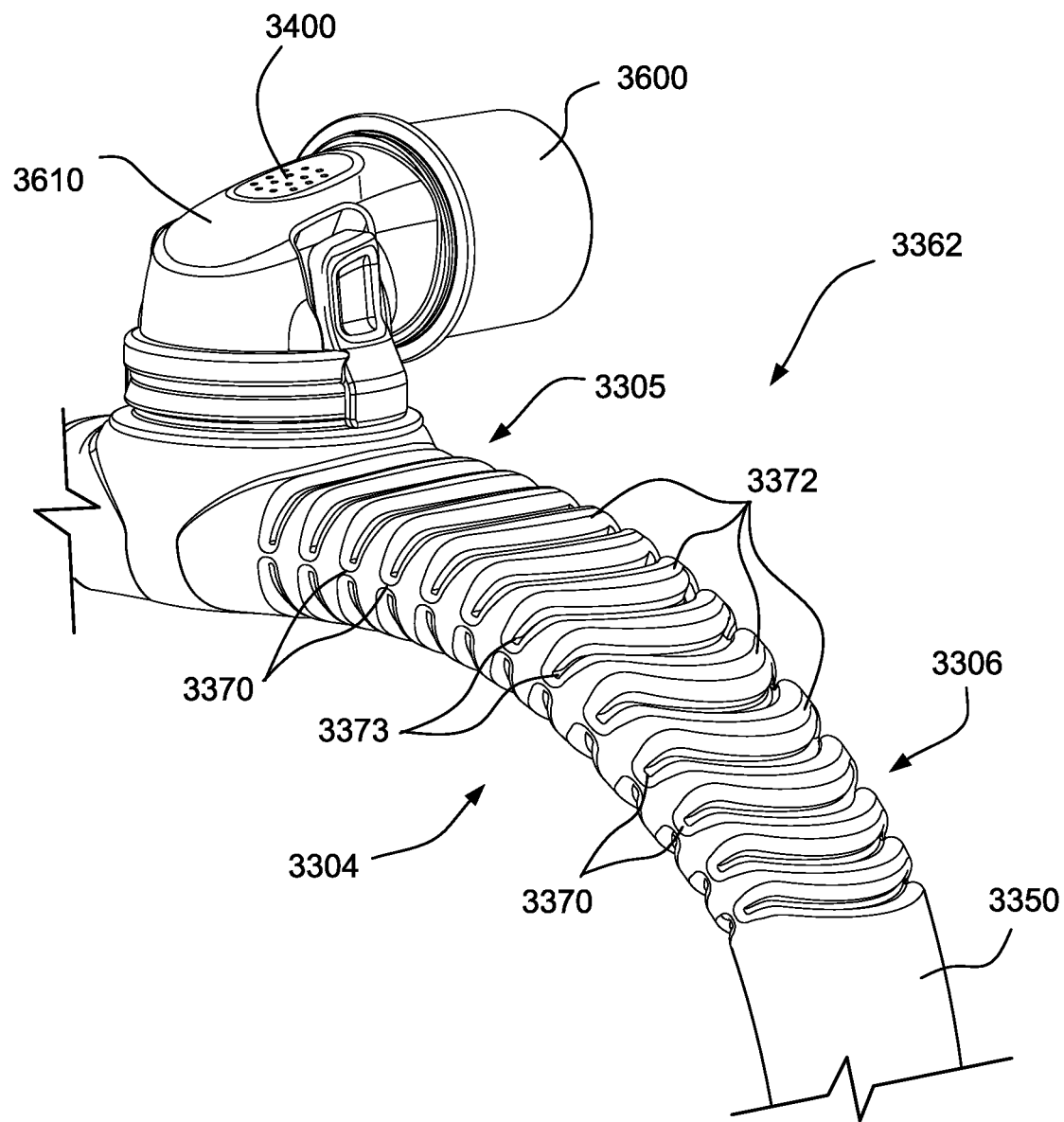

FIG. 10I shows a perspective view of the extendable portion shown in FIG. 10G in a curved configuration.

Figure 10J:
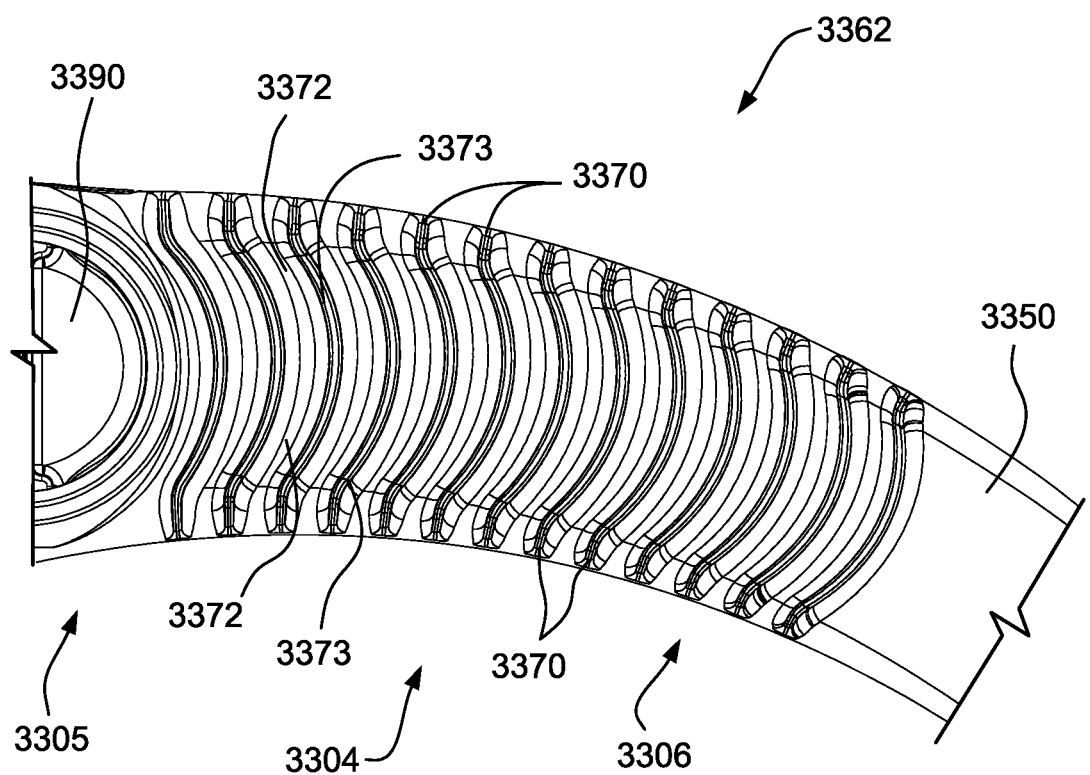

FIG. 10J shows a top view of the extendable portion shown in FIG. 10G in a curved configuration.

Figure 11A:
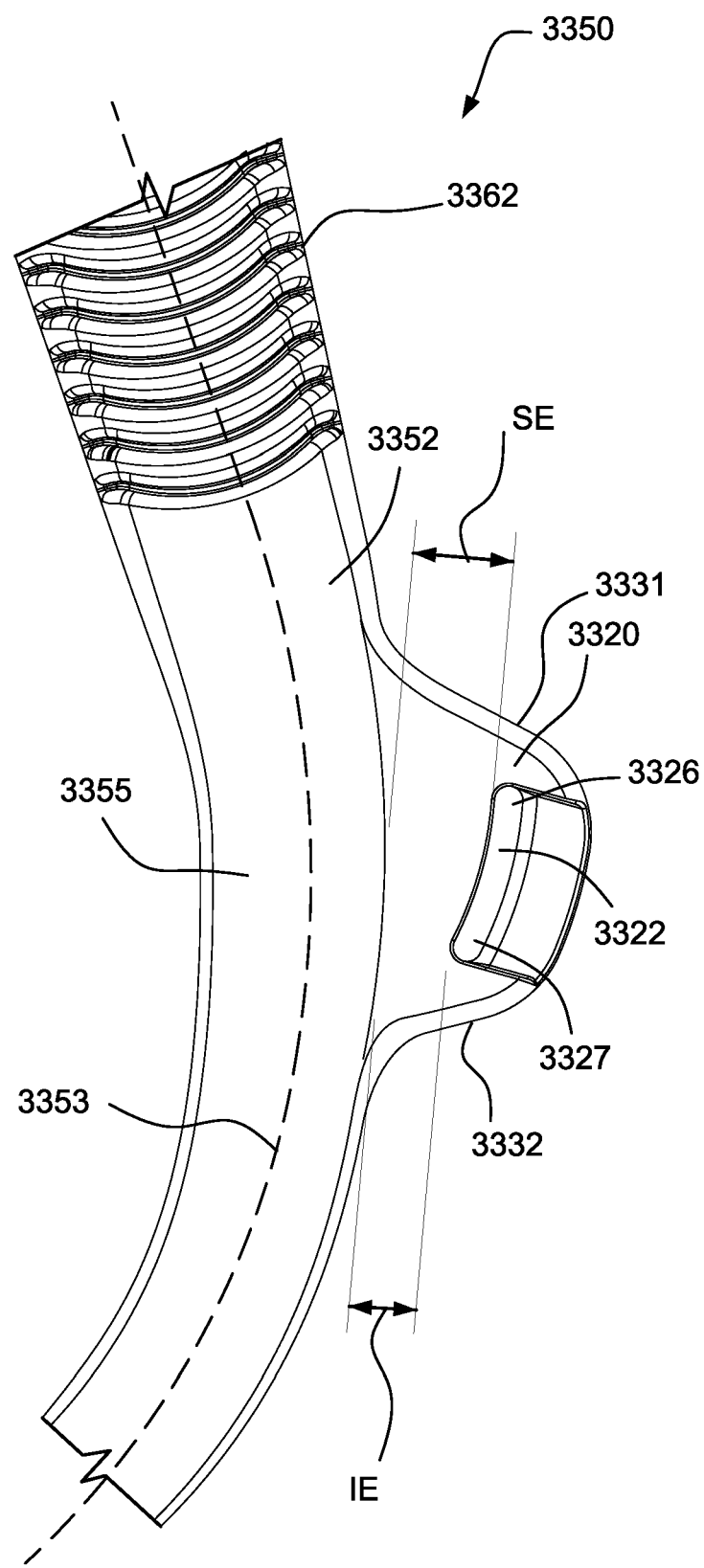

FIG. 11A shows a side view of a tab of the positioning and stabilising structure 3300 of FIG. 10A.

Figure 11B:
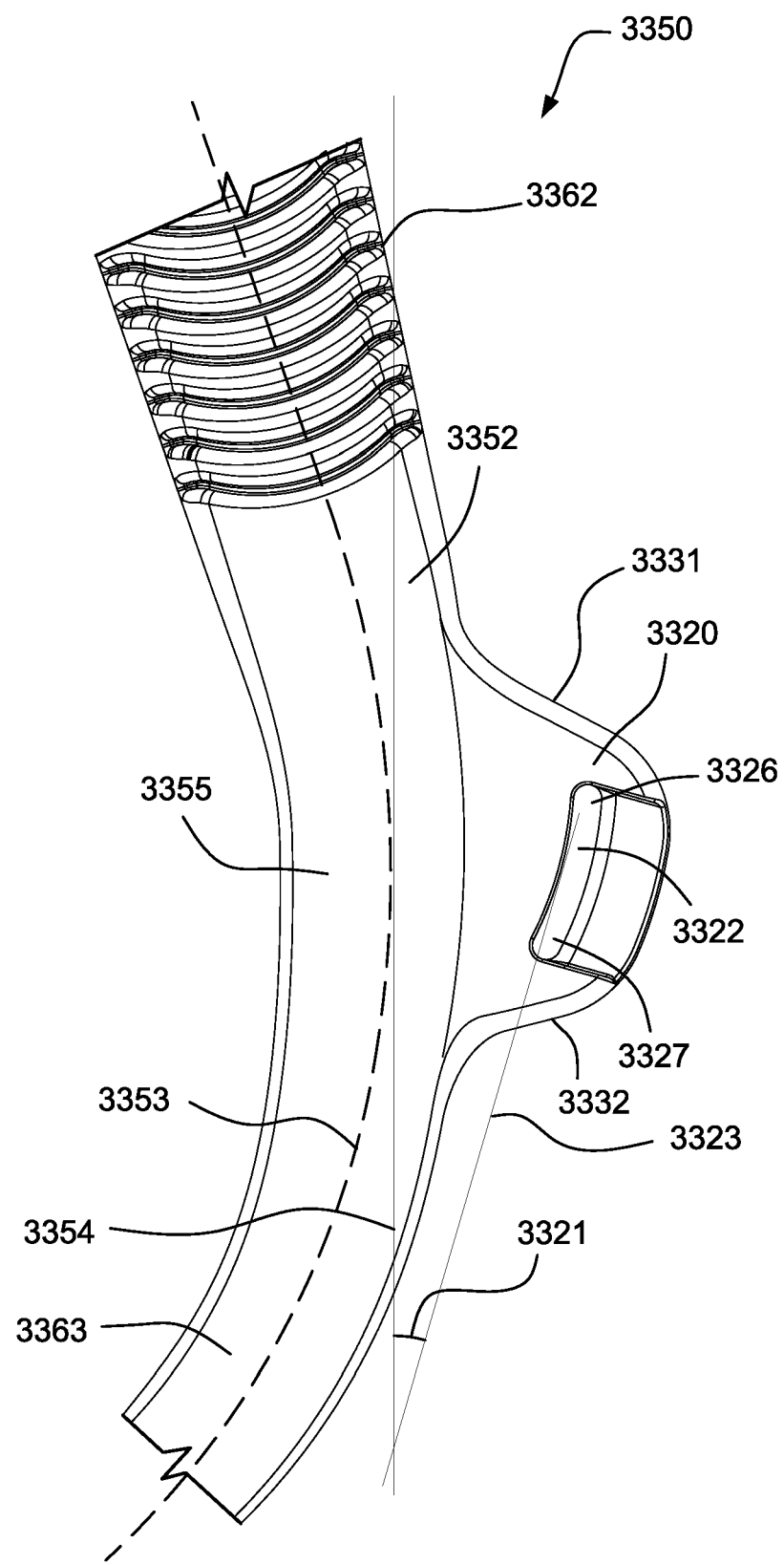

FIG. 11B shows another side view of a tab of the positioning and stabilising structure 3300 of FIG. 10A

Figure 11C:
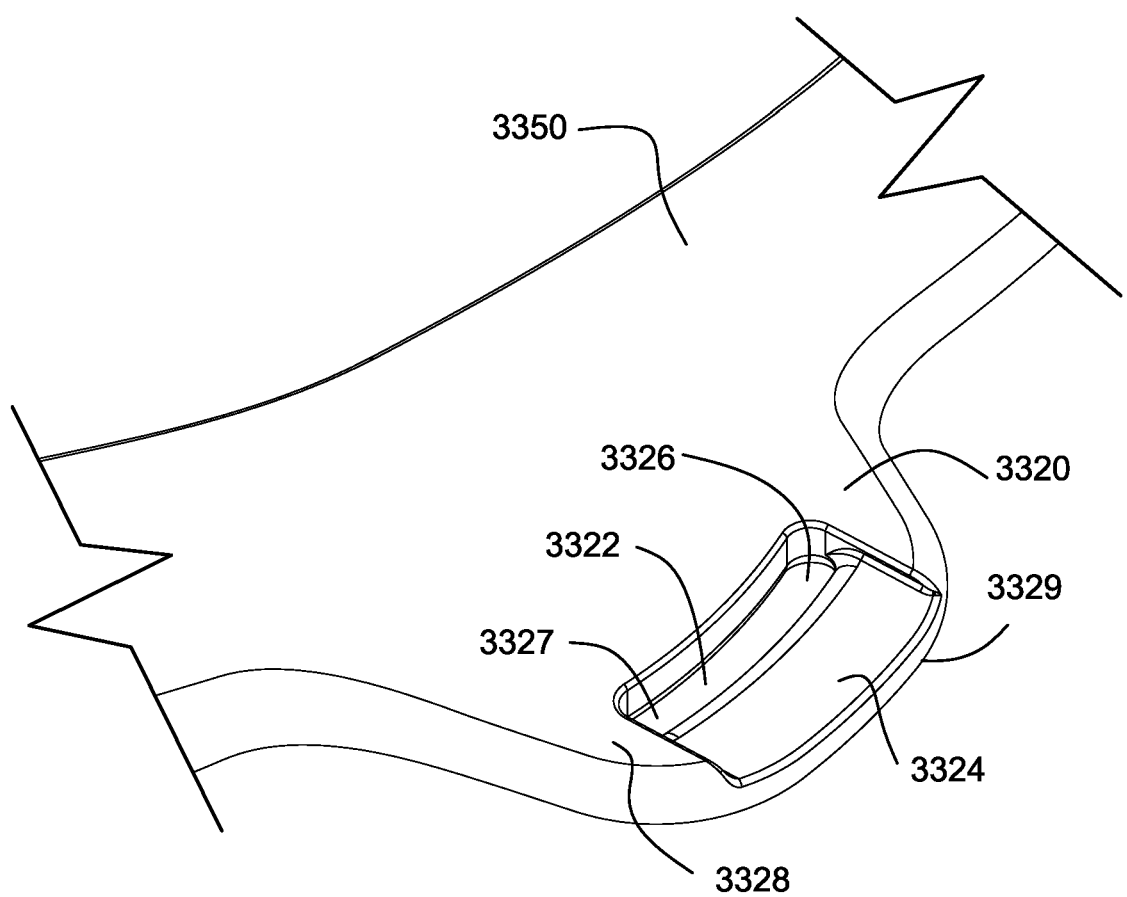

FIG. 11C is a perspective view of the tab of FIG. 11A.

Figure 12A:
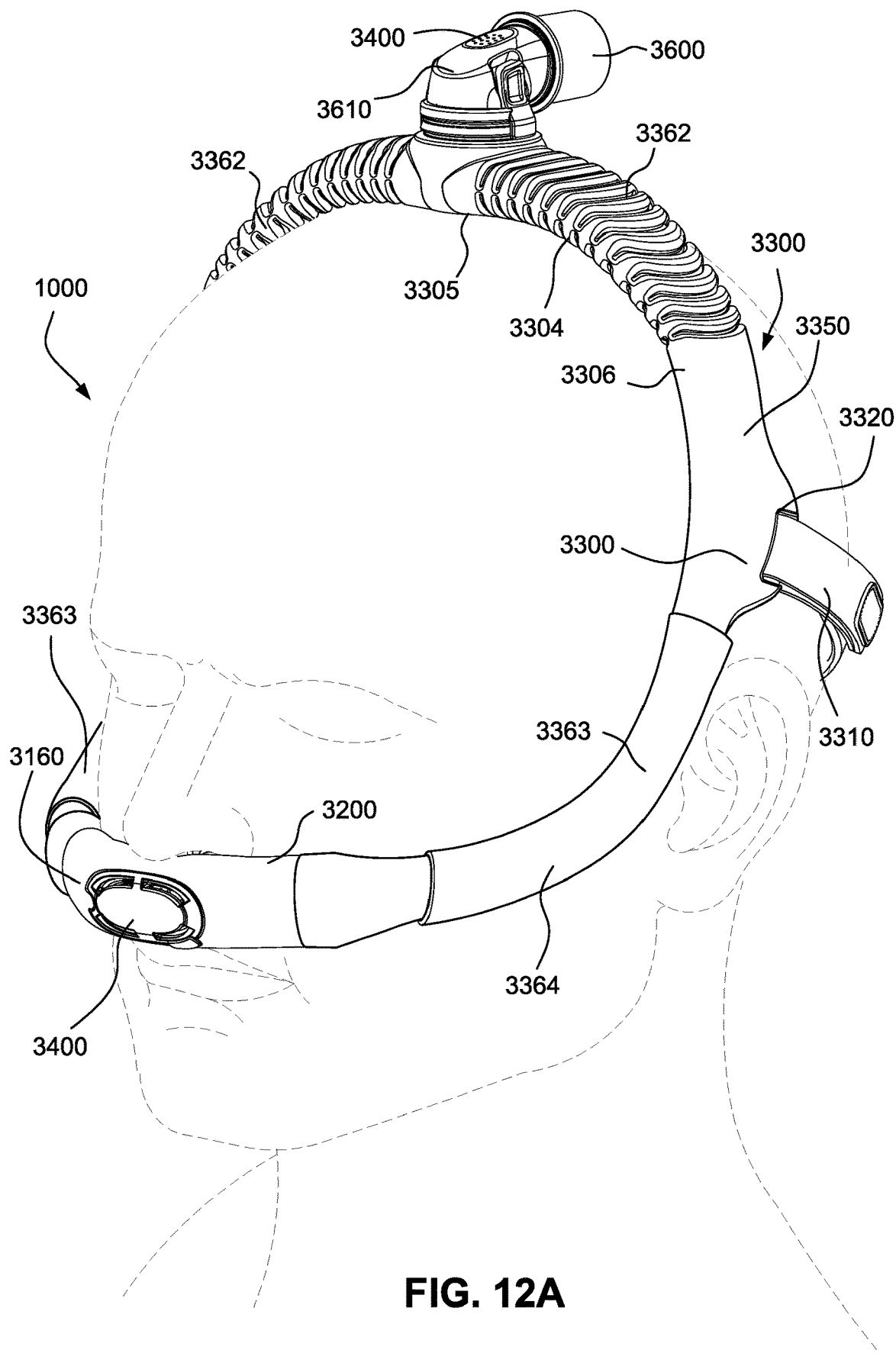

FIG. 12A is perspective view of a patient interface 3000 according to another example of the present technology while worn by a patient 1000.

Figure 12B:
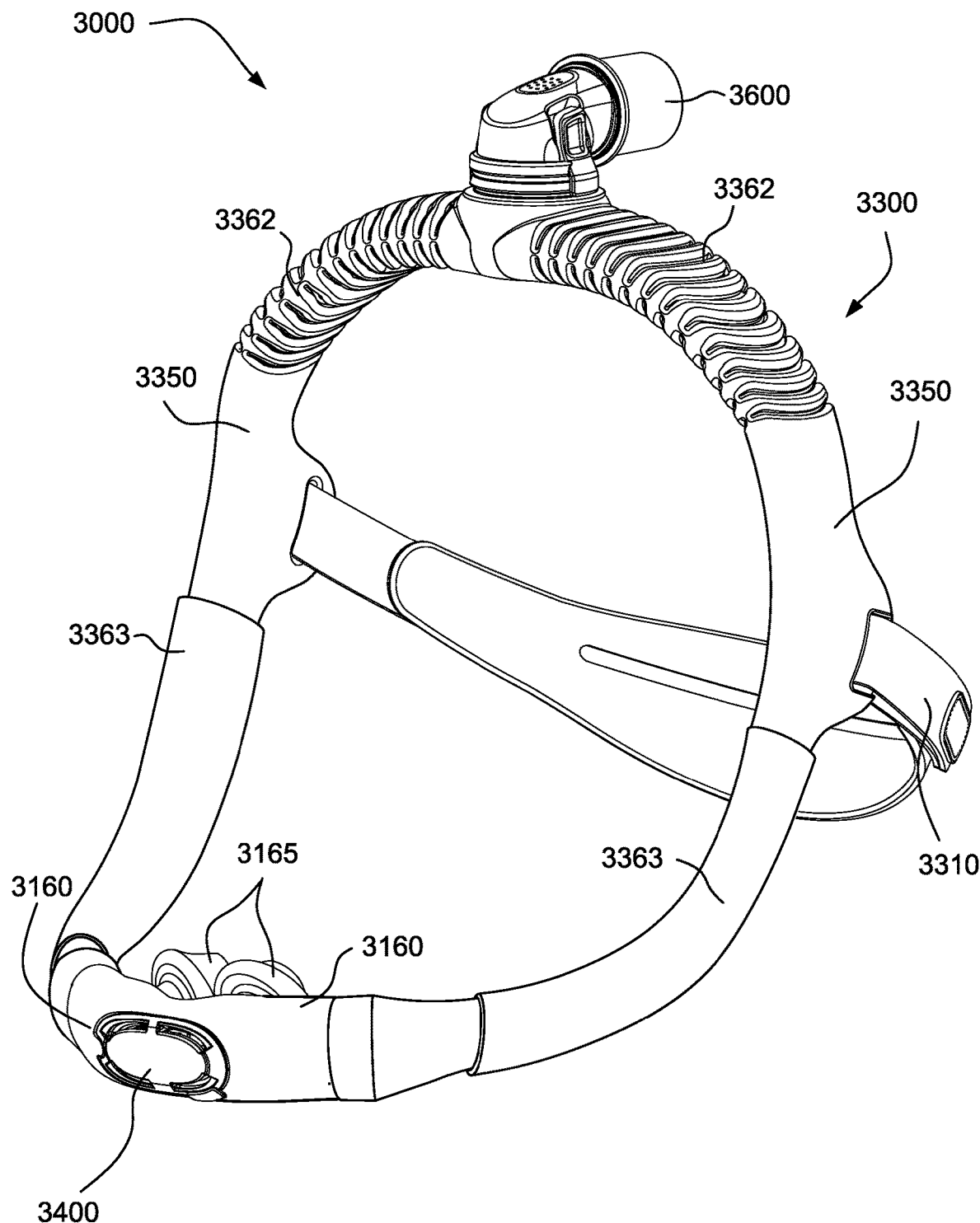

FIG. 12B is a perspective view of the patient interface 3000 of FIG. 12A in isolation.

Figure 12C:
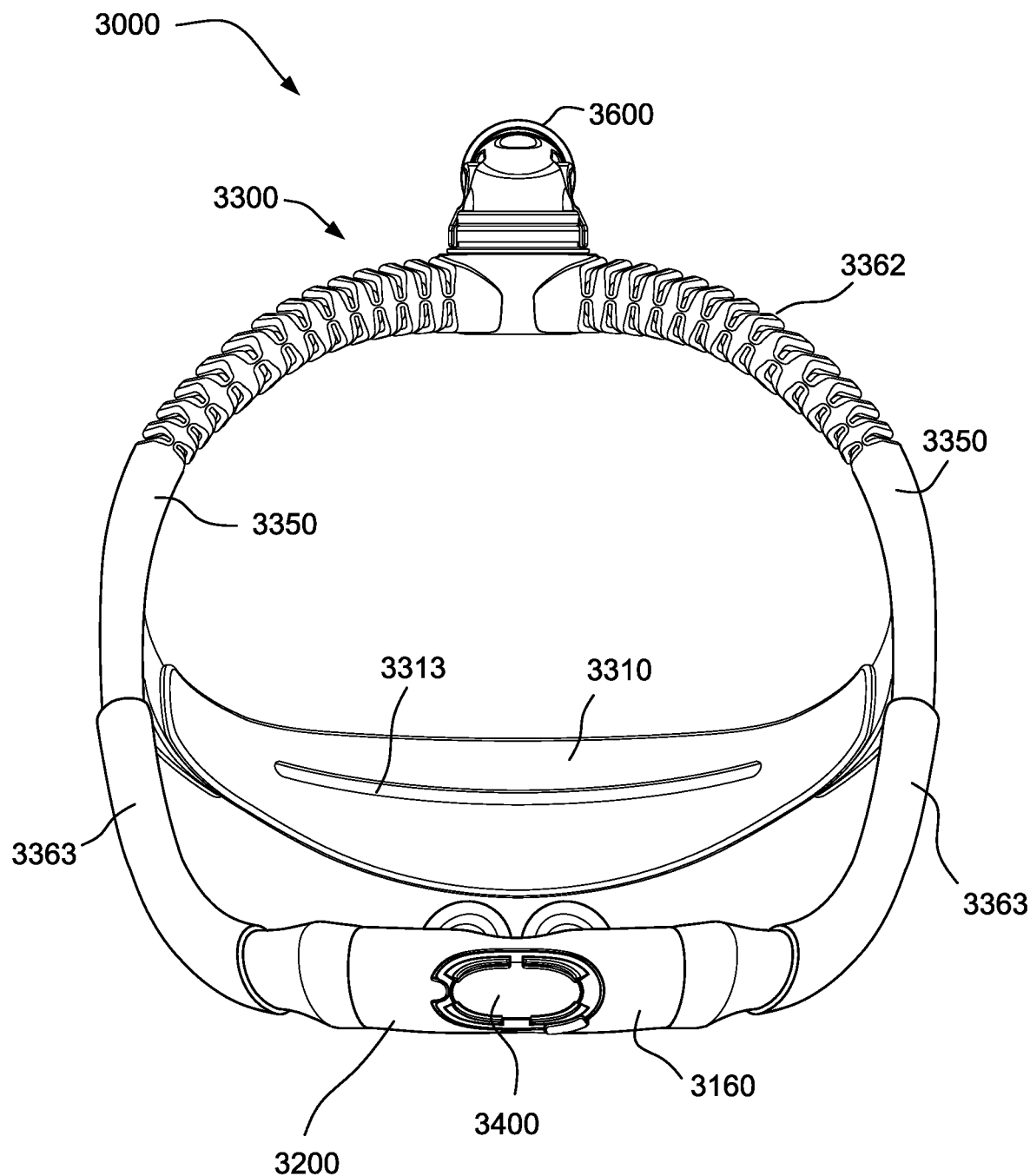

FIG. 12C is a front view of the patient interface 3000 of FIG. 12A.

Figure 12D:
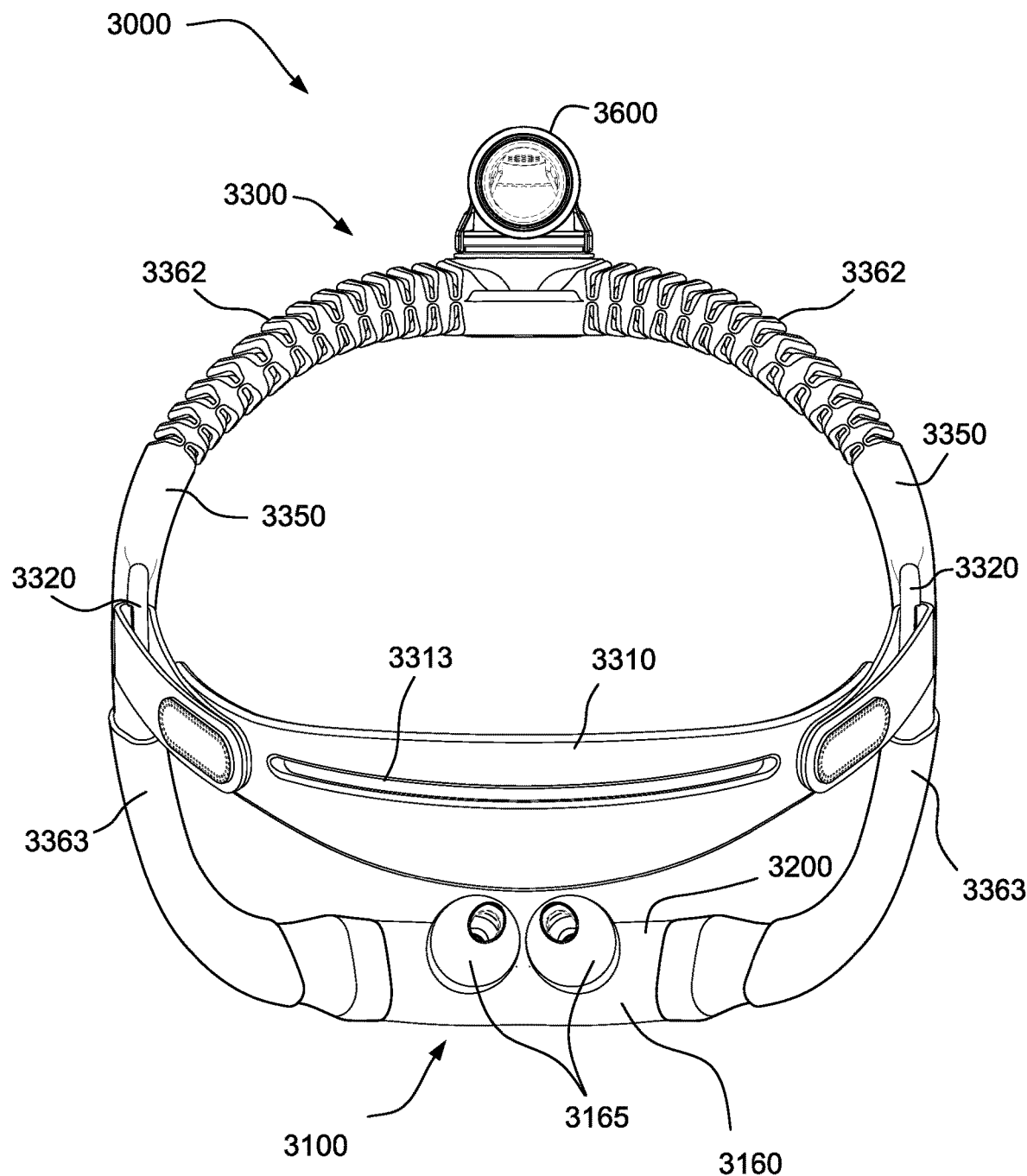

FIG. 12D is a rear view of the patient interface 3000 of FIG. 12A.

Figure 12E:
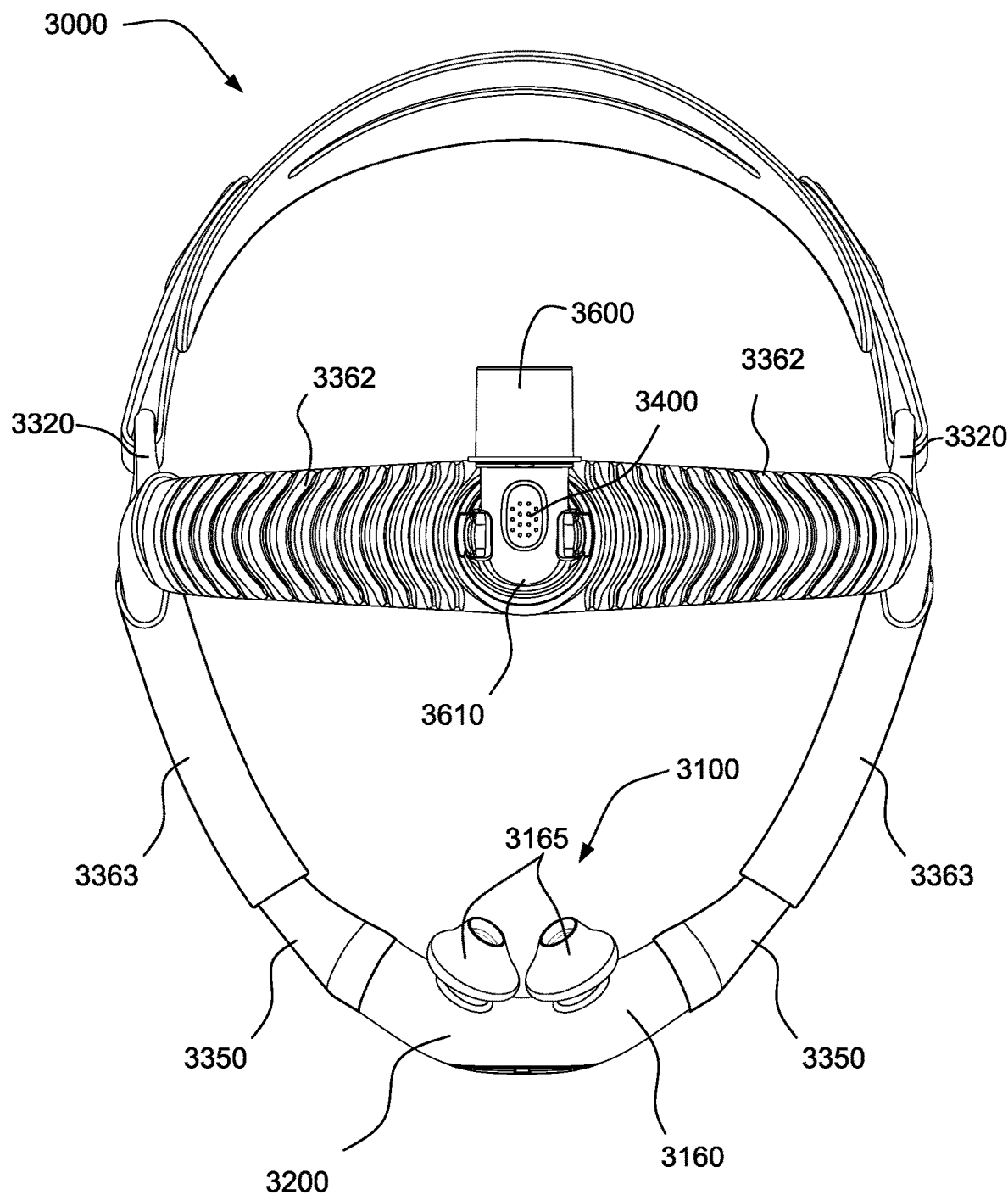

FIG. 12E is a plan view of the patient interface 3000 of FIG. 12A.

Figure 12F:
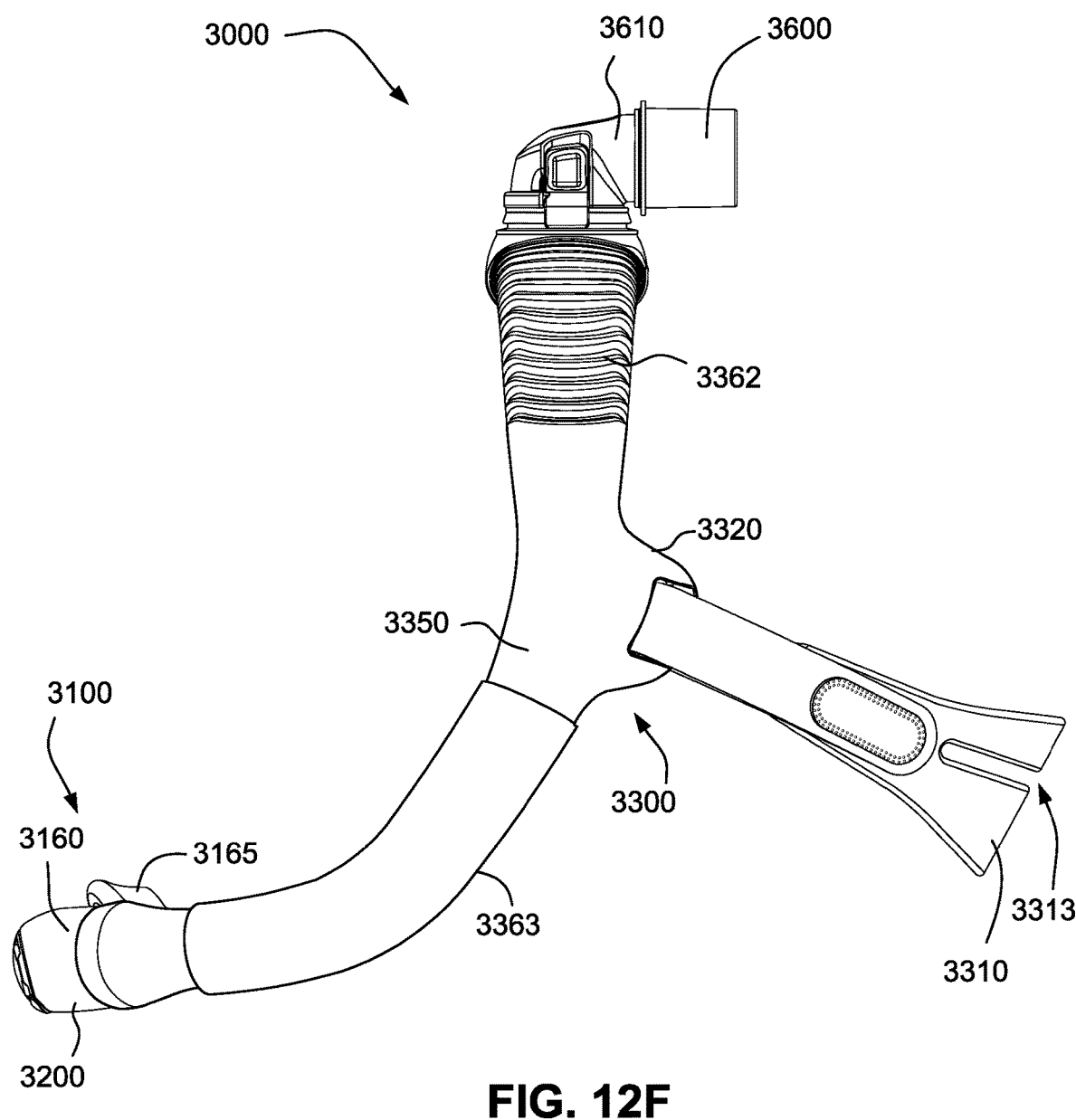

FIG. 12F is a side view of the patient interface 3000 of FIG. 12A.

Figure 13:
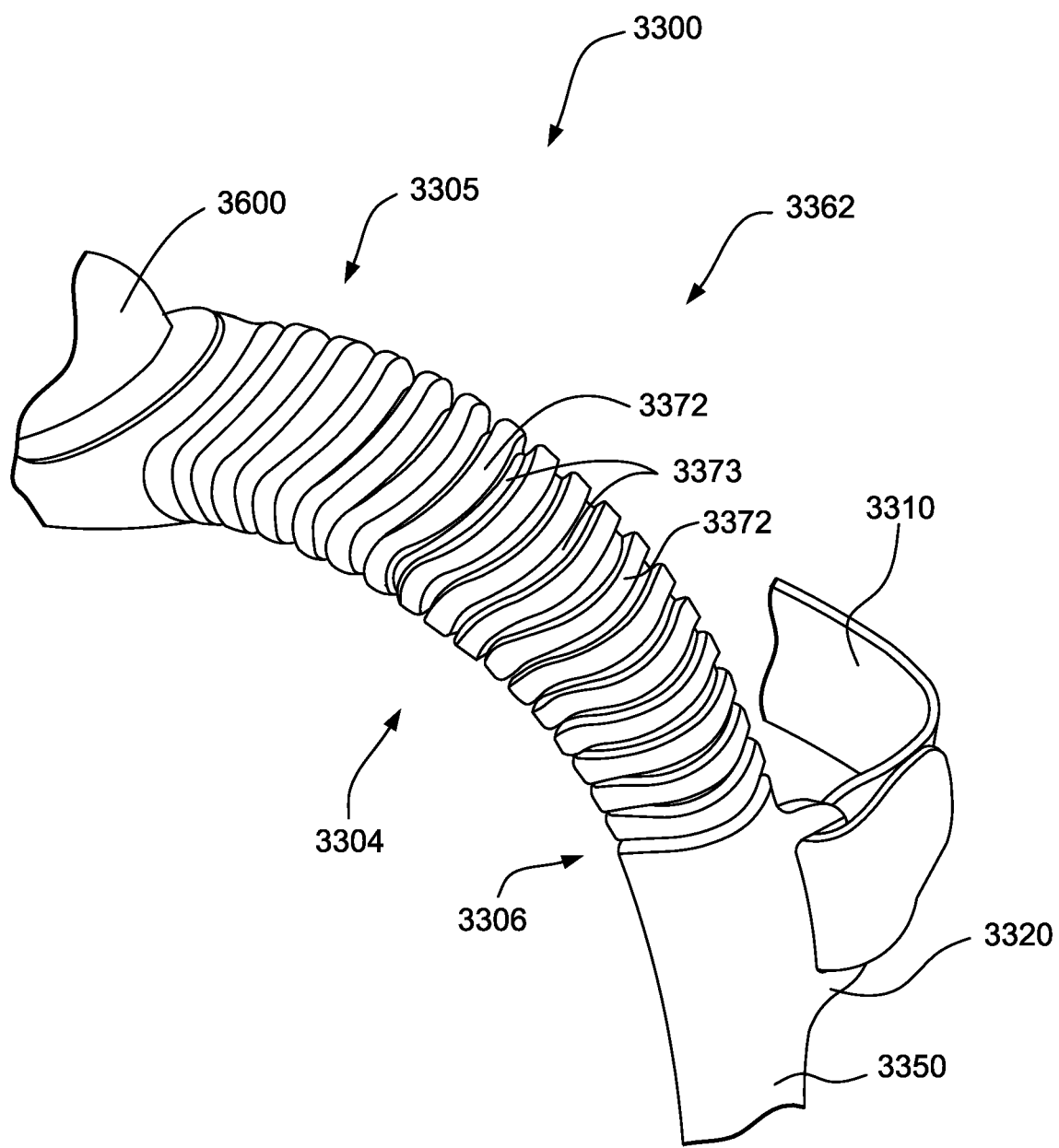

FIG. 13 is a perspective view of a portion of a positioning and stabilising structure 3300 of a patient interface according to another example of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

Figure 1A:
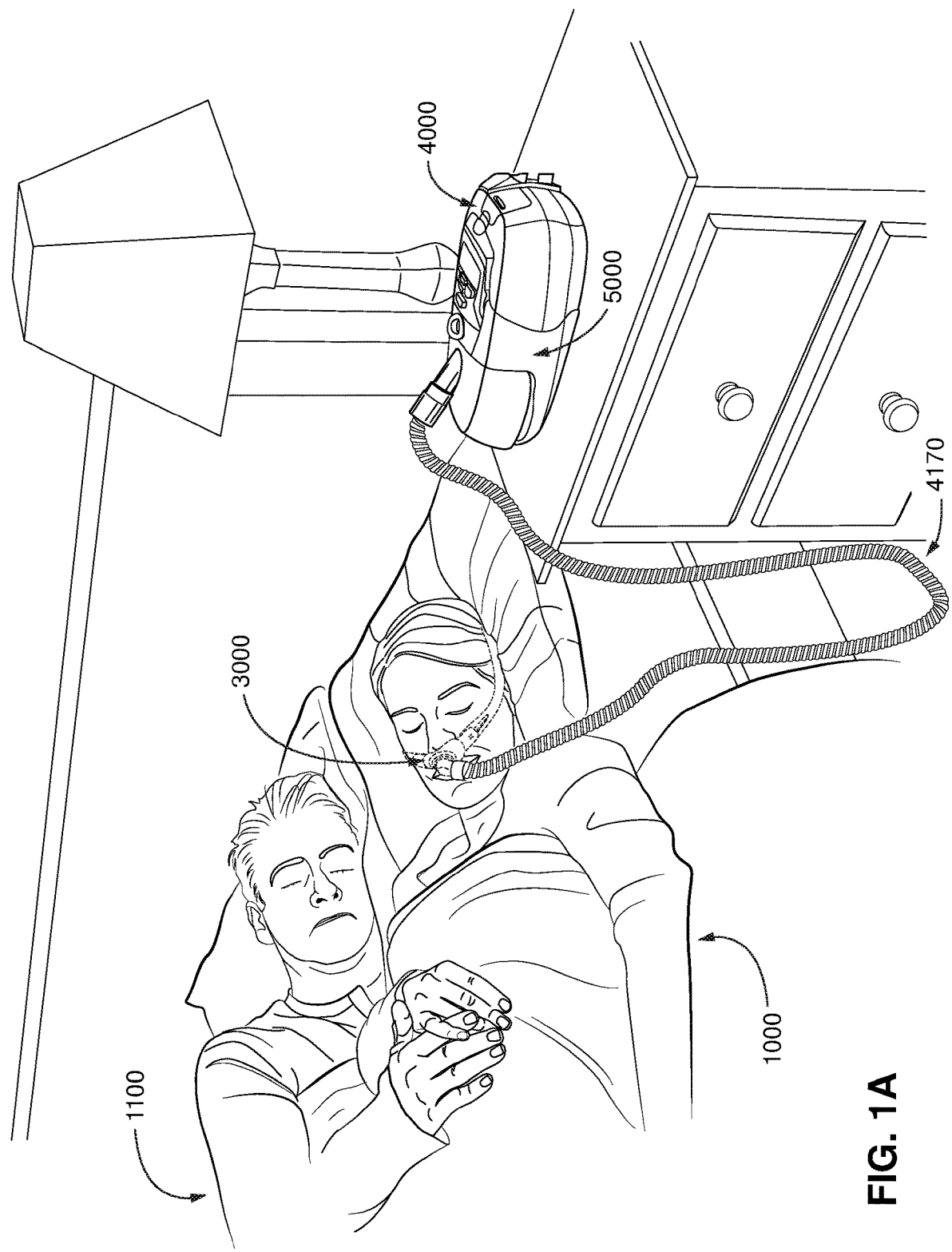

In one form as shown in FIG. 1A, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Treatment Systems

Figure 1B:
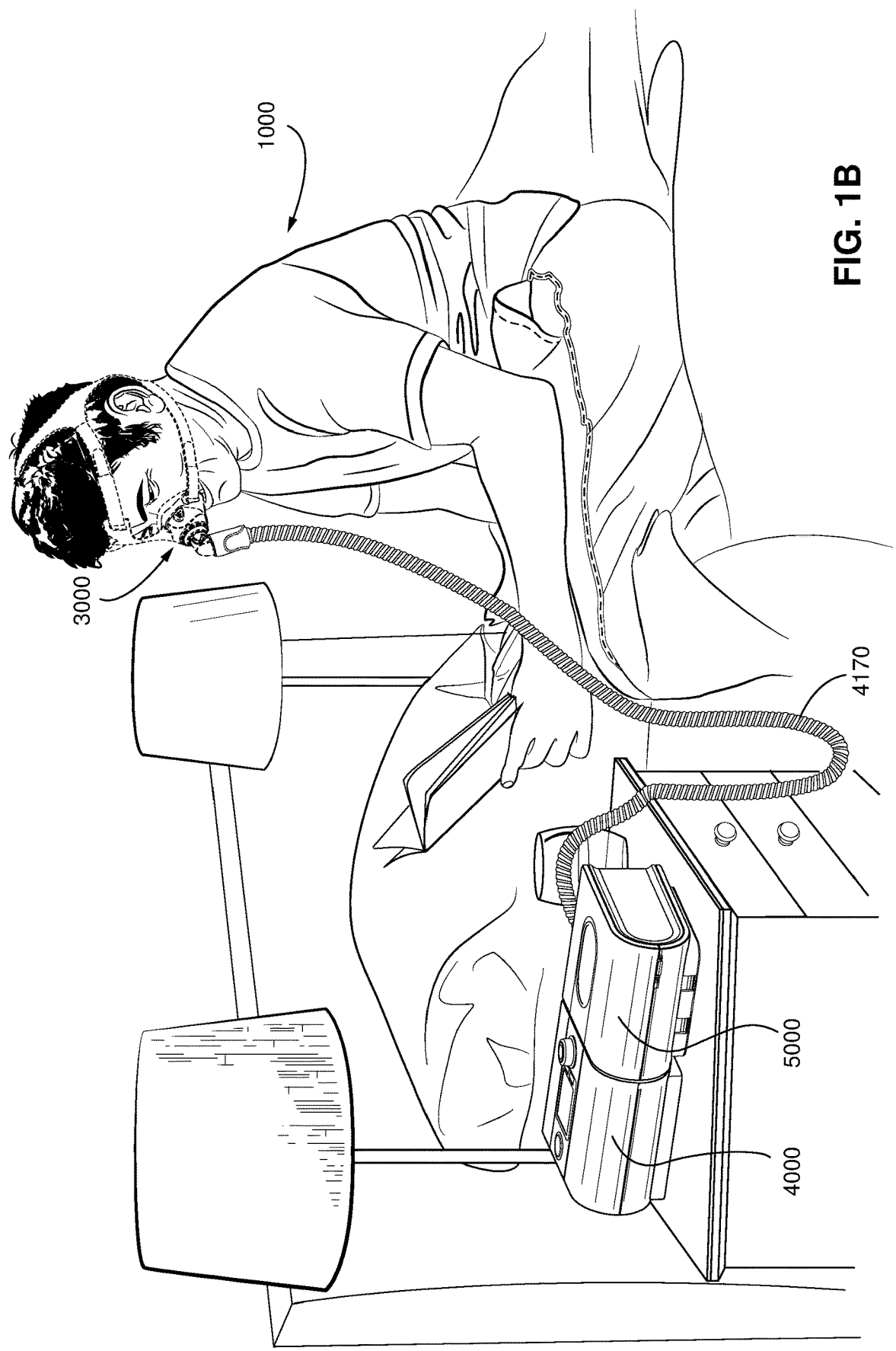
Figure 1C:

In one form, the present technology comprises an apparatus or device for treating a respiratory disorder. The apparatus or device may comprise an RPT device 4000 for supplying pressurised air to the patient 1000 via an air circuit 4170 to a patient interface 3000. FIGS. 1A, 1B and 1C illustrate treatment systems that utilise patent interfaces 3000 with RPT devices 4000 and humidifiers 5000.

5.3 Patient Interface

With reference to FIG. 3A, a patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

As shown in FIGS. 8A-9C, a patient interface 3000 in accordance with one aspect of the present technology comprises the following functional aspects: a seal-forming structure 3100, a plenum chamber 3200, a positioning and stabilising structure 3300, a vent 3400 and one form of connection port 3600 for connection to an air circuit (e.g. the air circuit 4170 shown in FIGS. 1A-1C). In this example, the seal-forming structure 3100 and the plenum chamber 3200 are provided by a cushion module 3150.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one seal-forming structure 3100, each being configured to correspond to a different size and/or shape range. For example, the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure 3100 includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface, and/or having a higher coefficient of friction compared to other surfaces.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure 3100 of the patient interface 3000 comprises a pair of nasal puffs, or nasal pillows, each nasal puff or nasal pillow being constructed and arranged to form a seal with a respective naris of the nose of a patient. FIGS. 12A-F show a patient interface 3000 having a seal-forming structure 3100 provided by a pillows cushion module 3160. The pillows cushion module 3160 comprises a pair of nasal pillows 3165. In this example, the same positioning and stabilising structure 3300 as shown in FIGS. 8A-9C is used to hold the pillows cushion module 3160 in sealing contact with the patient's nose. The same concepts and features of the positioning and stabilising structure 3300 described with reference to the cradle cushion module 3150 may be applied to a positioning and stabilising structure 3300 configured to be used with the pillows cushion module 3160 (or another type of cushion module such as a full face cushion module, oro-nasal cushion module, ultra-compact full face cushion module, nasal cushion module and the like).

Nasal pillows 3165 in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.7 Nasal Cradle

In one form, for example as shown in FIGS. 8A-9C, the seal-forming structure 3100 is configured to form a seal in use with the underside of the nose around the nares and optionally with the lip superior of the patient 1000. This type of seal-forming structure may be referred to as a "cradle cushion" or "sub-nasal mask". The shape of the seal-forming structure may be configured to match or closely follow the underside of the patient's nose, i.e. the profile and angle of the seal-forming structure may be substantially parallel to the patient's naso-labial angle. In one form of nasal cradle cushion, the seal-forming structure comprises a bridge portion defining two orifices, each of which, in use, supplies air or breathable gas to a different one of the patient's nares. The bridge portion may be configured to contact or seal against the patient's columella in use. In some forms of the technology, the seal-forming structure 3100 is configured to form a seal on an underside of the patient's nose without contacting a nasal bridge region of the patient's nose. In some examples, patient interface may comprise a seal-forming structure 3100 in the form of a cradle cushion as described in PCT Application No. PCT/AU2018/050289, filed Mar. 29, 2018, the entire contents of which are incorporated herein by reference.

5.3.1.8 Nasal Mask Cushion

In one form, the patient interface 3000 comprises a seal-forming portion that forms a seal in use on an upper lip region (that is, the lip superior), a nasal bridge region and a cheek region of the patient's face. This is the case, for example, with the patient interface 3000 shown in FIG. 1B. This seal-forming portion delivers a supply of air or breathable gas to both nares of patient 1000 through a single orifice. This type of seal-forming structure may be referred to as a "nasal cushion" or "nasal mask". In some examples of the present technology, the positioning and stabilising structure 3300 shown in FIGS. 8A-9C may be utilised to hold a nasal cushion in sealing position on a patient's face.

5.3.1.9 Full-Face Mask Cushion

In one form the patient interface 3000 comprises a seal-forming portion that forms a seal in use on a chin-region, a nasal bridge region and a cheek region of the patient's face. This is the case, for example, with the patient interface 3000 shown in FIG. 1C. This seal-forming portion delivers a supply of air or breathable gas to both nares and mouth of patient 1000 through a single orifice. This type of seal-forming structure may be referred to as a "full-face mask". In some examples of the present technology, the positioning and stabilising structure 3300 shown in FIGS. 8A-9C may be utilised to hold a full-face cushion in sealing position on a patient's face.

5.3.1.10 Oronasal Mask Cushion

In another form the patient interface 3000 comprises a nasal seal-forming structure in the manner of a nasal cushion or nasal cradle cushion and an oral seal-forming structure that is configured to form a seal in use around the mouth of a patient (which may be referred to as a "mouth cushion" or "oral mask"). In such a mask air or breathable gas is supplied in use through separate orifices to the patient's nares and the patient's mouth. This type of seal-forming structure 3100 may be referred to as an "oronasal cushion" or "ultra-compact full face cushion". In one form, the nasal seal-forming structure and oral seal-forming structure are integrally formed as a single component. In some examples, patient interface may comprise a seal-forming structure 3100 in the form of a cradle cushion as described in U.S. Patent Application No. 62/649,376, the entire contents of which are incorporated herein by reference.

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, such as in the patient interface 3000 of FIGS. 8A-9C, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

5.3.2 Positioning and Stabilising Structure

The seal-forming structure 3100 of the patient interface 3000 of the present technology may be held in sealing position in use by the positioning and stabilising structure 3300. Positioning and stabilising structure 3300 may be referred to as "headgear" since it engages the patient's head in order to hold the patient interface 3000 in a sealing position.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap 3310 constructed from a laminate of a fabric patient-contacting layer, a foam inner layer and a fabric outer layer. In one form, the foam is porous to allow moisture, (e.g., sweat), to pass through the strap 3310. The strap 3310 may be breathable to allow moisture vapour to be transmitted through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure into sealing contact with a portion of a patient's face, in some examples in combination with other straps or other structures. In an example the strap may be configured as a tie.

A tie will be understood to be a structure designed to resist tension. In use, a tie is part of the positioning and stabilising structure 3300 that is under tension. Some ties will impart an elastic force as a result of this tension, as will be described. A tie may act to maintain the seal-forming structure 3100 in a therapeutically effective position on the patient's head.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone and/or frontal bone without overlaying the occipital bone. The first tie may be provided, for example, as part of a patient interface that comprises a cradle cushion, nasal pillows, nasal cushion, full-face cushion or an oronasal cushion. For example, as shown in FIGS. 8A-9C, the positioning and stabilising structure 3300 comprises a first tie in the form of tubes 3350 which lie over the top of the patient's head.

In one form of the present technology suitable for a nasal-only mask or for a full-face mask, the positioning and stabilising structure 3300 includes a second tie, the second tie being constructed and arranged so that in use at least a portion of a superior edge thereof passes inferior to an otobasion inferior of the patient's head and overlays or lies inferior to the occipital bone of the patient's head. The second tie may be provided, for example, as part of a patient interface that comprises a cradle cushion, nasal pillows, full-face cushion, nasal cushion or an oronasal cushion. As shown in FIGS. 8A-9C, the positioning and stabilising structure 3300 comprises a second tie in the form of a strap 3310 that lies against posterior surfaces of the patient's head.

In one form of the present technology suitable for a nasal-only mask or for a full-face mask or oronasal mask, the positioning and stabilising structure 3300 includes a third tie that is configured to anchor against posterior surfaces of the patient's neck. Additionally, in some forms the positioning and stabilising structure comprises a fourth tie that is constructed and arranged to interconnect the second tie and the third tie to reduce a tendency of the second tie and the third tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping. As shown in FIGS. 8A-9C, the positioning and stabilising structure 3300 comprises a strap 3310 that is bendable. The strap 3310 may be considered a backstrap. The strap 3310 is sufficiently flexible to pass around the back of the patient's head and lie comfortably against the patient's head, even when under tension in use.

In certain forms of the present technology, a system is provided comprising more than one positioning and stabilizing structure 3300, each being configured to provide a retaining force to correspond to a different size and/or shape range. For example, the system may comprise one form of positioning and stabilizing structure 3300 suitable for a large sized head, but not a small sized head, and another suitable for a small sized head, but not a large sized head.

5.3.2.1 Headgear Tubing

In some forms of the present technology, the positioning and stabilising structure 3300 comprises one or more tubes 3350 that deliver pressurised air received from a conduit forming part of the air circuit 4170 from the RPT device to the patient's airways, for example through the plenum chamber 3200 and seal-forming structure 3100. In the form of the present technology illustrated in FIGS. 8A-9C, the positioning and stabilising structure 3300 comprises two tubes 3350 that deliver air to the seal-forming structure 3100 from the air circuit 4170. The tubes 3350 are an integral part of the positioning and stabilising structure 3300 of patient interface 3000 to position and stabilise the seal-forming structure 3100 of the patient interface to the appropriate part of the patient's face (for example, the nose and/or mouth). This allows the conduit of air circuit 4170 providing the flow of pressurised air to connect to a connection port 3600 of the patient interface in a position other than in front of the patient's face which may be unsightly to some people. While a pair of tubes 3350 have some advantages (described below), in some examples, the positioning and stabilising structure 3300 comprises only a single tube 3350 configured to overlie the patient's head on one side. A strap or other stabilising component may be provided to the other side of the patient's head between the top end of the single tube 3350 and the seal-forming structure 3100, to provide balanced forces on the seal-forming structure 3100.

Since air can be contained and passed through headgear tubing 3350 in order to deliver pressurised air from the air circuit 4170 to the patient's airways, the positioning and stabilising structure 3300 may be described as being inflatable. It will be understood that an inflatable positioning and stabilising structure 3300 does not require all components of the positioning and stabilising structure 3300 to be inflatable. For example, in the example shown in FIGS. 8A-9C and 12A-F, the positioning and stabilising structure 3300 comprises the headgear tubing 3350, which is inflatable, and the strap 3310, which is not inflatable.

In certain forms of the present technology, the patient interface 3000 may comprise a connection port 3600 located proximal a top, side or rear portion of a patient's head. For example, in the form of the present technology illustrated in FIGS. 8A-9C, the connection port 3600 is located on top of the patient's head. In this example the patient interface 3000 comprises an elbow 3610 to which the connection port 3600 is provided. The elbow 3610 may swivel with respect to the positioning and stabilising structure 3300 and order to decouple movement of a conduit connected to the connection port 3600 from the positioning and stabilising structure 3300. Additionally, or alternatively, a conduit connected to the connection port 3600 may swivel with respect to the elbow 3610. In the illustrated example, elbow 3610 comprises a swivelling conduit connector to which a conduit of the air circuit 4170 is able to connect such that the conduit can rotate about its longitudinal axis with respect to the elbow 3610. The connection port 3600 may comprise fluid connection opening 3390, for example as shown in FIGS. 10A and 10B. In some examples the air circuit 4170 may connect to the fluid connection opening 3390. The elbow 3610 may rotatably connect to the fluid connection opening or to a ring received in the fluid connection opening.

Patient interfaces in which the connection port is not positioned in front of the patient's face may be advantageous as some patients find a conduit that connects to a patient interface in front of the face to be unsightly and obtrusive. For example, a conduit connecting to a patient interface in front of the face may be prone to being tangled up in bedclothes or bed linen, particularly if the conduit extends downwardly from the patient interface in use. Forms of the technology with a patient interface with a connection port positioned proximate the top of the patient's head in use may make it easier or more comfortable for a patient to lie or sleep in one or more of the following positions: in a side or lateral position; in a supine position (i.e. on their back, facing generally upwards); and in a prone position (i.e. on their front, facing generally downwards). Moreover, connecting a conduit to the front of a patient interface may exacerbate a problem known as tube drag, wherein the conduit may provide an undesired drag force upon the patient interface thereby causing dislodgement away from the face.

In the form of the present technology illustrated in FIGS. 8A-9C and 12A-F, the positioning and stabilising structure 3300 comprises two tubes 3350, each tube 3350 being positioned in use on a different side of the patient's head and extending across the respective cheek region, above the respective ear (superior to the otobasion superior on the patient's head) to the elbow 3610 on top of the head of the patient 1000. This form of technology may be advantageous because, if a patient sleeps with their head on its side and one of the tubes is compressed to block or partially block the flow of gas along the tube, the other tube remains open to supply pressurised gas to the patient. In other examples of the technology, the patient interface 3000 may comprise a different number of tubes, for example one tube, or three or more tubes. In one example in which the patient interface has one tube 3350, the single tube 3350 is positioned on one side of the patient's head in use (e.g. across one cheek region) and a strap forms part of the positioning and stabilising structure 3300 and is positioned on the other side of the patient's head in use (e.g. across the other region) to assist in securing the patient interface 3000 on the patient's head.

In the form of the technology shown in FIGS. 8A-9C and 12A-F the two tubes 3350 are fluidly connected at their upper ends to each other and to connection port 3600. In one embodiment, the two tubes are integrally formed while in other embodiments the tubes are separate components that are connected together in use and may be disconnected, for example for cleaning or storage. Where separate tubes are used they may be indirectly connected together, for example each may be connected to a T-shaped conduit having two conduit arms each fluidly connectable to the tubes 3350 and a third conduit arm or opening acting as the connection port 3600 and connectable in use to the air circuit 4170. The connection port 3600 may comprise an elbow 3610 received in fluid connection opening 3390 at the centre of two integrally formed tubes 3350. The elbow 3610 may be received in a ring in the fluid connection opening 3390 and may be configured to swivel within the ring. The fluid connection opening 3390 may be also considered a connection port 3600 itself.

The tubes 3350 may be formed of a semi-rigid material such as an elastomeric material, e.g. silicone. For example, the tubes 3350, from the left-side non-extendable tube section 3363 to the right side non-extendable tube section 3363, may be formed (e.g., by molding) from a single homogeneous piece of material, such as silicone, as can be seen in FIG. 10A. The tubes may have a natural, preformed shape and be able to be bent or moved into another shape if a force is applied to the tubes. For example, the tubes may be generally arcuate or curved in a shape approximating the contours of a patient's head between the top of the head and the nasal or oral region.

The positioning and stabilising structure 3300 in some examples may comprise sleeves 3364 around the tubes 3350. For example, as shown in FIGS. 8A to 8D, sleeves 3364 are provided to the non-extendable tube sections 3363. In some examples, the patient interface 3000 may not comprise sleeves 3364 and in other examples the patient interface 3000 may comprise sleeves 3364 that cover more, or all, of the tubes 3350. The sleeves 3364 may be formed to fit to the curved shape of the tubes 3350. In some examples, the sleeves 3364 are formed from a smooth fabric. The sleeves 3364 may be more comfortable against the patient's face than the tube 3350 without any covering.

As described in U.S. Pat. No. 6,044,844, the contents of which are incorporated herein, the tubes 3350 may be crush resistant to avoid the flow of breathable gas through the tubes if either is crushed during use, for example if it is squashed between a patient's face and pillow. Crush resistant tubes may not be necessary in all cases as the pressurised gas in the tubes may act as a splint to prevent or at least restrict crushing of the tubes 3350 during use. A crush resistant tube may be advantageous where only a single tube 3350 is present as if the single tube becomes blocked during use the flow of gas would be restricted and therapy will stop or reduce in efficacy.

In certain forms of the technology, one or more portions of the tubes 3350 may be rigidised by one or more rigidising or stiffening elements. Examples of rigidising elements include: sections of the tubes 3350 that are comparatively thicker than other sections; sections of the tubes 3350 that are formed from a material that is comparatively more rigid that the material forming other sections; and a rigid member attached to the inside, outside or embedded in a section of tube. The use of such rigidising elements helps to control how the positioning and stabilising structure 3300 will function in use, for example where the tubes 3350 is more likely to deform if forces are applied to them and where the shape of the tubes 3350 is more likely to be maintained if forces are applied. The selection of where such rigidising elements are positioned in the tubes 3350 can therefore help to promote comfort when the patient interface 3000 is worn and can help to maintain a good seal at the seal-forming structure 3100 during use. Rigidising or stiffening elements may be in positioning and stabilising structures 3300 which are configured to support relatively heavy seal-forming structures such as full face or oro-nasal cushion assemblies.

The tubes 3350 in the form of the technology shown in FIGS. 8A-9C and 12A-F have a length of between 15 and 30 cm each, for example between 20 and 27 cm each. In one example each of the tubes are around 26 cm long. In another example each of the tubes is around 23 cm long. The length of the tubes is selected to be appropriate for the dimensions of the heads of typical patients, for example the distance between the region proximate the top of the head where the upper end of the tubes 3350 are situated, and the region proximate the openings to the patient's airways at which the lower end of the tubes 3350 connect to the cradle cushion module 3150 (or pillows cushion module 3160) when following a generally arcuate path down the sides of the heads and across the patient's cheek region such as is shown in FIGS. 8A-9C or 12A-F. As described in more detail below, the patient interface 3000 is configured so that the length of the tubes 3350 can be varied in some forms of the technology and the above lengths may apply to the tube in a contracted, stretched or neutral state. It will be appreciated that the length of the tubes 3350 will depend on the length of other components in the patient interface 3000, for example the length of arms of a T-shaped conduit to which the upper ends of tubes 3350 connect and/or the size of the plenum chamber 3200.

5.3.2.1.1 Positioning of Headgear Components

Each tube 3350 may be configured to receive a flow of air from the connection port 3600 on top of the patient's head and to deliver the flow of air to the seal-forming structure at the entrance of the patient's airways. In the example of FIGS. 8A-9C and 12A-F, the at least one tube 3350 extends between the seal-forming structure 3100 and the connection port 3600 across the patient's cheek region and above the patient's ear, i.e. a portion of tube 3350 that connects to the cushion module overlays a maxilla region of the patient's head and a portion of tube 3350 overlays a region of the patient's head superior to the otobasion superior on the patient's head. Each of the one or more tubes 3350 may also lie over the patient's sphenoid bone and/or temporal bone and either or both of the patient's frontal bone and parietal bone. The connection port 3600 and elbow 3610 may be located in use over the patient's parietal bone, frontal bone or the junction therebetween.

The exemplary form of the technology illustrated in FIGS. 8A-9C and 12A-F has tubes 3350 which curve around the upper part of the patient's head from the upper end of the tubes 3350 that connect to elbow 3610 on top of the head to the point at which the strap 3310 connects to the tubes 3350 with relatively little curvature in the sagittal plane. In between the point at which the strap 3310 connects to the tubes 3350 and the lower ends of the tubes 3350 at which they connect with the cradle cushion module 3150 in front of the patient's airways under the nose, the tubes 3350 curve forwards between the patient's ears and eyes and across the cheek region. The radius of curvature of this section of the tubes 3350 may be in the range 60-100 mm, for example 70-90 mm, for example 80 mm. The lower end of the tubes 3350 and the section of the tubes 3350 at which the strap 3310 connects to the tubes 3350 may subtend an angle in the range 65-90°, for example 75-80°. The actual curvature present in the portions of the tubes 3350 superior to the strap 3310, and the actual curvature in the portions of the tubes 3350 inferior to the strap 3310, depends on patient setup and in practice will vary depending on the shape and size of the patient's head and the patient's preferences.

The degree to which the patient interface 3000 fits an individual patient can be altered by varying the length of the tubes 3350 and, alternatively or additionally, by altering the position of the patient interface 3000 or portions thereof on the patient's head. For example, a patient interface 3000 having tubes 3350 of a certain length can be adjusted to better fit a patient by moving portions of the positioning and stabilising structure 3300 in the posterior or anterior direction on the patient's head. For example, positioning the junction of the tubes 3350 above the patient's head further forward (i.e. in the anterior direction) enables a patient interface 3000 having tubes 3350 of a certain length to fit a larger head than if the junction of the tubes 3350 is positioned further backward (i.e. in the posterior direction). In most patient, if the junction of the tubes 3350 is positioned forwardly, the superior portions of the tubes 3350 lie over a smaller portion of the patient's head than if the junction of the tube 3350 is positioned rearwardly.

In certain forms of the present technology the patient interface 3000 is configured such that the connection port 3600 can be positioned in a range of positions across the top of the patient's head so that the patient interface 3000 can be positioned as appropriate for the comfort or fit of an individual patient. One way this can be achieved so that the seal-forming structure 3100 forms an effective seal with the patient's face irrespective of the position of the connection port 3600 on the patient's head is to de-couple movement of the upper portion of the patient interface 3000 from the lower portion of the patient interface 3000. Such de-coupling can be achieved using, for example, mechanisms that allow parts of the gas delivery tubes 3350 to easily move or flex relative to other parts of the patient interface 3000. Such mechanisms will be described below.

In a certain form of the present technology, the patient interface 3000 is configured such that the connection port 3600 is positioned approximately at a top point of the patient's head. The connection port 3600 may be positioned in the sagittal plane and aligned with the otobasion superior points in a plane parallel to the coronal plane. The otobasion superior points are identified in FIG. 2D. As will be described below, in some forms of the technology, the positioning and stabilising structure 3300 is configured to be worn in different positions, with the effect that the connection port 3600 may be positioned proximate the top of the patient's head in the sagittal plane up to around 20 mm forward or 20 mm rearward of the otobasion superior points.

In some examples of the present technology, the connection port 3600 may be positioned in the sagittal plane and aligned with a junction between the frontal bone and the parietal bones. The connection port 3600 may be positioned approximately over the junction of the coronal suture and the sagittal suture. In this configuration, the superior portions of the tubes 3350 may lie over and/or along a portion of the coronal suture. However, as mentioned above the patient has the ability to move the connection port 3600 anteriorly or posteriorly in order to adjust the fit of the patient interface 3000.

An advantage provided by the tubes 3350 overlying the patient's head slightly anterior to the superior-most point (e.g. at or proximate the coronal suture) is that the risk of the tubes 3350 riding in a posterior direction in use may be reduced. In many patients there may be a recess or "divot" where the coronal suture meets the sagittal suture. The positioning and stabilising structure 3300 may be particularly stable when tubes 3350 lie within this divot. Accordingly, in some examples the tubes 3350 are configured with appropriate curvature and/or ability to curve in order to lie over the coronal suture.

As described above, in some examples of the present technology the patient interface 3000 comprises a seal-forming structure 3100 in the form of a cradle cushion which lies generally under the nose and seals to an inferior periphery of the nose. The positioning and stabilising structure 3300 may be structured and arranged to pull the seal-forming structure 3100 into the patient's face under the nose with a sealing force vector that has a posterior and superior direction (e.g. a posterosuperior direction). A sealing force vector with a posterosuperior direction may facilitate the seal-forming structure 3100 forming a good seal to both the inferior periphery of the patient's nose and the anterior-facing surfaces of the patient's face on either side of the patient's nose and the upper lip.

In some examples, the positioning and stabilising structure 3300 may in use apply a sealing force vector having a posterosuperior direction at an angle of approximately 35° with respect to the patient's Frankfort horizontal. The superior portions of the tubes 3350 (e.g. the portions of the tubes 3350 superior to the strap 3310) may be oriented vertically, and the rear headgear strap 3310 may extend from the tubes 3350 in a posteroinferior direction at an angle of approximately 35° with respect to the patient's Frankfort horizontal. In this particular setup, there is an angle of 125° formed between the strap 3310 and the superior portions of the tubes 3350 where the strap 3310 connects to the tubes 3350.

FIG. 8D shows a side view of a patient wearing the patient interface 3000. Certain forces acting on a point 3308 above each of the patient's ears proximate where the strap 3310 connects to the tubes 3350 are identified in FIG. 8D. The superior portions of the tubes 3350 may apply a vertical force 3301 on the point 3308 resulting from headgear tension. The vertical force 3301 may have a substantially vertical direction. The inferior portions of the tubes 3350 (e.g., between the seal-forming structure 3100 and the connection to the rear headgear strap 3310) may apply an anteroinferior force 3303 on this point 3308 in an anterior inferior direction at an angle of approximately 125° to the vertical force 3301 applied by the superior portions of the tubes 3350. The anteroinferior force 3303 may be equal in magnitude and opposite in direction to the sealing force at which the seal-forming structure 3100 is pulled into the patient's face under the nose. To balance the forces, the strap 3310 applies a posteroinferior force 3302 in a posteroinferior direction at an angle of approximately 125° to the vertical force 3301 applied by the superior portions of the tubes 3350. Accordingly, there is an angle of approximately 110° between the anteroinferior force 3303 applied to the point 3308 along each tube 3350 above the patient's ear and the posteroinferior force 3302 applied by the strap 3310.

A sealing force vector of 35° may be considered optimal for many patients when the positioning and stabilising structure 3300 is used with a cradle cushion. Additionally, the directions of the forces described above applied by each portion of the positioning and stabilising structure 3300 may be considered ideal. However, it will be appreciated that that, in practice, the actual directions of the forces applied by each portion of the headgear will vary to accommodate the particular anatomy and preferences of each patient.

For example, in many examples the positioning and stabilising structure 3300 may be configured such that the superior portions of the tubes 3350 lie across the patient's head slightly anterior to a superior-most point. For some patients this may result in the tubes 3350 being angled slightly anteriorly rather than aligned vertically (e.g. in the coronal plane) in order to lie within a slight recess at or proximate the coronal suture of the skull. In such an example, the tension in the strap 3310 could be adjusted by the patient to balance the forces and achieve the optimal sealing force vector.

In some examples, the positioning and stabilising structure 3300 may be configured to apply a force on the seal-forming structure 3100 in a posterosuperior direction at an angle that bisects an angle formed between the upper lip and the columella (e.g. the surfaces forming the nasolabial angle).

In certain examples of the present technology, the tubes 3350 are configured to receive the strap 3310 at the locations superior to and proximate the patient's ears. If the strap 3310 connects to the tubes 3350 to high with respect to the patient's head, the strap 3310 may have a tendency to ride up the back of the patient's head. Additionally, the strap 3310 could form too large of an angle with respect to the superior portions of the headgear tubes 3350, resulting in the necessity for the patient to tighten the strap 3310 excessively, which could result in both excessive tension in the positioning and stabilising structure 3300 and make the strap 3310 more likely to ride up the back of the patient's head.

Accordingly, it is advantageous for the connection between the strap 3310 and the tubes 3350 to be provided as low as possible but spaced from the top of the patient's ear sufficiently that upon tightening of the strap 3310, the tubes 3350 are not pulled into contact with the patient's ears.

5.3.2.1.2 Headgear Tube Fluid Connections

The two tubes 3350 are fluidly connected at their inferior ends to the plenum chamber 3200. In the examples of FIGS. 8A-9C and 12A-F, the tubes 3350 form a fluid connection with the cushion module 3150 and seal-forming structure 3100. In certain forms of the technology, the connection between the tubes 3350 and the cushion module 3150 is achieved by connection of two rigid components so that the patient can easily connect the two components together in a reliable manner. The tactile feedback of a 're-assuring click' or like sound may be easy for a patient to use or for a patient to know that the tube has been correctly connected to the cushion module 3150. In one form, the tubes 3350 are formed from silicone and the lower end of each of the silicone tubes 3350 is overmolded to a rigid connector made, for example, from polypropylene, polycarbonate, nylon or the like. The rigid connector may comprise a male mating feature configured to connect to a female mating feature on the cushion module 3150. Alternatively, the rigid connector may comprise a female mating feature configured to connect to a male mating feature on the cushion module 3150. The same manner of connection by which the tubes 3350 are connected to the cushion module 3150 may also be applied to the connection between the tubes 3350 and the cushion module 3150, or another plenum chamber 3200 or seal-forming structure 3100.

In another embodiment a compression seal is used to connect each tube 3350 to the cradle cushion module 3150. For example, a resiliently flexible (e.g. silicone) tube 3350 without the rigid connector may need to be squeezed slightly to reduce its diameter so that it can be jammed into a port in the plenum chamber 3200 and the inherent resilience of the silicone pushes the tube 3350 outwards to seal the tube 3350 in the port in an air-tight manner. In a hard-to-hard type engagement between the tube 3350 and port, a pressure activated seal such as a peripheral sealing flange may be used. When pressurised gas is supplied through the tubes 3350 the sealing flange is urged against the join between the tubes and the inner circumferential surface of the port of the plenum chamber 3200 to enhance the seal between them. If the port is soft and a rigid connector is provided to the tube 3350, the pressure activated seal as described earlier may also be used to ensure the connection is air-tight. In another example, each tube 3350 is formed from a resiliently flexible (e.g. silicone) material which is over moulded to a rigid connector such that the resiliently flexible material fits over the rigid connector and itself functions as a gasket to seal the connection between the tube 3350 and the cradle cushion module 3150 around a periphery of an air flow passage from the tube 3350 into the plenum chamber 3200 of the cradle cushion module 3150.

Similar connection mechanisms may be used to fluidly connect the tubes 3350 with a T-shaped top member defining the connection port 3600 or connectable to the connection port 3600 in some forms of the technology. In one embodiment, a swivel elbow connected at the connection port 3600 is rotatable in order to drive a port size adjustment mechanism that decreases or increases the size of the ports into which tubes 3350 are inserted in order to improve the fit of the tubes through an increase or decrease of compressive forces and to reduce unintended leakage.

5.3.2.1.3 Extendable Concertina Structure

The patient interface 3000 may comprise one or more extendable tube sections. In some examples, an extendable tube section comprises an extendable concertina structure 3362. The patient interface 3000 may comprise a positioning and stabilising structure 3300 including at least one gas delivery tube comprising a tube wall 3352 having an extendable concertina structure 3362. For example, the patient interface 3000 shown in FIGS. 8A-9C and 12A-F comprises tubes 3350, the superior portions of which comprise extendable tube sections each in the form of an extendable concertina structure 3362.

Each extendable concertina structure 3362 may comprise a portion of the tube 3350 having one or more folding portions, pleats, corrugations or bellows to form an extendable portion of the tube 3350. In the example shown in FIGS. 8A-9C, the extendable concertina structures 3362 each take the form of an extendable concertina structure. The extendable concertina structures 3362 are separated by the elbow 3610 and connection port 3600. The extendable concertina structures 3362 are able to change in length. In particular, each extendable concertina structure 3362 is able to extend or contract in order to change the length of the respective tube 3350.

In some examples, each gas delivery tube 3350 at the extendable concertina structure 3362 may comprise a cross-section having a width and a height, where the width is larger than the height and is aligned in use substantially with the anterior-posterior directions. For example, the patient interface 3000 illustrated in FIGS. 8A-8C comprises extendable concertina structures 3362 each having a cross-sectional width greater than a cross-sectional height, the width being the dimension aligned with the anterior and posterior directions of the illustrated patient 1000. In this example, the width is about twice as large as the height. That said, in this example the width reduces along the length of the extendable concertina structure 3362. At a superior, or medial, end of each extendable concertina structure 3362, the width of the tube wall forming the extendable concertina structure 3362 is relatively larger and is a similar size to a ring in which the swivel elbow 3610 is received in the tube 3350. At an inferior, or lateral, end of each extendable concertina structure 3362, the width of the tube wall is relatively smaller and is a similar size to the width of the non-extendable tube section 3363. An extendable concertina structure 3362 that changes in width between the larger tube size of the connection to the elbow 3610 and the smaller tube size of the non-extendable tube sections 3363 may provide for a sleek and contiguous tube 3350 that may be more comfortable and/or aesthetically appealing (which may improve patient compliance with therapy).

5.3.2.1.3.1 Bendability

In some examples of the present technology, portions of the positioning and stabilising structure 3300 are configured to be more resistant to bending in or about some directions or axes than in or about others.

For example, a superior portion of each tube 3350 of the positioning and stabilising structure 3300 shown in FIGS. 8A-9C may be more bendable in a particular direction in comparison to an orthogonal direction. Each gas delivery tube 3350 of the positioning and stabilising structure 3300 may comprise a superior tube portion 3304 configured to overlie a superior region of the patient's head in use (as illustrated in FIGS. 8A-C). In the illustrated example, the superior tube portion 3304 includes the extendable concertina structure 3362. In other examples of the present technology, the superior tube portion 3304 may comprise an alternative extendable tube structure (such as one of the options disclosed in PCT Patent Publication No. WO 2017/124155, the entire contents of which are incorporated herein by reference) or may be non-extendable.

The superior tube portion 3304 comprises a first end 3305 and a second end 3306. In this example the first end 3305 is configured to overlie or lie against a superior portion of the patient's head, at approximately sagittal plane of the patient's head (e.g. approximately top and centre of the patient's head). The second end 3306 is configured to overlie the patient's head laterally from the first end 3305 (e.g. closer to the side of the patient's head). In some examples, if the superior tube portion 3304 is not particularly long, the second end 3306 may lie laterally with respect to the first end 3305 but may not lie particularly inferior to the first end 3305. In other examples, if the superior tube portion 3304 is longer, the second end 3306 may lie both laterally and inferiorly to the first end 3305. FIG. 13 shows a portion of another example of a positioning and stabilising structure 3300. The positioning and stabilising structures of FIGS. 8A-9C and also FIG. 13 are able to bend about multiple axes. For example, the positioning and stabilising structure 3300 in FIG. 13 is able to drape down over the patient's head and also curve in the anterior and posterior directions. As illustrated in FIG. 13, the superior tube portion 3304 is bent about two axes.

The superior tube portion 3304 may also comprise one or more stiffened portions between the first end 3305 and the second end 3306. The stiffened portion(s) may be configured to provide a higher resistance to relative movement between the first end 3305 and a second end 3306 in an anterior and/or posterior direction than in a superior and/or inferior direction.

When the patient dons the positioning and stabilising structure 3300, the superior tube portion 3304 may have a relatively low resistance to bending in the vertical directions such that the second end 3306 is able to move inferiorly with respect to the first end 3305. This advantageously enables the superior tube portion 3304 to "drape" downwardly over the top of the patient's head to the side of the patient's head. A relatively high degree of bendability and the superior/inferior directions may be advantageous in enabling the superior tube portion 3304 to conform to the curvature of the patient's head.

Additionally, the superior tube portion 3304 may have a relatively higher resistance to bending in the horizontal directions such that the first end 3305 does not unintentionally move anteriorly and/or posteriorly with respect to the second end 3306. This advantageously enables the superior tube portion 3304 to remain in a desired position across the top of the patient's head. With a lower resistance to bending towards the anterior and/or posterior directions, the superior tube portion 3304, and in particular the connection port 3600, may be less likely to ride forward or backward along the top of the patient's head in use. This resistance to a forward or backward movement of the superior tube portion 3304 is particularly advantageous for the patient interface 3000 given the connection to the air circuit 4170 is provided atop the patient's head, meaning tube drag forces may act directly on the superior tube portion 3304.

In some examples, the superior tube portion 3304 may comprise a shape which inherently provides the advantageous resistance to bending. For example, the superior tube portion 3304 may comprise a rectangular cross-section one of the parallel long sides configured to lie against the surfaces of the patient's head. The long sides of the rectangular cross section provide a relatively large resistance to bending of the superior tube portion in directions parallel to the long sides (e.g. the anterior and/or posterior directions in use). However, the short sides of the rectangular cross section may not provide such a large resistance to bending of the superior tube portion 3304 and directions parallel to the short sides (e.g. the inferior and/or superior directions in use). It will be appreciated that the cross-section of the superior tube portion 3304 may not be perfectly rectangular. For example, the corners and/or short sides may be rounded.

The stiffened portion may be formed by one or more rigidising structures formed by or provided to the tube wall of the tube 3350. In the examples shown in FIGS. 8A-10J, the stiffened portion is formed by a plurality of ridge connecting portions 3370 that are configured to resist separation of adjacent ridges formed by folds in the tube wall. In particular, the stiffened portion is formed by a series of ridge connecting portions 3370 along both the anterior side of the superior tube portion 3304 and the posterior side of the superior tube portion 3304. A tube 3350 that comprises stiffened portions on both the anterior and posterior sides of the tube 3350 may advantageously have a higher resistance to bending towards both the anterior and posterior sides of the tube 3350. However, in some examples a stiffened portion is provided to only one of the anterior or posterior sides of the tube 3350 since, depending on the stiffness, a stiffened portion on one side only may provide a sufficient resistance to bending towards both directions.

In some examples the stiffened portion of a tube 3350 may be provided to an extendable portion of the superior tube portion 3304. In the example illustrated in FIGS. 8A-10J, the extendable portion comprises an extendable concertina structure 3362 formed in a tube wall of the tube 3350, the extendable concertina structure 3362 comprising a plurality of ridges 3372 and a plurality of grooves 3373, as will be described in more detail below. In this example, the stiffened portion comprises a plurality of ridge connecting portions 3370 formed in the tube wall, each of the plurality of ridge connecting portions 3370 connecting a pair of adjacent ridges 3372. The stiffening effects of the ridge connecting portions 3370 are described in more detail below.

In other examples of the present technology, the patient interface 3000 may comprise tubes 3350 having stiffened portions formed by structures other than ridge connecting portions. In some examples, portions of the tubes 3350 (e.g. anterior and/or posterior portions) may comprise stiffened portions being stiffened with one or more rigidising elements. The tubes 3350 may be rigidised with one or more rigidising components having a higher stiffness than the tube 3350 embedded within the tube wall. For example, the tube wall may be overmoulded to an elongate bar or rod formed from a material stiffer than the tube wall. In other examples, a stiffened portion of the tube wall may be provided by further features of the geometry of the tube wall. In one example the tube wall may comprise a greater material thickness at the anterior and/or posterior sides of the tube 3350. In another example, the tube wall may comprise a reduced groove depth (or ridge height) at stiffened portions of the tubes 3350.

5.3.2.1.3.2 Ridges and Grooves

The extendable concertina structure 3362 forming each extendable tube section comprises a plurality of ridges 3372 and a plurality of grooves 3373, as shown in FIGS. 10D-10J. The ridges 3372 and grooves 3373 are alternatingly formed into the wall of each tube 3350 to form a concertina structure. An alternating series of ridges and grooves will be understood to refer to a series in which a groove is provided between each pair of ridges and a ridge is provided between each pair of grooves (e.g. ridge, groove, ridge, groove and so on).

The alternating ridges 3372 and grooves 3373 may function like folds or bellows able to fold and unfold independently or in concert to shorten or lengthen the extendable concertina structure 3362 and hence the respective tube 3350. A large groove depth (or ridge height) may provide for a more extendable tube 3350. When tension is applied to the tubes 3350, the ridges 3372 and grooves 3373 of the extendable concertina structures 3362 may be pulled away from each other which straightens out the tube wall, lengthening the tubes 3350. In this example, the extendable concertina structure 3362 is biased to an original (e.g. unextended) length. Upon release of headgear tension the ridges 3372 and grooves 3373 are biased back to an original configuration in which each extendable concertina structure 3362 and the tubes 3350 have original lengths.

In addition to facilitating a change in the length, the ridges 3372 and grooves 3373 may also facilitate a change in shape of the extendable concertina structure 3362 of each tube 3350. In some examples of the present technology, a first series of alternating ridges 3372 and grooves 3373 is provided to a first side of the tube 3350 in the extendable concertina structure 3362 (e.g. a patient-contacting side), while a second series of alternating ridges 3372 and grooves 3373 is provided to a second, opposite, side of the tube 3350 (e.g. a non-patient-contacting side). The extendable concertina structure 3362 may facilitate bending of the tube 3350 as the ridges 3372 and grooves 3373 are able to move with respect to each other by differing degrees on the different sides of the tube 3350. For example, on the first side of the tube 3350 the ridges 3372 and grooves 3373 may contract while on the second side of the tube 3350 the ridges 3372 and grooves 3373 may expand, with the result being that the tube 3350 bends in the extendable concertina structure 3362. Alternatively, the ridges 3372 and grooves 3373 on both the first side and the second side may expand, in use, but the ridges 3372 and groove 3373 on the first side may expand less to enable to tube 3350 to bend (e.g. curve) in the direction of the first side, for example to conform or wrap to (e.g. drape over) the patient's head while extending in length.

In some examples, the first alternating series of ridges 3372 and grooves 3373 may have a lesser extension stiffness (e.g. a lesser force required to achieve a change in unit length) than the second alternating series of ridges 3372 and grooves 3373. The reduced extension stiffness in the non-patient-contacting side of the extendable concertina structure 3362 may advantageously facilitate bending/curvature in the tubes 3350 in use by enabling the outboard side of the tube 3350 to extend to cover a greater arc length then the inboard side of the tubes 3350 in the extendable concertina structure 3362. While the extension stiffness of both the first and the second alternating series of ridges 3372 and grooves 3373 may differ from one another, the extension stiffnesses of each may be selected to achieve a desired overall extension stiffness of the extendable concertina structure 3362.

The ridges 3372 and grooves 3373 may each be formed along a portion of the tube wall around a majority of a longitudinal axis of the tube 3350, such as on all, or almost all, of the sides of the tube 3350. This may enable the extendable concertina structure 3362 to bend about multiple axes. As shown in FIGS. 10H-10J and FIG. 13, extendable concertina structures 3362 according to examples of the present technology may enable the tubes 3350 in multiple axes. FIGS. 10H and 10I show an extendable concertina structure 3362 bending in the superior-inferior directions (e.g. to drape over a patient's head), FIG. 10J shows the extendable concertina structure 3362 bending in the anterior-posterior directions (e.g. to enable the tubes 3350 to lie over the top of the patient's head at different locations) and FIG. 13 shows an extendable concertina structure 10J bending in both the superior-inferior and anterior-posterior directions at the same time.

In some examples, each of the ridges 3372 and grooves 3373 are substantially straight. In other examples, the ridges 3372 and/or grooves 3373 may comprise one or more arcuate portions.

As shown in FIG. 10D, each ridge 3372 comprises a central curved ridge portion 3374. That is, each ridge 3372 comprises an accurate portion in the centre thereof. However, at the ends of each ridge 3372 are straight ridge portions 3375. Accordingly, each of the ridges 3372 comprises a pair of straight ridge portions 3375 provided at opposite ends of the ridge 3372.

Similarly, each groove 3373 comprises a curved groove portion 3376 central the respective groove. The centre of each groove 3373 is therefore accurate. Additionally, at the end of each groove 3373 is a straight groove portion 3377. Each of the grooves 3373 comprises a pair of straight groove portions 3377 provided at opposite ends of the groove 3373. Each of the curved groove portions 3376 may comprise curvature matching or defined by the curvature of the pair of adjacent ridges 3372, in particular the curvature of the curved ridge portions 3374.

Each of the ridge connecting portions 3370 connects a respective adjacent pair of ridges 3372 at the straight ridge portions 3375 of the pair of ridges 3372. The straight groove portions 3377 may each be defined between adjacent straight ridge portions 3375 on either side along the length of the tube 3350 and a ridge connecting portion 3370 either superior or inferior to the straight groove portion 3377 (as the case may be for each straight groove portion 3377, depending on whether it is on a superior or inferior side of the tube 3350).

While the extendable concertina structure 3362 comprises ridges 3372 and grooves 3373 on an exterior of the gas delivery tube 3350, the folds forming the extendable concertina structure 3362 may also form ridges and grooves interior to the gas delivery tube 3350 (e.g. as a result of the folds forming a wavelike shape in the tube wall, such as a sinusoidal shape, square wave or other waveform). FIG. 10B shows the particular wavelike shape formed in the tube walls. As shown in FIG. 10B, the extendable concertina structure 3362 comprises folds forming interior ridges 3382 and interior grooves 3383. In particular, the folds in the tube wall form, interior to the tubes 3350, a first alternating series of interior ridges 3382a and interior grooves 3383a along the non-patient-contacting side of the tube 3350. Additionally, the folds form a second alternating series of interior ridges 3382b and interior grooves 3383b along the patient-contacting side of the tubes 3350.

Each interior groove 3383a of the first alternating series may be provided opposite a respective interior groove 3383b of the second alternating series across the interior of the tube 3350 to form a plurality of opposing groove pairs. That is, each interior groove 3383a on the non-patient-contacting side of the tube 3350 may be paired with an opposing interior groove 3383b on the patient-contacting side. As illustrated in FIG. 10B, each opposing groove pair comprises a first interior groove 3383a and a second interior groove 3383b. In this example, the first interior groove 3383a comprises a greater groove depth than the second interior groove 3383b. The greater groove depth of the first interior groove 3383a in each opposing groove pair results in the first alternating series of ridges and grooves having a lower extension stiffness than the second alternating series. In other examples of the present technology, the relatively lower stiffness of the ridges and grooves forming the first alternating series may be provided by stiffening the second alternating series of ridges and grooves. In one example, ridge connecting portions 3370 (described separately below) are provided to the tube wall to connect pairs of adjacent ridges. In another example, the second alternating series of ridges and grooves are formed by a stiffer material than the first alternating series (e.g. a different material having a higher stiffness or, in the case of the tube being formed from silicone, a region of silicone having a higher Durometer, etc.). In a further example, the second alternating series of ridges and grooves may be stiffened with a rigidising component.

In the illustrated example, the tube wall of the tube 3350 comprises a greater material thickness at a base of the second interior groove 3383b of each opposing groove pair than at a base of the first interior groove 3383a of the respective groove pair. The greater material thickness forming the basis of the second interior groove 3383b of each of those in groove pair reduces the groove depth of the second interior groove 3383b. The reduced groove depth reduces the extendibility of the extendable concertina structure 3362 on the side having the second alternating series of ridges and grooves.

As shown in FIG. 10B, the material thickness of the tube wall at the base of each interior groove 3383b of the second alternating series reduces along the length of the tube 3350 from the first end proximate the connection port 3600 to a second end. Additionally, the material thickness of the tube wall at the base of each interior groove 3383a of the first alternating series is substantially constant along the length of the tube 3350. The groove depth of the interior grooves 3383a and 3383b of the first and second alternating series of interior ridges 3382 and interior grooves 3383 reduces along the length of the gas delivery tube 3350 from the first end adjacent the connection port 3600 to the second end. The reduction in groove depth on both sides of the tube 3350 along the length of the extendable concertina structure 3362 facilitate a change in size of the tube 3350 between the larger connection port 3600 and the smaller non-extendable tube section 3363. While the groove depth is generally lesser at the second end in comparison to the first end, for each opposing groove pair, the second interior groove 3383b on the second, patient-contacting side, of the extendable concertina structure 3362 has a lesser groove depth then the opposing first interior groove 3383a on the first, non-patient-contacting side.

In this example, the first interior groove 3383a of each opposed groove pair is joined to the second interior groove 3383b of the respective opposed groove pair at sides of the tube 3350 between the non-patient-contacting side and the patient-contacting side. That is, tube 3350 is grooved all of the way around the interior of the tube wall. The first interior groove 3383a and second interior groove 3383b of each opposed groove pair are therefore contiguous. Similarly, each interior ridge 3382a of the first alternating series of interior ridges 3382a and interior grooves 3383a contiguous with an opposing interior ridge 3382b of the second alternating series interior ridges 3382b and interior grooves 3383b.

5.3.2.1.3.3 Ridge Connecting Portions

As shown in FIGS. 10D-10J, the extendable concertina structures 3362 also comprise a plurality of ridge connecting portions 3370 provided to the tube wall of the gas delivery tube 3350. Each of the ridge connecting portions 3370 connects a pair of adjacent ridges 3372. The ridge connection portions 3370 may each comprise an integrally formed portion of the tube wall. Each ridge connection portion 3370 may be formed into the tube wall. Each ridge connection portion 3370 connects two or more adjacent ridges 3372 and is configured to resist separation of the ridges 3372. The ridge connection portions 3370 may not prevent separation of the ridges 3372 but may increase the stiffness of the extendable concertina structure 3362.

One function of the ridge connecting portions 3370 is to reduce the ability of the extendable concertina structures 3362 to extend. While the extendable concertina structures 3362 are intended to extend, and there are be advantages associated with tubes 3350 that are extendable in length, an excessively extendable tube 3350 may be difficult for a patient to use comfortably and securely. The ridge connecting portions 3370 therefore temper the ability of the extendable concertina structure 3362 to increase in length but do not prevent it from extending at all. In the illustrated example, the ridge connecting portions 3370 in combination with the ridges 3372 and grooves 3373 form extendable concertina structures 3362 that facilitate sufficient extension to the lengths of the tubes 3350 to improve the ability of the positioning and stabilising structure 3300 to fit to a range of patient head sizes without being so flexible that sufficient tension and sealing force cannot be achieved.

Each pair of adjacent ridges 3372 of an extendable concertina structure 3362 may be connected by at least one ridge connecting portion 3370. Alternatively, or additionally, one or more pairs of adjacent ridges 3372 may be connected by two ridge connecting portions 3370. As shown in FIGS. 10D-10J, each pair of adjacent ridges 3372 of the extendable concertina structure 3362 is connected by two ridge connecting portions 3370. Each of the ridge connecting portions 3370 may be spaced centrally between an inferior side of the gas delivery tube 3350 (e.g. a patient contacting side) and a superior side of the gas delivery tube 3350 (e.g. an upwardly and/or outwardly facing side).

Another function of the ridge connecting portions 3370 is that they provide localised stiffening to the extendable concertina structures 3362. Localised stiffening provided to the extendable concertina structure 3362 may be advantageous for headgear tubes 3350 that are intended to easily bend about one axis while having a particular resistance to bending about a different axis.

In some examples, ridge connecting portions 3370 are provided between ridges 3372 and grooves 3373 on sides of the tube 3350 configured to bend less than other sides of the tube 3350. One or more ridge connecting portions 3370 may be located on an anterior-facing side of the gas delivery tube 3350. Alternatively, or additionally, one or more ridge connecting portions 3370 may be located on a posterior-facing side of the gas delivery tube 3350.

In the illustrated example, as shown in FIGS. 10D-10J, ridge connecting portions 3370 are provided to the positioning and stabilising structure 3300 between ridges 3372 on the anterior and posterior sides of the extendable concertina structures 3362. That is, each pair of adjacent ridges 3372 is connected by a ridge connecting portion 3370 located on the anterior-facing side of the gas delivery tube 3350. Additionally, each pair of adjacent ridges 3372 is connected by a ridge connecting portion 3370 located on the posterior-facing side of the gas delivery tube 3350.

Since the ridge connecting portions 3370 are located on the anterior and posterior sides in this example, the ridge connecting portions 3370 provide greater resistance to the extendable concertina structures 3362 bending towards the anterior and posterior directions than towards the superior and inferior directions. This is advantageous since the extendable concertina structures 3362 maintain the ability to bend to fit to the superior and lateral surfaces of the patient's head. This ability to bend results in the tubes 3350 being able to drape down over the patient's head and fit comfortably. Meanwhile, the reduced ability of the extendable concertina structure 3362 to bend towards the anterior and posterior directions may reduce the tendency of the superior-most portion of the positioning and stabilising structure 3300 to move or ride anteriorly or posteriorly in use, which may compromise stability of the patient interface 3000.

The provision of ridge connecting portions 3370 may be advantageous in limiting the extendibility of the extendable concertina structures 3362 without excessively compromising the ability of the extendable concertina structures 3362 to bend about particular axes in which it is advantageous for the extendable tube sections to do so.

Another function provided by the ridge connecting portions 3370 in some examples of the present technology is added resistance to twisting of the extendable concertina structures 3362. As the connection port 3600 is provided between the extendable concertina structures 3362, tube drag forces in some circumstances could act on the tubes 3350 to induce twisting in the extendable concertina structures 3362. The low-profile shape of the tubes 3350 (e.g. the approximately rectangular cross section) may provide resistance to twisting, however the ridge connecting portions 3370 advantageously provide further twisting resistance. The ridge connecting portions 3370 may stiffen the anterior and posterior sides of the extendable concertina structures 3362, functioning as stiffening portions, to reduce the possibility of the tubes 3350 twisting.

In some examples of the present technology, the grooves 3373 of an extendable concertina structure 3362 may be formed as depressions with respect to outer surfaces of the gas delivery tube 3350. In other examples, the ridges 3372 of the extendable concertina structure 3362 may be raised with respect to outwardly facing surfaces of the tube wall and the grooves 3373 may be formed by the spaces between the raised ridges 3372. As shown in FIGS. 10D-10J, the grooves 3373 are formed as depressions with respect to outer surfaces of the tube 3350. The outer surfaces of the tube 3350 from which the grooves 3373 recessed may be contiguous with an outer surface of the non-extendable tube section 3363. An advantage of forming the grooves 3373 as depressions with respect to an outer surface of the tubes 3350 is that the ridges 3372 do not protrude outwardly from beyond the outer surface of the non-extendable tube section 3363. Outwardly protruding ridges may be uncomfortable for the patient.

Also as shown in FIGS. 10D-10J, outwardly facing surfaces of the ridge connecting portions 3370 do not protrude outwardly with respect to a longitudinal axis of the tube further than the ridges 3372. Additionally, each of the ridge connecting portions 3370 comprises an outwardly facing surface contiguous with outwardly facing surfaces of adjacent ridges 3372. It may be less aesthetically pleasing for the ridge connecting portions 3370 to protrude outwardly with respect to the longitudinal axis of the tube 3350 further than the ridges 3372, although they may do so in some examples of the present technology, for example to provide increased bending and/or twisting resistance.

Furthermore, as shown in FIGS. 10D-10J, each of the plurality of grooves 3373 is located between a respective pair of ridge connecting portions 3370. Each respective ridge connecting portion 3370 is located at a respective end of a respective groove 3373. Additionally, each of the plurality of grooves 3373 comprises a groove depth and each of the plurality of ridge connecting portions 3370 comprises a ridge connecting portion height. For each respective set of ridge connecting portions 3370 and grooves 3373, the groove depth is equal to the ridge connecting portion height. That is, the groove depth of each groove 3373 is equal to the ridge connection portion height of each ridge connecting portion 3370 of the respective pair of ridge connecting portions 3370 located at the end of the respective groove 3373. Accordingly, the grooves 3373 are formed as depressions with respect to outer surfaces of the ridge connection portions 3370, ridges 3372 and tube wall of the tube 3350.

The ridge connection portions 3370 may be relatively narrow and rib-like, as shown in the illustrated example. Alternatively, the ridge connection portions 3370 may be thicker (e.g. such that they occupy a larger portion of the anterior and posterior sides of the extendable portions of the tubes 3350).

In the illustrated examples, the ridge connecting portions 3370 are provided on an exterior side of the tubes 3350. That is, the ridge connecting portions 3370 connect ridges 3372 on the outside of the tube wall, rather than on the inside which defines the hollow interior within the tubes 3350. In other examples, the ridge connecting portions 3370 may be provided to an interior side of the tube wall of the tubes 3350. The folds in the tube wall forming the extendable concertina structure 3362 may form, on an interior side of the tube wall, a series of alternating ridges and grooves inverse to the series of ridges 3372 and grooves 3373 formed on the exterior side of the tube wall. That is, the folds forming a ridge 3372 on the exterior of the tube wall may form a groove around an interior of the tube wall. Similarly, the folds forming a groove 3373 on the exterior of the tube wall may form a ridge on the interior of the tube wall.

Ridge connecting portions 3370 may connect between adjacent ridges on either the exterior or the interior of the tube 3350 to resist separation of the ridges. In an example of a positioning and stabilising structure 3300 with ridge connecting portions 3370 on the exterior of the tube 3350, the ridges 3372 on the exterior of the tube are connected and would require greater tension to be separated, while the ridges on the interior of the tube would be more freely separable. Similarly, in an alternatively example of a positioning and stabilising structure 3300 with ridge connecting portions 3370 connecting ridges on the interior of the tube 3350, the ridges on the interior of the tube wall require a greater force to be separated, while the ridges on the exterior of the tube are more freely separable. In some examples, ridge connection portions 3370 connect a combination of interior and exterior rides.

In some examples of the present technology, a single ridge connection portion 3370 connects multiple ridges 3372. In other examples, each ridge connection portion 3370 connects only a single pair of adjacent ridges 3372. In some examples, one or more ridge connection portions 3370 may connect non-adjacent ridges 3372 (e.g. first and last ridges, every second ridge, etc.).

5.3.2.1.4 Non-Extendable Headgear Tubing

The patient interface 3000 may comprise one or more non-extendable tube sections 3363. For example, the patient interface 3000 shown in FIGS. 8A-9C comprises tubes 3350, the inferior portions of which comprise non-extendable tube sections 3363. The non-extendable tube sections 3363 are configured to overlie the patient's cheeks and may be configured to contact the patient's face inferior to the patient's cheekbones. Each non-extendable tube section 3363 may lie on a curve extending inferiorly from the connection between the respective headgear tube 3350 and then extending in a partially anterior and partially medial direction towards the seal-forming structure 3100 in order to avoid the patient's cheek bones.

It is advantageous that the positioning and stabilising structure to 3300 of the patient interface 3000 does not lie over the patient's cheek bones. The regions of a patient's face inferior to the cheekbones are generally more fleshy and a patient may find it more tolerable for the headgear tubes 3350 to lie over these regions of the face. Additionally, since the cheek bone regions of the patient's face are relatively unable to move or deform, the non-extendable tube sections 3363 lie firmly against the fleshy cheek regions. Further, the patient's cheek bones can assist in preventing the inferior portions of the headgear tubes 3350 from riding up over the cheekbones towards the patient's eyes. When the non-extendable tube sections 3363 fit snugly against the patient's cheeks below the cheekbones, the hardness and prominence of the patient's cheekbones may provide a barrier to the headgear tubes 3350 riding up towards the patient's eyes (which could affect stability and/or may obscure the patient's vision).

The cross-sectional shape of the non-extendable tube sections 3363 of the tubes 3350 may be circular, elliptical, oval, D-shaped or a rounded rectangle, for example as described in U.S. Pat. No. 6,044,844. A cross-sectional shape that presents a flattened surface of tube on the side that faces and contacts the patient's face or other part of the head may be more comfortable to wear than, for example a tube with a circular cross-section.

The cross-sectional width and/or height of the tubes 3350 may be in the range 8-25 mm, for example 10-20 mm In some forms in which the tubes have a D-shaped cross-section, for example in the case of the longitudinal section of headgear tubing 3350 shown in FIG. 10C, the tubes have a width in the range 15-25 mm, for example 20 mm, and a height in the range 8-15 mm, for example 10 mm. The height may be considered to be the dimension of the tube extending away from the patient's face in use, i.e. the distance between the patient contacting side 3348 and the outermost part of the non-patient contacting side 3349, while the width may be considered to be the dimension across the surface of the patient's head. The cross-sectional thickness of the material forming the tubes 3350 may be in the range 0.8-1.6 mm, for example 1.0-1.5 mm, for example 1.3 mm The D-shaped cross-sectional tube 3350 has rounded edges 3347 flanking the patient contacting side 3348. Rounded edges in contact with, or proximate to, the patient's skin help the patient interface 3000 to be more comfortable to wear and to avoid leaving marks on, or irritating, the patient's skin. A tube with a D-shaped cross-sectional profile is also more resistant to buckling than other shaped profiles.

A further advantage of the D-shaped cross section of the non-extendable tube sections 3363 of the tubes 3350 is that the non-extendable tube sections 3363 that lie in front of the patient's face in use are more resistant to bending in the vertical directions than in the horizontal directions. The D-shaped cross-section makes the non-extendable tube sections 3363 more resistant to bending parallel to the long axis of the D-shape than to bending perpendicular to the long axis of the D-shape. This is advantageous as the non-extendable tube sections 3363 are more readily able to bend to curve inwardly around the front of the patient's face to the seal-forming structure 3100, yet retain stiffness and the vertical direction to enable the vertical forces applied on the non-extendable tube section 3363 from the extendable concertina structure 3362 to be transferred to the seal-forming structure 3100 in order to provide the necessary sealing force to the seal-forming structure 3100.

The ability to bend inwardly around the front of the patient's face enables the non-extendable tube section 3363 to fit snugly against the patient's cheeks inferior to the patient's cheekbones. As described above in more detail, non-extendable tube sections 3363 that lie snugly under the patient's cheekbones may provide for a more stable seal than non-extendable tube sections 3363 that lie loosely over the patient's cheeks or lie high over the patient's cheekbones.

In other examples, the non-extendable tube sections 3363 may comprise a rectangular shaped cross-section. A rectangular cross-section may provide similar advantages to a D-shaped cross-section. In particular, a rectangular cross-section may provide the non-extendable tube section 3363 with a greater resistance to bending in a direction parallel to the short sides of the rectangular cross section. In other examples, the non-extendable tube sections 3363 may comprise an elliptical or oval-shaped cross-section which would provide similar advantages.

In some examples of the present technology, the non-extendable tube sections 3363 connect to a cradle cushion module 3150 from a low angle. As described above, the headgear tubes 3350 may extend and inferiorly down the sides of the patient's head and then curve anteriorly and medially to connect to a cradle cushion module 3150 in front of the patient's face. The tubes 3350, before connecting to the cradle cushion module 3150, may extend to a location at the same vertical position as or, in some examples, inferior to the connection with the cradle cushion module 3150. That is, the tubes 3350 may project in an at least partially superior direction before connecting with the cradle cushion module 3150. A portion of the tubes 3350 may be located inferior to the cradle cushion module 3150 and/or the seal-forming structure 3100. The low position of the tubes 3350 in front of the patient's face facilitates contact with the patient's face below the patient's cheekbones.

5.3.2.2 Headgear Sizing and Stiffness

Positioning and stabilising structures 3300 may vary in size between different examples of the present technology. Providing different size options for the patient interface 3000 may enable more patients to be accommodated. A loop around the patient's head may be formed by the pair of headgear tubes 3350 and the cradle cushion module 3150 (or the pillows cushion module 3160 or other seal-forming structure 3100) connected between the inferior ends of the tubes 3350. The size of this loop may be varied in order to provide for different size patient interfaces 3000.

In one example, the unextended length of the loop formed by the tubes 3350 and the cradle cushion module 3150, measured along the centreline of the patient-facing side of the loop, may be within the range of 510-610 mm In some examples, the unextended length of this loop may be within the range of 525-600 mm. In some examples the length of this loop may be within the range of 535-590 mm.

In some particular examples, the unextended length of the loop referred to above may be within the range of 528-548 mm, such as within the range of 535-541 mm, for example about 538 mm In further particular examples, the length of this loop may be within the range of 534-554 mm, such as within the range of 539-549 mm, such as about 544 mm or about 547 mm, in examples. In further particular examples, the unextended length of this loop may be within the range of 541-561 mm, such as within the range of 546-556 mm, for example about 551 mm.

In other particular examples, the unextended length of the loop referred to above may be within the range of 564-584 mm, such as within the range of 571-581 mm, such as about 574 or about 579 mm, in examples. In further examples, the unextended length of this loop may be within the range of 577-597 mm, such as within the range of 582-592 mm, such as about 583 mm or about 587 mm, in examples.

The length of the gas delivery tubes 3350, in particular, may be varied in order to provide different sizes of the positioning and stabilising structure 3300. In some examples, the unextended length of the tubes 3350 measured along the centreline of the patient-facing side of the tubes 3350 may be within the range of 500-535 mm, such as between 510-525 mm, such as within the range of 512-522 mm, for example about 517 mm. In further examples, the unextended length of the tubes 3350 may be within the range of 460-500 mm, such as between 470-490 mm, such as within the range of 475-485 mm, for example about 481 mm.

As described in more detail above, in some examples of the present technology, the headgear tubes 3350 comprise extendable portions (e.g. extendable concertina structures 3362). In some examples of the present technology, the extendable portion of a gas delivery tube 3350 (e.g. a single concertina portion on one side of the positioning and stabilising structure 3300) may comprise a stiffness (for extension) within a range of 2-3.5N/10 mm (e.g. 0.2-0.35 N/mm) In particular examples, the extendable portion may comprise a stiffness within a range of 2.5-3N/10 mm (e.g. 0.25-0.3 N/mm) In one example, the extendable portion may comprise a stiffness of approximately 2.75N/10 mm (e.g. 0.275 N/mm). In further examples of the present technology, the extendable portion of a tube 3350 may require between 2.5N and 3N of tension to extend in length by 10 mm and may require between 5N and 5.5N of tension to extend in length by 20 mm. It will be appreciated that, in various examples of patient interfaces 3000 according to the present technology, any of these disclosed stiffnesses may be provided to tubes 3350 having any of the sizes (e.g. lengths) described above.

5.3.2.3 Headgear Straps

In certain forms of the present technology, the positioning and stabilising structure 3300 comprises at least one headgear strap acting in addition to the tubes 3350 to position and stabilise the seal-forming structure 3100 in sealing position at the entrance to the patient's airways. As shown in FIGS., 8A-9C, the patient interface 3000 comprises a strap 3310 forming part of the positioning and stabilising structure 3300. The strap 3310 may be known as a back strap or a rear headgear strap, for example. In other examples of the present technology, one or more further straps may be provided. For example, a patient interface 3000 according to an example of the present technology having a full face or oro-nasal cushion module may have a second, lower, strap configured to overlie the back of the patient's neck.

5.3.2.3.1 Strap

In the example shown in FIGS. 8A-9C, strap 3310 of the positioning and stabilising structure 3300 is connected between the two tubes 3350 positioned on each side of the patient's head and passing around the back of the patient's head, for example overlying or lying inferior to the occipital bone of the patient's head in use. The strap 3310 connects to each tube above the patient's ears. In other embodiments, for example as part of an oro-nasal patient interface, the positioning and stabilising structure 3300 comprises an upper strap similar to strap 3310 and at least one additional lower headgear strap that connects between the tubes and/or cushion module and passes below the patient's ears and around the back of the patient's head. Such a lower headgear strap may also be connected to an upper strap (e.g. a similar to strap 3310).

In certain forms of the technology, the positioning and stabilising structure 3300 comprises a mechanism for connecting a headgear strap to the headgear tubes 3350. The headgear strap may be connected directly or indirectly to the headgear tubes 3350. In the case of the patient interface 3000 shown in FIGS. 8A-9C, for example, a tab 3320 configured to connect to strap 3310 projects outwardly from each headgear tube 3350 in a generally posterior direction. The tabs 3320 have holes in them to receive the ends of strap 3310.

In some forms of the present technology, the strap 3310 is adjustable. For example, in the case of the patient interface shown in FIGS. 8A-9C the strap 3310 is, in use, threaded through a hole in the form of an eyelet in each tab 3320. The length of the strap 3310 between the tabs 3320 may be adjusted by pulling more or less of the strap 3310 through one or both of the tabs 3320. The strap 3310 may be secured to itself after passing through the eyelets in the tabs 3320, for example, with hook-and-loop fastening means. The strap 3310 therefore is able to be adjusted to fit around different head sizes. In some forms of the technology the angle of the strap 3310 relative to the headgear tubes 3350 or patient's head is able to be adjusted to fit around the patient's head at different locations. This adjustability assists the positioning and stabilising structure 3300 to accommodate different head shapes and sizes.

In some forms of the technology, the strap 3310 exerts a force on the headgear tubes 3350 to pull them in an at least partially posterior (e.g. rearwards) direction at the locations of the tabs 3320. The strap 3310 may also exert a force on the headgear tubes 3350 to pull them in an at least partially inferior (e.g. downwards) direction. The magnitude of this force may be adjusted by altering the length of the strap 3310 between the tabs 3320.

In some forms of the technology, such as the example shown in FIG. 8A-9C, the direction of the force applied to the headgear tubes 3350 by the strap 3310 may also be altered. This direction may be altered by adjusting the angle of the strap 3310 relative to the headgear tubes 3350 or patient's head. In some forms of the technology the location at which the strap 3310 exerts a force on the headgear tubes 3350 may be altered by adjusting the location at which the strap 3310 is secured to the headgear tubes 3350.

The adjustability of the magnitude and direction of the force applied to the headgear tubes 3350 by the strap 3310 may advantageously enable the positioning and stabilising structure 3300 to accommodate a range of head sizes and head shapes. The strap 3310 may balance forces in the headgear tubes 3350 which may assist the headgear to maintain its shape and an effective seal to the patient's face, while remaining comfortable.

In some forms of the technology, when worn by a patient, a point on the headgear tubes 3350 near the tab 3320 will receive a generally upward (e.g. superior) force from the upper portion of the headgear tubes 3350 due to tension in the headgear tubes 3350 and, in some examples, due to a biasing mechanism (described in further detail below) acting to keep the headgear secured to the patient's head. Additionally, the point on the headgear tubes 3350 near the tab 3320 may receive a generally forward (e.g. anterior) and downward (e.g. inferior) force caused by a biasing mechanism acting to urge the seal-forming structure 3100 upwards and into the patient's nose. The directions and magnitudes of the forces required for a secure fit and effective seal may vary between patients based on the position of the positioning and stabilising structure 3300 on the head, which may vary due to, for example, differences in head shapes and sizes. In some forms of the technology, the adjustability of the rear headgear strap 3310 enables the forces to be balanced for a range of head shapes and sizes to hold the positioning and stabilising structure 3300 in a comfortable position while maintaining an effective seal.

For example, to provide a larger force acting in the posterior (e.g. rearward) direction on the portions of the headgear tubes 3350 proximate the tabs 3320, the strap 3310 may be adjusted by pulling more of the strap 3310 through the slots in the tabs 3320. Doing so will cause the strap 3310 to shorten in length and, especially if the strap 3310 is elastic, to apply a larger force on the headgear tubes 3350 in the posterior (e.g. rearward) direction. Similarly, the angle of the strap 3310 may be adjusted as required to balance both the vertical and horizontal components of the forces acting on the portions of the headgear tubes 3350 proximate the tabs 3320, across a range of head shapes and sizes.

The strap 3310 may comprise a rectangular cross-section along some or all of its length. Additionally, the strap 3310 may have a profile with one or more rounded edges to provide greater comfort and to reduce the risk of headgear straps marking or irritating the patient. In certain forms of the present technology, a positioning and stabilising structure 3300 comprises a strap 3310 that is bendable and e.g. non-rigid. An advantage of this aspect is that the strap 3310 is more comfortable for a patient to lie upon while the patient is sleeping.

In certain forms of the present technology, a positioning and stabilising structure 3300 comprises a strap 3310 that comprises two or more strap bands separated by a split. For example, as shown in FIGS. 8A-9C and 12A-F, the strap 3310 comprises a split 3313 configured in use to be located against the posterior of the patient's head. A strap 3310 may anchor the patient interface 3000 on the patient's head in a particularly stable fashion in the case of some patient interface designs. The posterior of the patient's head may have complex geometry and the presence of a split 3313 in the strap 3310 may assist the strap to better conform to the back of the patient's head.

5.3.2.3.2 Eyelets

As noted above, each of the gas delivery tubes may comprise an eyelet for connection with a strap. In some examples, the eyelet may be circular. In other examples, the eyelets may be elongate. Alternatively, the eyelets may have a round side and a straight side. The eyelets may be D-shaped, for example. The eyelets in the exemplary patient interface 3000 shown in FIGS. 8A-9C are in the form of slits 3322. In this example, the pair of gas delivery tubes 3350 provide a pair of slits 3322 to which a strap 3310 is able to be connected. That is, the strap 3310 may connect between the eyelets. The strap 3310 may be constructed and arranged to contact, in use, a region of the patient's head inferior to or overlaying an occipital bone of the patient's head. In this example, the slits 3322 are formed in tabs 3320 connected to the tube walls of the tubes 3350.

In some examples of the present technology, the eyelets may be located on each tube 3350 each between 70 mm and 150 mm along the tube 3350 from the centre of the pair of tubes 3350 (e.g. the connection port 3600). In further examples, each eyelet may be located between about 110 mm and 130 mm along each tube 3350 from the centre of the pair of tubes 3350. In particular examples the eyelets may be located between around 120 mm and 125 mm along each tube 3350 from the connection port 3600. In the case of the illustrated positioning and stabilising structure 3300, having slits 3322, the midpoints of the slits are located around 120-125 mm from the centre of the pair of gas delivery tubes 3350.

The exemplary patient interface 3000 shown in FIGS. 8A-9C includes a single rear headgear strap 3310 passing between the slits 3322 and which will typically need to apply a force on the tubes 3350 in a partially inferior and partially posterior direction. To apply a force on the tubes 3350 in the necessary direction, the strap 3310 should wrap low around the back of the patient's head. Typically, the back of the patient's head will generally curve inferiorly and anteriorly over the occipital bone of the skull towards where the head joins the patient's neck.

If the strap 3310 does not lie low enough around the back of the patient's head (e.g. not inferior to the posterior-most point of the patient's head, where the posterior surfaces of the patient's head curve towards the anterior direction and faith partially in an inferior direction) there is a risk that the strap 3310 may ride up the back of the patient's head in use. If the strap 3310 rides up superior to the posterior-most point of the patient's head, the strap 3310 may lie on a region of the patient's head that faces in a partially superior direction. If this occurs, it is possible that tension in the strap 3310 could pull the strap up further, which could result in failure of the positioning and stabilising structure 3300 to provide the necessary sealing force vector to the seal-forming structure 3100 (after which the seal to the patient's face could be compromised and the patient would need to re-don the patient interface 3000).

As illustrated in FIGS. 11A-11C, each of the gas delivery tubes 3350 may comprise a tube wall 3352 defining a hollow interior along the length of the tube 3350 (e.g. forming a conduit). The pressurised flow of air is able to travel from the connection port 3600, through the hollow interior within the tube wall 3352 for delivery to the seal-forming structure 3100.

In the example illustrated in FIGS. 11A-11C, the tube 3350 comprises a tab 3320. In this example the tabs 3320 of the positioning and stabilising structure 3300 are each integrally formed with a respective tube wall 3352 of the tubes 3350. Alternatively, the tabs 3320 may be separate parts assembled with the tube 3350. For example, the tabs 3320 may comprise separate components that movably connect to the tubes 3350 to enable adjustment of the position and/or angle of the tabs 3320. Integrally forming the tabs 3320 with the tube walls 3352 may improve the usability of the positioning and stabilising structure 3300 by reducing the assembly required. Additionally, integrally formed tabs 3320 may enable a seamless connection between tabs 3320 and tube walls 3352, reducing the possibility of the connection causing discomfort to the patient.

In the illustrated example, each of the tubes 3350 comprises an extendable tube section in the form of an extendable concertina structure 3362. Each tab 3320 is joined to the tube wall 3352 of the gas delivery tube 3350 inferior to the extendable tube section. In particular, each tab 3320 is joined to the tube wall 3352 of the gas delivery tube 3350 at a non-extendable tube section 3363 inferior to the extendable tube section. In some examples the tabs 3320 may each have a superior edge 3331 spaced along the length of the tube 3350 from an end of the extendable tube section. In other examples the tabs 3320 may have superior edges 3331 which meet the tube wall 3352 at or proximate an inferior end of the extendable tube section.

In the examples illustrated in FIGS. 11A-11C, the slits 3322 of the tubes 3350 are formed in the tabs 3320. In other examples, slits 3322 may be formed directly into the tube wall 3352 or may be formed into another portion of the positioning and stabilising structure 3300 or a separate component configured to connect to the positioning and stabilising structure 3300.

The slits 3322 may each be spaced posteriorly in use from the tube wall of the respective tube 3350. In particular, each slit 3322 may be spaced posteriorly from slit-adjacent portion 3355 of the tube wall 3352 alongside the respective slit 3322. The slit-adjacent portion 3355 of the tube wall 3352 may be the portion of the tube wall 3352 to which the tab 3320 is connected. More particularly, the slit-adjacent portion 3355 of the tube wall 3352 may be the portion of the tube wall 3352 that is most adjacent to the slit 3322. In some examples, the slit 3322 may be spaced posteriorly with respect to the entire length of the tube wall 3352. The slit 3322 may be located superior to the otobasion superior of the patient's head in use.

In the manner illustrated in FIGS. 8A-8C, each of the tube walls 3352 are configured to overlie the patient's head along a path 3353 passing between an eye and an ear of the patient. A portion of the path 3353 is illustrated in FIGS. 11A and 11B. In some examples, the path 3353 is generally the path on the surfaces of the patient's head over and along which the tube walls 3350 lie. Additionally, the path 3353 may be the path along which gas flowing through the tubes 3350 travels from the top of the patient's head to the seal-forming structure 3100. In practice, the path 3353 may comprise a curve in three-dimensional space (e.g. a space curve), since in some examples the path 3353 may not be confined to a plane. In the illustrated examples, the tubes 3350 track laterally and inferiorly over the sides of the patient's head and then inferiorly, anteriorly and medially to connect with the cradle cushion module 3150.

As illustrated in FIGS. 11A-11C, each of the slits 3322 comprises a superior end 3326 and an inferior end 3327. The superior end 3326 and inferior end 3327 may also be considered first and second ends, respectively. In this example, the superior end 3326 is spaced further from the slit-adjacent portion 3355 of the tube wall 3352 than the inferior end 3327. As shown in FIG. 11A, the superior end 3326 of the slit 3322 is spaced from the tube wall 3352 by a spacing identified with SE in the illustration. The inferior and 3327 of the slit 3322 is spaced from the tube wall 3352 by a spacing identified with IE. As illustrated, the spacing SE is larger than the spacing IE and, accordingly, the superior end 3326 is spaced further from the tube wall 3352 than the inferior end 3327. When a patient has donned a patient interface 3000 including the positioning and stabilising structure 3300, the superior end 3326 is spaced posteriorly with respect to the inferior end 3327. Unless the context clearly requires otherwise, if an end of a slit or eyelet is described as being spaced further from a tube wall than another end of the slit or eyelet, the spacing referred to is to be understood to be with respect to a generally adjacent or closest portion of the tube wall to the slit or eyelet (e.g. a slit-adjacent or eyelet-adjacent portion).

As illustrated in FIG. 11B, the slit 3322 is oriented at an angle with respect to the orientation of the tube 3350 at a slit-adjacent portion 3355 of the tube wall 3352. The slit 3322 is also oriented at an angle with respect to the path 3353 at the slit-adjacent portion 3355 of the tube wall 3352. In this example, the slit 3322 is arcuate between the superior end 3326 and the inferior end 3327. The slits 3322 each have a curved elongate shape. In other examples, each slit 3322 may be straight between the superior end 3326 and the inferior end 3327. The curved, arcuate shape of the slits 3322 may advantageously enable a strap 3310 passing through the slit to centre within the slit 3322 and may also allow the slit 3322 to tolerate some variation in the angle of the strap 3310 passing through the slit 3322, without causing the strap 3310 to bunch up towards one end of the slit 3322.

Illustrated in FIG. 11B is a length axis 3323 of the slit 3322. The length axis 3323 in this example is defined along the general length of the slit 3322 as the slit is elongate. A slit 3322 that is arcuate in shape, such as the slit 3322 shown in FIGS. 11A-C may still comprise a length axis as it is elongate. It will be appreciated that in the case of the slit 3322, the length axis 3323 may not be parallel with every portion of the sides of the slit 3322 but may be defined by the general direction from one end of the slit 3322 to the other. Alternatively, the length axis 3323 of the slit 3322 may be defined by a tangent to the curvature of the slit 3322 at a central portion of the slit 3322.

The slit 3322 may have a posterosuperior-anteroinferior orientation in use. That is, the length of the slit 3322 (e.g. the length axis 3323) may be aligned parallel to a line extending between a posterosuperior direction and an anteroinferior direction. With this orientation, the superior end 3326 of the slit 3322 is spaced posteriorly with respect to the inferior end 3327 of the slit 3322. Illustrated in FIG. 11B is a tangent 3354 to the path 3353 at the slit-adjacent portion 3355 of the tube 3350. As shown, the length axis 3323 of the slit 3322 forms a slit angle 3321 with the tangent 3354 of the path 3353. In this example, the slit angle 3321 is an oblique angle. The oblique angle may be in the range of 5 to 30 degrees. In some examples, the oblique angle may be within the range of 10 to 20 degrees. For example, the oblique angle may be within the range of 12 to 18 degrees. In specific examples, the oblique angle may be about 13 degrees, 15 degrees or 17 degrees. In some examples, the slit 3322 may angled with respect to a longitudinal axis along the length of the extendable concertina structure 3362. In particular, the slit 3322 may be oriented at an angle of between 15 and 45 degrees with respect to a longitudinal axis of the extendable concertina structure 3362 when straightened. For example, this angle may be within the range of 20 and 40 degrees, such as within the range of 22 and 35 degrees. In particular examples, the angle may be about 25 degrees or 31 degrees with respect to the longitudinal axis of the extendable concertina structure 3362 when straightened.

A slit 3322 that is angled posteriorly with respect to the tube wall 3352 or path 3353 (e.g. with the superior end 3326 being spaced further from the tube wall 3352 or path 3353 than the inferior end 3327) may advantageously be better suited to receive the strap 3310 from a lower position around the back of the patient's head. In an ideal set up, the strap 3310 extends from the slit 3322 in a direction perpendicular to the length axis 3323 of the slit 3322. Therefore, a slit 3322 that is more posteriorly angled will better accommodate a strap 3310 that lies low around the back of the patient's head, since it will be angled to receive the strap 3310 from the lower angle. In contrast, a slit 3322 that is oriented closer to a vertical orientation will be angled to receive the strap 3310 from a higher position on the patient's head. Accordingly, a slit 3322 oriented at a larger angle with respect to an adjacent portion of the tube wall 3352 and/or path 3353 may provide some resistance to the strap 3310 riding up the back of the patient's head (e.g. sliding superiorly).

While other methods may be used to reduce the tendency of the strap 3310 to ride up the back of the patient's head (e.g. providing a split in the strap 3310, enabling the patient to tighten the strap 3310 and/or providing the slit 3322 at a low position) providing the slit 3322 at a posteriorly rotated angle to the tube 3350 may provide further resistance to the strap 3310 riding up. In some examples, each slit 3322 may be angled to receive the strap 3310 from a direction in which the strap 3310 lies across a region of the patient's head overlaying an inferior portion of the occipital bone. In further examples, the slit 3322 may be angled to receive the strap 3310 from the direction which the strap 3310 overlays a central or superior portion of the patient's occipital bone.

Each slit 3322 may be oriented perpendicular to the direction from the slit of a strap anchor region against which the strap is anchored around the patient's head. The strap anchor region may be a region overlaying the patient's occipital bone, for example an inferior portion of the occipital bone. In some examples the strap anchor region may be a region of the patient's neck lying inferior to the patient's occipital bone. In some examples, in some examples the strap 3310 may overlay a superior portion of the patient's trapezius muscles or a portion of the patient's neck or head inferior to the occipital bone and the slit 3322 may be angled to receive the strap 3310 from a corresponding direction.

For example, as shown in FIG. 8C, the slit 3322 is angled sufficiently rearward to receive the strap 3310 from a direction in which the strap 3310 lies across a posterior region of the patient's head inferior to an inferior-most portion of the patient's head. The strap 3310 may lie across posterior surfaces of the patient's head that face in an at least partially inferior direction and the slit 3322 may be angled sufficiently posteriorly to receive the strap 3310 from this location. It is advantageous for the strap 3310 to lie across posterior surfaces of the patient's head that face in an at least partially inferior direction since the eyelets are located superior to the posterior-most portion of the strap 3310. Once tension is applied to the strap 3310, the tubes 3350 will exert a partially superior force on the strap 3310, meaning the strap 3310 may be less likely to ride up if anchored against posterior surfaces of the patient's head that face inferiorly.

With reference to FIGS. 11A-11C, the tab 3320 comprises a superior edge 3331 and an inferior edge 3332. In this example, the superior edge 3331 is longer than the inferior edge 3332. The longer superior edge 3331 gives the tab 3320 an asymmetrical shape pointing in more of an inferior direction than the tab 3320 would point if the superior edge 3331 was of an equal length to the inferior edge 3332. The slit 3322 is substantially centred between the superior edge 3331 and an inferior edge 3332. Thus, the asymmetrical shape of the tab 3320 result in the slit 3322 being presented towards more of an inferior direction. This inferior pointing of the tab 3320 may advantageously reduce the tendency of the strap 3310 from riding up the back of the patient's head.

In addition to having an oblique slit angle 3321, the slit 3322 may also be spaced from the tube wall 3352 by a spacing sufficient to further reduce a tendency of the strap 3310 to ride up the back of the patient's head. A generous spacing between a slit or other eyelet and the tube wall 3352 advantageously may reduce the distance between the eyelet and the back of the patient's head. A relatively short distance between the eyelet and the back of the patient's head may reduce the length of the strap 3310 that lies laterally alongside the patient's head extending between the slit 3322 and the posteriorly facing forces of the patient's head. This reduced distance and strap length may advantageously inhibit pivoting of the strap 3310 with respect to the eyelet, thereby reducing the tendency of the strap 3310 to ride upwardly or downwardly in use.

In some examples, the inferior end 3327 of the slit 3322 may be spaced from the tube wall 3352 by at least 5 mm In further examples, the inferior end 3327 of the slit 3322 may be spaced from the tube wall 3352 by at least 7 mm. For example, the inferior end 3327 of the slit 3322 may be spaced from the tube wall 3352 by about 8 mm, or more.

The superior end 3326 of the slit 3322 may be spaced from the tube wall 3352 by at least 8 mm In some examples, the superior end 3326 of the slit 3322 may be spaced from the tube wall 3352 by at least 10 mm. For example, the superior end 3326 of the slit 3322 may be spaced from the tube wall 3352 by 12 mm, or more.

In some examples, a midpoint along the slit 3322 may be spaced from the tube wall 3352 by a spacing within a range of approximately 5 mm to 30 mm. A very large spacing between the eyelet and the tube wall 3352, while advantageous in increasing stability of the strap 3310, may introduce challenges/problems in manufacturability, weight, comfort and aesthetic appear due to the increased size of the tabs 3320. A spacing within the 5-30 mm range, such as with a range of 7 mm to 20 mm, may provide the benefits of stability to prevent the strap 3310 riding up, which avoiding or minimising issues caused by the increased size of the tabs 3320. In further examples this spacing may be within a range of 8 mm to 15 mm, such as within the range of 9 mm to 13 mm. In some particular examples the spacing may be around 9 mm to 11 mm, such as about 9.5 mm or 9.75 mm.

5.3.2.3.3 Trough

FIG. 11C shows a close-up perspective view of one of the tabs 3320 of the positioning and stabilising structure 3300. As illustrated, in some examples, the tab 3320 of the positioning and stabilising structure 3300 may comprise a trough 3324 formed in the tab and located posteriorly to the slit 3322. The trough 3324 may be formed into the body of the tab 3320 in a location underneath the strap 3310. The trough 3324, in this example, is provided between the slit 3322 and a posterior side 3329 of the tab 3320. The tab 3320 may comprise an outwardly facing tab surface 3328 on the side of the tab 3320 facing away from the patient (e.g. in a lateral direction). The tab surface 3328 may be substantially planar in the vicinity of the slit 3322. The trough 3324 may be formed by a portion of the tab 3320 at the trough 3324 having a lesser material thickness than other portions of the tab 3320. The trough 3324 is therefore recessed with respect to the tab surface 3328 in this example.

The trough 3324 may have substantially the same width as the length of the slit 3322. That is, the trough 3324 may have a superior end proximate the superior end 3326 of the slit and may have an inferior end proximate the inferior end 3327 of the slit 3322. In this example, the trough 3324 has substantially the same width as the strap 3310. The trough 3324 is configured to receive the strap 3310. The trough 3324 reduces the total thickness of the strap 3310 and tab 3320. At the location of the trough 3324, the tab 3320 is sandwiched between two layers of the strap 3310 (since the strap is threaded through the slit and looped back on itself). The bulk and/or thickness of the strap 3310 and tab 3320 at this location may create a pressure point or point of discomfort for the patient when sleeping on their side. The trough 3324 may advantageously reduce the layered thickness of components at this location which may reduce the pressure applied to the patient's head at this location during side sleeping.

Additionally, in this example, the trough 3324 has sides which are adjacent to sides of the strap 3310. The width of the trough 3324 therefore matches the width of the strap 3310. This advantageously may help keep the strap 3310 aligned and centred within the trough 3324. It may also provide a visual guide for the user regarding alignment of the strap 3310.

5.3.3 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use. The vent 3400 may provide a continuous vent flow of gas from the interior of the plenum chamber 3200 to ambient throughout the patient's respiratory cycle.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel such as elbow 3610. In the example shown in FIGS. 8A-9C, the patient interface 3000 comprises a plurality of vents 3400. In particular, the patient interface 3000 comprises at least one vent 3400 in the plenum chamber 3200 and at least one vent in the elbow 3610. More particularly, the plenum chamber 3200 comprises two vents 3400. Each vent 3400 on the plenum chamber 3200 comprises an array of holes. The vent 3400 on the elbow 3610 also comprises an array of holes. The vent 3400 of the patient interface 3000 are sized and configured to provide sufficient gas washout throughout a range of therapeutic pressures.

The patient interface 3000 may comprise a diffuser configured to diffuse the flow of air though the vent to reduce vent noise and reduce jetting of air out of the vent holes. The diffuser may be provided to a cover over the vent holes. In some examples, the vent 3400 may comprise a vent module configured to be removed from the plenum chamber 3200. The vent module may comprise a diffuser.

5.3.4 Decoupling Structure(s)

In one form the patient interface 3000 includes at least one decoupling structure, for example, a swivel or a ball and socket. For example, the patient interface 3000 shown in FIGS. 8A-9C comprises an elbow 3610 configured the swivel with respect to the positioning and stabilising structure 3300. In this example the elbow 3610 is configured to swivel about an axis concentric with a circular opening in the positioning and stabilising structure 3300. In some examples of the present technology, the elbow 3610 may form part of a ball and socket joint to the positioning and stabilising structure 3300. For example, a ring having a partially spherical inner surface may be provided to the positioning and stabilising structure 3300 and may be configured to receive the elbow 3610. The elbow 3610 may have partially spherical outer surface complimentary to the partially spherical inner surface of the ring, thereby enabling the elbow 3610 to swivel with respect to the ring in a plurality of axes.

5.3.5 Connection Port

Connection port 3600 allows for connection to the air circuit 4170. In the exemplary patient interface 3000 shown in FIGS. 8A-9C, the elbow 3610 forms part of the connection port 3600. The elbow 3610, as a decoupling structure, decouples movement of the air circuit 4170 from the positioning and stabilising structure 3300 in order to reduce tube drag on the positioning and stabilising structure 3300.

5.3.6 Forehead Support

In one form, the patient interface 3000 includes a forehead support 3700. In other forms, the patient interface 3000 does not include a forehead support. Advantageously, the exemplary patient interface 3000 shown in FIGS. 8A-9C comprises a positioning and stabilising structure 3300 that is able to hold the seal-forming structure 3100 in sealing position without connection to a forehead support or any frame or strap members that lie in front of the patient's face at eye level.

5.3.7 Anti-Asphyxia Valve

In one form, the patient interface 3000 includes an anti-asphyxia valve. In some examples, the patient interface 3000 includes a plurality of anti-asphyxia valves. For example, where airflow is provided to a seal-forming structure 3100 via two fluid connections, two anti-asphyxia valves may be provided to the patient interface 3000, one at each fluid connection to the seal-forming structure 3100.

5.3.8 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 $cmH_2O$, or at least 10 $cmH_2O$, or at least 20 $cmH_2O$.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller, a therapy device controller, a pressure generator 4140, one or more protection circuits, memory, transducers 4270, data communication interface and one or more output devices. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components, including pneumatic components 4100, in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

5.4.1.4 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Algorithms

As mentioned above, in some forms of the present technology, the central controller may be configured to implement one or more algorithms expressed as computer programs stored in a non-transitory computer readable storage medium, such as memory. The algorithms are generally grouped into groups referred to as modules.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.5.1 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

5.6 Humidifier

5.6.1 Humidifier Overview

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.1.1 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.1.2 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.1.3 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.7 Glossary

For the purposes of the present technology disclosure, in certain forms of the present technology, one or more of the following definitions may apply. In other forms of the present technology, alternative definitions may apply.

5.7.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, $g$-$f/cm^2$ and hectopascal. 1 $cmH_2O$ is equal to 1 $g$-$f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.7.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.7.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.7.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

5.7.3 Anatomy 5.7.3.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

Glabella: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion

5.7.3.2 Anatomy of the Skull

Frontal bone: The frontal bone includes a large vertical portion, the squama frontalis, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.7.3.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.7.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.7.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.7.5.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.7.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.7.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.7.5.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.8 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.9 Reference Signs List

| | |
|---|---|
| 1000 | Patient |
| 1100 | Bed partner |
| 3000 | Patient interface |
| 3100 | Sealing or seal-forming structure |
| 3150 | Cradle cushion module |
| 3160 | Pillows cushion module |
| 3165 | Nasal pillow |
| 3200 | Plenum chamber |
| 3300 | Positioning and stabilising structure/headgear |
| 3301 | Force from upper portions of tubes |
| 3302 | Force from strap |
| 3303 | Sealing force tension |
| 3304 | Superior tube portion |
| 3305 | First end of the superior tube portion |
| 3306 | Second end of the superior tube portion |
| 3308 | Point alongside tab |
| 3310 | Strap |
| 3313 | Split |
| 3320 | Tab |
| 3321 | Slit angle |
| 3322 | Slit |
| 3323 | Length axis of the slit |
| 3324 | Trough |
| 3325 | Point along tubes proximate strap |
| 3326 | Superior end of slit |
| 3327 | Inferior end of slit |
| 3328 | Tab surface |
| 3329 | Posterior side |
| 3331 | Superior edge of tab |
| 3332 | Inferior edge of tab |
| 3347 | Rounded edges |
| 3348 | Patient contacting side |
| 3349 | Non-patient contacting side |
| 3350 | Gas delivery tubes |
| 3352 | Tube wall |
| 3353 | Path |
| 3354 | Tangent to the path |
| 3355 | Slit-adjacent portion |
| 3362 | Extendable concertina structure |
| 3363 | Non-extendable tube section |
| 3364 | Sleeve |
| 3370 | Ridge connecting portions |
| 3372 | Ridge |
| 3373 | Groove |
| 3374 | Curved ridge portion |
| 3375 | Straight ridge portion |
| 3376 | Curved groove portion |
| 3377 | Straight groove portion |
| 3382 | Interior Ridge |
| 3383 | Interior Groove |
| 3390 | Fluid connection opening |
| 3400 | Vent |
| 3600 | Connection port |
| 3610 | Elbow |
| 4000 | RPT device |
| 4010 | External housing |
| 4012 | Upper portion |
| 4014 | Lower Portion |
| 4015 | Panel |
| 4016 | Chassis |
| 4018 | Handle |
| 4020 | Pneumatic block |
| 4100 | Pneumatic components |
| 4110 | Air filter |
| 4112 | Inlet air filter |
| 4114 | Outlet air filter |
| 4122 | Inlet muffler |
| 4124 | Outlet muffler |
| 4140 | Pressure generator |
| 4142 | Controllable blower |
| 4144 | Brushless DC motor |
| 4170 | Air circuit |
| 4200 | Electrical components |
| 4202 | Printed Circuit Board Assembly (PCBA) |
| 4210 | Electrical power supply |
| 4220 | Input devices |
| 4270 | Transducers |
| 5000 | Humidifier |
| 5002 | Humidifier inlet |
| 5004 | Humidifier outlet |
| 5006 | Humidifier base |
| 5110 | Humidifier reservoir |
| 5130 | Humidifier reservoir dock |
| 5240 | Heating element |

The invention claimed is:

1. A patient interface comprising:
a plenum chamber pressurisable to a therapeutic pressure of at least 6 cmH$_2$O above ambient air pressure, said plenum chamber including a pair of plenum chamber inlet ports sized and structured to receive a flow of air at the therapeutic pressure for breathing by a patient;
a seal-forming structure constructed and arranged to seal with a region of the patient's face surrounding an entrance to the patient's airways for sealed delivery of the flow of air at the therapeutic pressure throughout the patient's respiratory cycle in use, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use;
a positioning and stabilising structure configured to hold the seal-forming structure in a therapeutically effective position on the patient's head during use, the positioning and stabilising structure comprising:
a connection port configured to be positioned superior to the patient's head in use and configured to be connected to an air delivery circuit to receive the flow of air at the therapeutic pressure;
a pair of gas delivery tubes connected to the connection port to receive the flow of air at the therapeutic pressure, each of the gas delivery tubes being connected to a corresponding one of the plenum chamber inlet ports to deliver the flow of air at the therapeutic pressure to the entrance of the patient's airways via the plenum chamber and the seal-forming structure, each of the gas delivery tubes being constructed and arranged to contact, in use, at least a region of the patient's head superior to an otobasion superior on a corresponding side of the patient's head, and each of the gas delivery tubes comprising:
a tube wall forming a flow path along the length of the gas delivery tube;
a tab connected to an exterior surface of the tube wall at a position so as to be located superior to the otobasion superior on the corresponding side of the patient's head and so as to extend in a posterior direction relative to the patient's head in use;

a slit formed in the tab and spaced from the tube wall, the slit comprising a first slit end and a second slit end configured to be positioned inferior to the first slit end relative to the patient's head in use;

a trough formed in the tab and extending from the slit away from the tube wall, the tab having a reduced thickness at the trough, wherein the first slit end is spaced farther from the tube wall than the second slit end, and wherein the slit follows an arcuate shape from the first slit end to the second slit end; and a length-adjustable strap constructed and arranged to contact, in use, a region of the patient's head inferior to or overlaying an occipital bone of the patient's head, the length-adjustable strap having a first strap end and a second strap end, each configured to removably connect to a corresponding tab by passing through a corresponding slit; and a vent structure comprising a plurality of holes formed on the plenum chamber to allow a continuous flow of gases exhaled by the patient from an interior of the plenum chamber to ambient, said vent structure being sized and shaped to maintain the therapeutic pressure in the plenum chamber in use, wherein the patient interface is configured to allow the patient to breath from ambient through their mouth in the absence of a flow of pressurised air through the plenum chamber inlet port, or the patient interface is configured to leave the patient's mouth uncovered.

2. The patient interface of claim 1, wherein each tab is integrally formed with a respective tube wall.

3. The patient interface of claim 1, wherein each tab has a superior edge and an inferior edge, the superior edge being longer than the inferior edge.

4. The patient interface of claim 1, wherein the second slit end is spaced from the tube wall by at least 5 mm.

5. The patient interface of claim 4, wherein the second slit end is spaced from the tube wall at least 7 mm.

6. The patient interface of claim 5, wherein the second slit end is spaced from the tube wall at least 8 mm.

7. The patient interface of claim 1, the first slit end is spaced from the tube wall by at least 8 mm.

8. The patient interface of claim 7, wherein the first slit end is spaced from the tube wall by at least 10 mm.

9. The patient interface of claim 8, wherein the first slit end is spaced from the tube wall by at least 12 mm.

10. The patient interface of claim 1, wherein a midpoint along the slit is spaced from the tube wall by a spacing within the range of 5 to 30 mm.

11. The patient interface of claim 10, wherein the spacing is within the range of 7 to 20 mm.

12. The patient interface of claim 11, wherein the spacing is within the range of 8 to 15 mm.

13. The patient interface of claim 12, wherein the spacing is within the range of 9 to 11 mm.

14. The patient interface of claim 1, wherein each of the gas delivery tubes comprises:

an extendable tube section configured to be located superior to the tab of the respective gas delivery tube relative to the patient's head in use; and a non-extendable tube section configured to be located inferior to the tab of the respective gas delivery tube relative to the patient's head in use.

15. The patient interface of claim 14, wherein each tab is joined to the tube wall of the respective gas delivery tube at the non-extendable tube section.

16. The patient interface of claim 1, wherein the length-adjustable strap comprises loop material, and wherein a piece of hook material is positioned on the length-adjustable strap at each of the first strap end and the second strap end to releasably attach to the loop material to removably connect each of the first strap end and the second strap end to a corresponding tab.

17. The patient interface of claim 1, wherein the trough shaped and dimensioned to allow the length-adjustable strap to be recessed into the trough when attached to the tab.

* * * * *